United States Patent
Alocilja et al.

(10) Patent No.: US 11,221,330 B2
(45) Date of Patent: Jan. 11, 2022

(54) METALLIC NANOPARTICLE SYNTHESIS WITH CARBOHYDRATE CAPPING AGENT

(71) Applicant: BOARD OF TRUSTEES OF MICHIGAN STATE UNIVERSITY, East Lansing, MI (US)

(72) Inventors: Evangelyn C. Alocilja, East Lansing, MI (US); Michael J. Anderson, Manassas, VA (US); Edith Torres-Chavolla, Baltimore, MD (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 16/273,722

(22) Filed: Feb. 12, 2019

(65) Prior Publication Data
US 2019/0346433 A1    Nov. 14, 2019

Related U.S. Application Data

(63) Continuation of application No. 14/356,406, filed as application No. PCT/US2012/063787 on Nov. 7, 2012, now Pat. No. 10,203,325.

(60) Provisional application No. 61/674,485, filed on Jul. 23, 2012, provisional application No. 61/557,644, filed on Nov. 9, 2011.

(51) Int. Cl.
| | | |
|---|---|---|
| *G01N 33/543* | (2006.01) | |
| *B22F 9/16* | (2006.01) | |
| *C12Q 1/6825* | (2018.01) | |
| *G01N 33/569* | (2006.01) | |
| *C23C 18/44* | (2006.01) | |

(52) U.S. Cl.
CPC ......... *G01N 33/54326* (2013.01); *B22F 9/16* (2013.01); *C12Q 1/6825* (2013.01); *C23C 18/44* (2013.01); *G01N 33/5434* (2013.01); *G01N 33/54346* (2013.01); *G01N 33/56911* (2013.01)

(58) Field of Classification Search
CPC ....... G01N 33/54326; G01N 33/56911; G01N 33/5434; G01N 33/54346; C23C 18/44; B22F 9/16; C12Q 1/6825
See application file for complete search history.

(56) References Cited

U.S. PATENT DOCUMENTS

| | | |
|---|---|---|
| 5,206,055 A | 4/1993 | Iacovangelo |
| 6,117,485 A | 9/2000 | Woodhall et al. |
| 6,183,545 B1 | 2/2001 | Okuhama et al. |
| 6,235,093 B1 | 5/2001 | Okuhama et al. |
| 6,929,675 B1 | 8/2005 | Bunge et al. |
| 7,179,660 B1 * | 2/2007 | Kirakossian ......... G01N 33/548 428/403 |
| 7,232,474 B2 | 6/2007 | Bouvrette et al. |
| 8,287,810 B2 | 10/2012 | Alocilja et al. |
| 9,581,590 B2 | 2/2017 | Alocilja et al. |
| 10,203,325 B2 | 2/2019 | Alocilja et al. |
| 2002/0034675 A1 | 3/2002 | Starz et al. |
| 2005/0287552 A1 | 12/2005 | Lin et al. |
| 2006/0148124 A1 | 7/2006 | Wilson |
| 2007/0190160 A1 | 8/2007 | Turos et al. |
| 2007/0269594 A1 | 11/2007 | Ackerson et al. |
| 2009/0123939 A1 | 5/2009 | Alocilja et al. |
| 2009/0258076 A1 | 10/2009 | Cheon et al. |
| 2009/0309597 A1 | 12/2009 | Horak et al. |
| 2010/0028559 A1 | 2/2010 | Yan et al. |
| 2010/0159471 A1 | 6/2010 | Taniuchi et al. |
| 2011/0105825 A1 | 5/2011 | Nayfach-Battilana |
| 2011/0171123 A1 | 7/2011 | Shirtliff et al. |
| 2011/0171749 A1 | 7/2011 | Alocilja et al. |

FOREIGN PATENT DOCUMENTS

| | | |
|---|---|---|
| WO | WO-2003/005029 A2 | 1/2003 |
| WO | WO-2010/028013 A2 | 3/2010 |
| WO | WO-2010/048623 A2 | 4/2010 |

OTHER PUBLICATIONS

Anderson et al. ("One step Alkaline synthesis of biocompatible gold nanoparticle using dextrin as capping agent", J. Nanopart. Res., vol. 13, pp. 2843-2851, published Dec. 31, 2010). (Year: 2010).*
Liang et al. ("Magnetic relaxation switch and colorimetric detection of thrombin using aptamer-functionalized gold-coated iron nanoparticles", Analytics Chimica Acta., vol. 689, pp. 243-249, published Jan. 27, 2011). (Year: 2011).*
Porta et al. ("Gold nanostructured materials for the selective liquid phase cataytic oxidation", Journal of Molecular Catalysis A: Chemical 204-205, pp. 553-559, published 2003) (Year: 2003).*

(Continued)

*Primary Examiner* — Tracy Vivlemore
*Assistant Examiner* — Nam P Nguyen
(74) *Attorney, Agent, or Firm* — Marshall, Gerstein & Borun LLP

(57) ABSTRACT

The disclosure relates to metal nanoparticle compositions and their methods of formation and use, in particular gold nanoparticles (AuNP) and gold-coated magnetic nanoparticles. Compositions according to the disclosure include aqueous suspensions of metal nanoparticles that are stabilized with one or more carbohydrate capping agents and/or that are functionalized with one or more binding pair members for capture/detection of a target analyte. The nanoparticle suspensions are stable for extended periods and can be functionalized as desired at a later point in time, typically prior to use in an assay for the detection of a target biological analyte. The stable nanoparticle suspension can be formed by the aqueous reduction of oxidized metal precursors at non-acidic pH values in the presence of a carbohydrate-based capping agent such as dextrin or other oligosaccharides.

17 Claims, 25 Drawing Sheets

Specification includes a Sequence Listing.

(56) References Cited

OTHER PUBLICATIONS

Torres-Chavolla et al. ("Characterization and Functionalization of Biogenic Gold Nanoparticles for Biosensing Enhancement", IEEE Transactions on Nanotechnology, vol. 9, No. 5, pp. 533-538, published Sep. 2010) (Year: 2010).*
Haizhen et al., "Synthesis of Chitosan-Stabilized Gold Nanoparticles in the Absence/Presence of Tripolyphosphate", Biomacromolecules, vol. 5, pp. 2340-2346, published 2004. (Year: 2004).*
"Oligosaccharide", Merriam-Webster (retrieved 2017).
Adinolfi et al., Modulating the activity of oligonucleotides by carbohydrate conjugation: solid phase synthesis of sucrose-oligonucleotide hybrids, Org. Biomol. Chem., 2(13):1879-86 (2004).
Ahmad et al., Extracellular biosynthesis of monodisperse gold nanoparticles by a novel extremophilic actinomycete, *Thermomonospora* sp., Langmuir, 19:3550-3 (2003).
An et al., Characterization of a thermostable UvrD helicase and its participation in helicase-dependent amplification, J. Biol. Chem., 280(32):28952-8 (2005).
Andreescu D, Sau TK, Goia DV (2006) Stabilizer-free nanosized gold sots. J Colloid Interface Sci 298 (2):742-751.
Andresen et al., Helicase dependent OnChip-amplification and its use in multiplex pathogen detection, Clin. Chim. Acta., 403(1-2):244-8 (2009).
Aslan et al., Nanogold plasmon resonance-based glucose sensing, Anal. Biochem., 330:145-55 (2004).
Azzazy et al., Nanodiagnostics: a new frontier for clinical laboratory medicine, Clin. Chem., 52(7):1238-46 (2006).
Bharde et al., Bacterial enzyme mediated biosynthesis of gold nanoparticles, J. Nanosci. Nanotechnol., 7(12):4369-77 (2007).
Brust et al., Synthesis of thiol-derivatised gold nanoparticles in a two-phase liquid-liquid system, J. Chem. Soc., Chem. Commun., 801-2 (1994).
Chah et al., Gold nanoparticles as a colorimetric sensor for protein conformational changes, Chem. Biol., 12(3):323-8 (2005).
Chandler, K. et al., Fe3O4@Au Nanoparticles for Extracting and Detecting Pathogenic Cells, Nano-Biosensors Lab at Michigan State University, Poster Presentation Jul. 24, 2012.
Chow et al., Application of isothermal helicase-dependent amplification with a disposable detection device in a simple sensitive stool test for toxigenic Clostridium difficile, J. Mol. Diagn., 10(5):452-8 (2008).
Dalovisio et al., Comparison of the amplified *Mycobacterium tuberculosis* (MTB) direct test, Amplicor MTB PCR, and IS6110-PCR for detection of MTB in respiratory specimens, Clin. Infect. Dis., 23(5):1099-1106 (1996).
Daniel et al., Gold nanoparticles: assembly, supramolecular chemistry, quantum-size-related properties, and applications toward biology, catalysis, and nanotechnology, Chem. Rev., 104(1):293-346 (2004).
Das et al., Gold nanoparticles: microbial synthesis and application in water hygiene management, Langmuir, 25(14):8192-9 (2009).
De la Fuente et al., Glyconanoparticles: types, synthesis and applications in glycoscience, biomedicine and material science, Biochim. Biophys. Acta, 1760(4):636-51 (2006).
DeLong, et al., Functionalized Gold Nanoparticles for the Binding, Stabilization, and Delivery of Therapeutic DNA, RNA, and Other Biological Macromolecules, 2010, Nanotechnology, Science and Applications, 3:53-63.
Demidov, Rolling-circle amplification in DNA diagnostics: the power of simplicity, Expert Rev. Mol. Diagn., 2(6):542-8 (2002).
Dextran, Product Information Sheet, CAS #: 9004-54-0, 3 pp. retrieved from the Internet in 2016 (published 2001).
Dextrans for General Research Applications, Product Sheet, Sigma-Aldrich, downloaded from the Internet at: <www.sigmaaldrich.com/life-science/biochemicals/biochemical-products.html?TablePage=22696471> (downloaded 2016).

Dudak et al., Rapid and label-free bacteria detection by surface plasmon resonance (SPR) biosensors, Biotechnol. J., 4(7):1003-11 (2009).
Fernandez et al., Comparison of three immunological diagnostic tests for the detection of avian tuberculosis in naturally infected red deer (*Cervus elaphus*), J. Vet. Diagn. Invest., 21(1):102-7 (2009).
Gill et al., Colorimetric detection of Helicobacter pylori DNA using isothermal helicase-dependent amplification and gold nanoparticle probes, Diagn. Microbiol. Infect. Dis., 62(2):119-24 (2008).
Gill et al., Nucleic acid isothermal amplification technologies: a review, Nucleosides Nucleotides Nucleic Acids, 27(3):224-43 (2008).
Global Tuberculosis Control: Epidemiology, Strategy, and Financing: WHO Report 2009.
Goldmeyer et al., Identification of *Staphylococcus aureus* and determination of methicillin resistance directly from positive blood cultures by isothermal amplification and a disposable detection device, J. Clin. Microbiol., 46(4):1534-6 (2008).
Goluch et al., A bio-barcode assay for on-chip attomolar-sensitivity protein detection, Lab Chip, 6(10):1293-9 (2006).
Guo et al., Synthesis and electrochemical applications of gold nanoparticles, Anal. Chern. Acta, 598(2):181-92 (2007).
Hardwicke et al., Dextrin-rhEGF Conjugates as Bioresponsive Nanomedicines for Wound Repair, J. Controlled Release, 130:275-83 (2008).
Hellyer et al., Strand displacement amplification: a versatile tool for molecular diagnostics, Expert Rev. Mol. Diagn., 4(2):251-61 (2004).
Hill HD, Mirkin CA (2006) The bio-barcode assay for the detection of protein and nucleic acid targets using DTT-induced ligand exchange. Nat Protoc 1 (1):324-336.
Huang et al., Beta-cyclodextrin controlled assembling nanostructures from gold nanoparticles to gold nanowires, Chemical Physical Letters, 389:14-18 (2004).
International Preliminary Report on Patentability of the International Bureau in International Application No. PCT/US2012/063787, dated May 13, 2014 (7 pages).
Jeong et al., Isothermal DNA amplification in vitro: the helicase-dependent amplification system, Cell Mol. Life Sci., 66(20):3325-36 (2009).
Ji et al., Size control of gold nanocrystals in citrate reduction: the third role of citrate, J. Am. Chem. Soc., 129(45):13939-48 (2007).
Kimling et al., Turkevich method for gold nanoparticle synthesis revisited, J. Phys. Chem. B, 110(32):15700-7 (2006).
Li et al., Multiple thiol-anchor capped DNA-gold nanoparticle conjugates, Nucleic Acids Res., 30(7):1558-62 (2002).
Xiliang Luo et al., Application of nanoparticles in electrochemical sensors and biosensors, Electroanalysis, 18(4):319-26 (2006).
Ma et al., One-step synthesis of cystine-coated gold nanoparticles in aqueous solution, Colloids and Surfaces A: Physiocochem. Eng. Aspects, 317:229-33 (2008).
Mahalanbis et al., An integrated disposable device for DNA extraction and helicase dependent amplification, Biomed. Microdevices, 12(2):353-9 (2010).
Mori et al., Loop-mediated isothermal amplification (LAMP): a rapid, accurate, and cost-effective diagnostic method for infectious diseases, J. Infect. Chemother., 15(2):62-9 (2009).
Newman J.D.S. et al., Formation of Gold Nanoparticles Using Amine Reducing Agents, 2006, American Chemical Society, pp. 5882-5887.
Pal S, Alocilja EC, Downes FP (2007) Nanowire labeled direct-charge transfer biosensor for detecting Bacillus species. Biosens Bioelectron 22 (9-10):2329-2336.
Palomino, Nonconventional and new methods in the diagnosis of tuberculosis: feasibility and applicability in the field, Eur. Respir. J., 26(2):339-50 (2005).
Perkins et al., Progress towards improved tuberculosis diagnostics for developing countries, Lancet, 367(9514):942-3 (2006).
Pham et al., Application of citrate-stabilized gold-coated ferric oxide composite nanoparticle for biological separations, Journal of Magnetism and Magnetic Materials, 320:2049-55 (2008).
Polte J, Ahner TT, Delissen F, Sokolov S, Emmerling F, Thunemann AF, Kraehnert R (2010) Mechanism of gold nanoparticle formation in the classical citrate synthesis method derived from coupled in situ XANES and SAXS evaluation. J Am Chem Soc 132 (4):1296-1301.

(56) References Cited

OTHER PUBLICATIONS

Pourceau et al., Carbohydrate-oligonucleotide conjugates, Curr. Protoc. Nucleic Acid Chem., Chapter 4, Unit 4.38 (2009).

Pumera et al., Direct voltammetric determination of gold nanoparticles using graphite-epoxy composite electrode, Electrochim. Acta, 50:3702-7 (2005).

Rechberger et al., Optical properties of two interacting gold nanoparticles, Optics Comm., 220:137-41 (2003).

Rozen et al., Primer3 on the WWW for general users and for biologist programmers, IN: Misener et al. (eds.), Bioinformatics: Methods and Protocols, New Jersey: Humana Press (2000).

Salavati-Niasari et al., Star-shaped PbS nanocrystals prepared by hydrothermal process in the presence of thioglycolic acid, Polyhedron, 35:149-53 (2012).

Selvakannan et al., Water-dispersible tryptophan-protected gold nanoparticles prepared by the spontaneous reduction of aqueous chloroaurate ions by the amino acid, J. Colloid Interface Sci., 269(1):97-102 (2004).

Slocik et al., Synthesis of gold nanoparticles using multifunctional peptides, Small, 1(11):1048-52 (2005).

Takahashi et al., Amphiphilic polysaccharide nanoballs: a new building block for nanogel biomedical engineering and artificial chaperones, ACS Nano, 5(1):337-45 (2011).

The International Search Report and the Written Opinion of the International Searching Authority, dated Apr. 1, 2013, International Application No. PCT/US2012/063787 (11 pages).

Torres-Chavolla, et al., Nanoparticle Based DNA Biosensor for Tuberculosis Detection Using Thermophilic Helicase-Dependent Isothermal Amplification (2011) 4614-4618.

Turkevich et al., A study of the nucleation and growth processes in the synthesis of colloidal gold, Discuss Faraday Soc., 1:55-75 (1951).

Venkatpurwar et al., Porphyran capped gold nanoparticles as a novel carrier for delivery of anticancer drug: in vitro cytotoxicity study, Int. J. Pharm., 409(1):314-20 (May 2011).

Vincent et al., Helicase-dependent isothermal DNA amplification, EMBO Rep., 5(8):795-800 (2004).

Wang et al., Nanoparticle-Labeled Biosensor for Sensitive and Rapid Detection of Bacterial Pathogen, World Congress on Biosensors (Presented on May 18, 2012).

Wang et al., Oleic acid as the capping agent in the synthesis of noble metal nanoparticles in imidazolium-based ionic liquids, Chem. Commun. (Camb.), (24):2545-7 (2006).

Wang et al., One-pot preparation of dextran-capped gold nanoparticles at room temperature and colorimetric detection of dihydralazine sulfate in uric sample, Anal. Methods, 2:1982-88 (2010).

Zhang D, Carr DJ, Alocilja EC (2009) Fluorescent bio-barcode DNA assay for the detection of *Salmonella enterica* serovar Enteritidis. Biosens Bioelectron 24 (5):1377-1381.

Zhang et al., A multiplex nanoparticle-based bio-barcoded DNA sensor for the simultaneous detection of multiple pathogens, Biosens. Bioelectron., 26(4):1736-42 (2010).

Zhou et al., Minute synthesis of extremely stable gold nanoparticles, Nanotechnology, 20(50):505606 (2009).

\* cited by examiner

METALLIC NANOPARTICLE SYNTHESIS WITH CARBOHYDRATE CAPPING AGENT

CROSS REFERENCE TO RELATED APPLICATIONS

Priority is claimed to U.S. Provisional Application Nos. 61/557,644 (filed on Nov. 9, 2011) and 61/674,485 (filed Jul. 23, 2012), both of which are incorporated herein by reference in their entireties.

STATEMENT OF GOVERNMENT INTEREST

This invention was made with government support under 2007-ST-061-000003 awarded by the U.S. Department of Homeland Security. The government has certain rights in the invention.

REFERENCE TO A SEQUENCE LISTING SUBMITTED IN A COMPUTER READABLE FORMAT

The application contains nucleotide sequences which are identified with SEQ ID NOs. The Sequence Listing provided in computer readable form, incorporated herein by reference in its entirety, is identical to the written copy of the Sequence Listing provided with the application.

BACKGROUND OF THE DISCLOSURE

Field of the Disclosure

The disclosure generally relates to the formation of metal nanoparticles (e.g., gold nanoparticles) using a carbohydrate capping agent (e.g., dextrin). The metal nanoparticles can be in the form of a metal nanoparticle core stabilized by the carbohydrate capping agent. Alternatively, the metal nanoparticles can be in the form of a nanoparticle core having a metal coating in a core-shell configuration, where the metal shell is stabilized by the carbohydrate capping agent. The metal nanoparticles are formed by reduction of a metal precursor at a neutral or alkaline pH in the presence of the carbohydrate capping agent, and optionally a nanoparticle core material. The carbohydrate capping agent provides a stabilized aqueous suspension of the metal nanoparticles. The metal nanoparticles can be used for detection of an analyte by functionalization of the nanoparticles with a binding pair member specific to the target analyte of interest.

Brief Description of Related Technology

Gold nanoparticles (AuNPs) have attracted considerable interest in recent years due to their wide range of application, for example in sensing methods as tracers and transducers. The spectral, electrical and chemical properties make AuNPs suited for sensing, molecular labeling, and bio-engineering (Li et al. 2002; Rechberger et al. 2003). Sensing technologies utilizing AuNPs include oxidation-reduction potentiometry, conductors in electrical circuits, and spectral reporters (2-100 nm) in solution (Dudak 2009; Pal et al. 2007; Xiliang et al. 2006). The sensing methodologies using AuNPs rely on attached surface biomolecules as recognition materials. The ligands (DNA, proteins, polymer, peptides, and antibodies) act as capping agents to stabilize the AuNP in aqueous solution and provide surface functionality, biological capture and chemical reactivities (Chah et al. 2005; Goluch et al. 2006; Hill and Mirkin 2006; Slocik et al. 2005; Zhou et al. 2009).

The most common AuNP synthesis techniques utilize citrate under acidic reaction conditions. Common methodologies for AuNP synthesis are: 1) non-polar synthesis using the Brust method (Brust et al. 1994), 2) aqueous generation with the Turkevich method (Turkevich et al. 1951), and 3) biological synthesis using microbial agents (Ahmad et al. 2003; Bharde et al. 2007; Das et al. 2009). Aqueous generation has been under study due to the "greener" nature of water-based reactions in comparison to non-polar solvents. The basic chemistry of formation for citrate reduction techniques is to reduce the $Au^{3+}$ ion to $Au^0$ and stabilize the surface of the colloidal gold with a capping molecule that is soluble in the synthesis media (Daniel and Astruc 2004). Traditional aqueous synthesis involves low pH and/or high temperatures; which limit the number of biological capping agents, requiring a ligand exchange step after synthesis for sensing applications.

Neutral to alkaline synthesis methods have been explored using microbial synthesis (Bharde et al. 2007; Das et al. 2009), sodium hydroxide reduction (Zhou et al. 2009) and sodium borohydride reactions (Brust et al. 1994). The appeal of microbial synthesis is that biological ligands (proteins, carbohydrates, glyco-lipids) are present during generation in an aqueous medium and could be used as the capping agent but have not shown the same control, stability and consistency of generation as current techniques for AuNP production (Torres-Chavolla 2010). Several biological agents have been explored for the reduction and capping of $[AuCl_4]^-$ to produce gold colloids, including cysteine (Ma and Han 2008), tryptophan (Selvakannan et al. 2004), and ascorbic acid (Andreescu et al. 2006). The standard Burst technique of sodium borohydride formation requires a non-polar generation and a phase exchange for water soluble functionalization. Recent studies have explored the use of polymers for capping agents with sodium hydroxide as the reduction agent; but have not explored biomolecule attachments (Zhou et al. 2009). The reaction pH in most of these methods is within the acidic range and the resulting AuNP size is between 30-80 nm. Limited exploration of citrate has been conducted in alkaline conditions but reported as extremely slow and still requires post production ligand exchange (Ji et al. 2007).

Glyconanoparticles (carbohydrate functionalized nanoparticles) have recently been explored for carbohydrate-carbohydrate and carbohydrate-protein interaction studies, and for applications in biomedicine, including bio-labeling and biosensors (Asian et al. 2005; de la Fuente and Penades 2006). Gold glyconanoparticles (AuGlycoNP) can be synthesized using a modification of the Brust methodology using one of several mono and disaccharides (e.g. lactose, maltose, and glucose) (de la Fuente and Penades 2006) for post production attachment with a ligand exchange technique. Recent work has successfully used cyclo-dextrin, dextrin, and glucose as aqueous capping agents after organic media production (Huang et al. 2004; Porta and Rossi 2003).

SUMMARY

The disclosure relates to alkaline metallic nanoparticle generation procedures, for example in the 7-11 pH range. Longer reaction times (e.g., on the order of hours), can permit the introduction of bio-molecular capping agents during synthesis. The disclosed process is generally an aqueous, alkaline synthetic process for the formation of metal nanoparticles (e.g., AuNPs or a (magnetic) nanoparticle core with a gold shell) using a carbohydrate or oligosaccharide (e.g., dextrin) capping agent during generation. The carbohydrate capping agent is a removable capping agent that is compatible with standard post-production functionalization methodologies for the metal nanoparticles, for example using thiolated ligands to functionalize a gold surface. The reaction rates for nanoparticle formation are dependent on pH, temperature, and capping agent concentration, which factors contribute to control the reaction speed of the process as well as the particle-size distribution characteristics of the formed nanoparticles.

In one aspect, the disclosure relates to a method for method for forming metal nanoparticles, the method comprising: (a) providing an aqueous medium, the aqueous medium comprising (i) water and (ii) metal ions in solution in the water; and (b) reducing the metal ions in the aqueous medium at a neutral or alkaline pH value (e.g., pH 7-12) in the presence of a carbohydrate capping agent (e.g., dextrin) for a time sufficient to form a plurality of reduced metal nanoparticles as a suspension stabilized in the aqueous medium with the carbohydrate capping agent.

In another aspect, the disclosure relates to method for forming gold nanoparticles, the method comprising (a) providing an aqueous medium, the aqueous medium comprising (i) water and (ii) gold ions (e.g., in solution or otherwise mixed in the water); and (b) reducing the gold ions in the aqueous medium at a pH value ranging from 8 to 11 in the presence of a dextrin capping agent for a time sufficient to form a plurality of reduced gold nanoparticles as a suspension stabilized in the aqueous medium with the dextrin capping agent; wherein the plurality of reduced gold nanoparticles has an average particle size ranging from 5 nm to 15 nm. In a refinement, the metal ion reduction in part (b) is performed in the presence of galactose in addition to the dextrin capping agent.

In another aspect, the disclosure relates to a stabilized metal nanoparticle suspension composition comprising: (a) water in sufficient amount to provide an aqueous medium; and (b) a plurality of stabilized metal nanoparticles stably suspended in the aqueous medium, each stabilized metal nanoparticle comprising: (i) a metal nanoparticle core and (ii) a carbohydrate capping agent present as a layer on an outer surface of the metal nanoparticle core in an amount sufficient to stabilize the metal nanoparticle suspension. In a refinement, the stabilized metal nanoparticles are capable of remaining stably suspended in the aqueous medium for a period of at least 90 days when stored at room temperature. In another refinement, each stabilized metal nanoparticle further comprises a binding pair member (A) immobilized on the outer surface of the metal nanoparticle core and (B) capable of binding to a target analyte.

In another aspect, the disclosure relates to a method for functionalizing stabilized metal nanoparticles, the method comprising: (a) providing the stabilized metal nanoparticle suspension according to any of the various disclosed embodiments (e.g., dextrin-stabilized gold or other metal nanoparticles); (b) providing a binding pair member comprising (i) an immobilization moiety for immobilizing the binding pair member onto the metal nanoparticle and (ii) a binding moiety capable of binding to a target analyte or a second binding pair member; and (c) performing a ligand exchange process between the stabilized metal nanoparticle suspension and the binding pair member, thereby (i) removing at least some of the carbohydrate capping agent present as a layer on the outer surface of the metal nanoparticle and (ii) immobilizing the binding pair member on the outer surface of the metal nanoparticle via the immobilization moiety. In a refinement, the metal nanoparticles comprise gold nanoparticles; and the binding pair member comprises (A) a ssDNA oligonucleotide as the binding moiety, the ssDNA being capable of specific binding to a target ssDNA analyte and (B) a thiol functional group as the immobilization moiety. In another refinement, the metal nanoparticles comprise gold nanoparticles; and the binding pair member comprises (B) a carboxylate functional group as the binding moiety and (B) a thiol functional group as the immobilization moiety.

In another aspect, the disclosure relates to a method for forming metal nanoparticles, the method comprising: (a) providing an aqueous medium, the aqueous medium comprising (i) water, (ii) metal ions in solution in the water, and (iii) core nanoparticles dispersed in the water; and (b) reducing the metal ions in the aqueous medium at a neutral or alkaline pH value in the presence of a carbohydrate capping agent for a time sufficient to form a plurality of reduced metal nanoparticles as a suspension stabilized in the aqueous medium with the carbohydrate capping agent, the reduced metal nanoparticles comprising a metal coating from the reduced metal ions on the core nanoparticles. In an extension, the method further comprises: (c) magnetically separating (i) reduced metal nanoparticles comprising the metal coating on the core nanoparticles from (ii) reduced metal nanoparticles formed without a core nanoparticle interior. In an embodiment, the core nanoparticles comprise magnetic nanoparticles, and the reduced metal nanoparticles comprise metal-coated magnetic nanoparticles. In another embodiment, the metal ions comprise gold ions, the core nanoparticles comprise iron oxide nanoparticles, and the metal nanoparticles comprise gold-coated iron oxide nanoparticles.

In another aspect, the disclosure relates to a stabilized metal nanoparticle suspension composition comprising: (a) water in sufficient amount to provide an aqueous medium; and (b) a plurality of stabilized metal nanoparticles stably suspended in the aqueous medium, each stabilized metal nanoparticle comprising: (i) a nanoparticle core, (ii) a metal coating on the nanoparticle core, and (iii) a carbohydrate capping agent present as a layer on an outer surface of the metal coating in an amount sufficient to stabilize the metal nanoparticle suspension. In an embodiment, the nanoparticle core comprises a magnetic material. In another embodiment, the nanoparticle core comprises an iron oxide and the metal coating on the nanoparticle core comprises gold. In a refinement, each stabilized metal nanoparticle further comprises a binding pair member (A) immobilized on the outer surface of the metal coating and (B) capable of binding to a target analyte.

In another aspect, the disclosure relates to a method for functionalizing stabilized metal nanoparticles, the method comprising: (a) providing a stabilized metal nanoparticle suspension according to any of the various disclosed embodiments (e.g., including a (magnetic) nanoparticle core); (b) providing a binding pair member comprising a binding moiety capable of binding to a target analyte or a second binding pair member; and (c) performing a ligand exchange process between the stabilized metal nanoparticle suspension and the binding pair member, thereby (i) removing at least some of the carbohydrate capping agent present as a layer on the outer surface of the metal nanoparticle and (ii) immobilizing the binding pair member on the outer surface of the metal nanoparticle. In an embodiment, the binding pair member comprises an antibody capable of specific binding to a target bacterial or viral analyte. In another embodiment, the binding pair member comprises an immunoconjugate binding pair member, the immunoconjugate comprising: (i) an immunoglobulin comprising (A) an Fc region and (B) an antigen-binding region being capable of specifically binding to the target analyte, and (ii) an immunoglobulin-binding protein having a binding affinity to the Fc region of the immunoglobulin, the immunoglobulin-binding protein being immobilized on the outer surface of the metal nanoparticle and bound to the Fc region of the immunoglobulin. In a refinement, (i) the immunoglobulin-binding protein can be selected from the group consisting of protein A, protein G, protein A/G, and combinations thereof, and/or (ii) the immunoglobulin can be selected from the group consisting of IgA, IgD, IgE, IgG, IgM, subclasses thereof, and combinations thereof. In another embodiment, the carbohydrate capping agent comprises dextrin, the nanoparticle core comprises an iron oxide, and the metal coating on the nanoparticle core comprises gold.

In another aspect, the functionalized stabilized metal nanoparticles can be used in a method for detecting the target analyte, the method comprising: (a) forming a conjugate between the target analyte and the binding pair member of the functionalized stabilized metal nanoparticles (e.g., by contacting the components in a sample matrix), (b) optionally magnetically separating the analyte conjugate from the sample matrix (e.g., when the metal nanoparticles include a magnetic nanoparticle core), and (c) detecting the metal component of the nanoparticles corresponding to the analyte conjugate (e.g., electrochemically detecting the gold or other metallic portion of the nanoparticulate analyte conjugate).

In another aspect, the disclosure relates to a method for forming magnetic gold nanoparticles, the method comprising: (a) providing an aqueous medium, the aqueous medium comprising (i) water, (ii) gold ions in solution in the water, and (iii) magnetic iron oxide nanoparticles dispersed in the water; and (b) reducing the gold ions in the aqueous medium at a pH value ranging from 8 to 11 in the presence of a dextrin capping agent for a time sufficient to form a plurality of reduced magnetic gold nanoparticles as a suspension stabilized in the aqueous medium with the dextrin capping agent, the magnetic gold nanoparticles comprising a gold coating from the reduced gold ions on the magnetic iron oxide nanoparticles; wherein the plurality of reduced magnetic gold nanoparticles has an average particle size ranging from 5 nm to 20 nm.

In another aspect, the disclosure relates to a method for detecting a target analyte, the method comprising: (a) providing a functionalized, stabilized metal nanoparticle comprising: (i) a metal nanoparticle, (ii) a carbohydrate capping agent (e.g., dextrin) present as a layer on an outer surface of the metal nanoparticle (e.g. in an amount sufficient to stabilize the metal nanoparticle as a suspension in an aqueous medium), and (iii) a binding pair member (A) immobilized on the outer surface of the metal nanoparticle and (B) capable of binding to a target analyte; (b) forming an analyte-nanoparticle conjugate between a target analyte and the binding pair member of the functionalized, stabilized metal nanoparticle (e.g., by contacting the two components in a sample matrix containing the target analyte); and (c) detecting a metal component (e.g., gold) of the metal nanoparticle of the analyte-nanoparticle conjugate (e.g., in the presence of the carbohydrate capping agent; detection or lack thereof of the metal component can be correlated to a corresponding positive or negative detection of the target analyte in the original sample matrix). In a refinement, part (c) comprises electrochemically detecting the metal component of the metal nanoparticle in the presence of the carbohydrate capping agent. In another refinement, (i) the analyte-nanoparticle conjugate further comprises a magnetic moiety and (ii) the method further comprises magnetically separating the analyte-nanoparticle conjugate from a sample matrix in which the analyte-nanoparticle conjugate is formed prior to detecting the metal component thereof. In another refinement, the binding pair member comprises an antibody capable of specific binding to a target bacterial analyte or a target viral analyte. In another refinement, the binding pair member comprises an immunoconjugate binding pair member as described above. In an embodiment, (i) the metal nanoparticle comprises a metal nanoparticle core formed from the metal component (e.g., a gold nanoparticle providing gold/gold ions as the component to be detected), and (ii) the carbohydrate capping agent is present as a layer on an outer surface of the metal nanoparticle core, In another embodiment, (i) the metal nanoparticle comprises (A) a nanoparticle core (e.g., a magnetic material such as an iron oxide) and (B) a metal coating on the nanoparticle core (e.g., a gold coating providing gold/gold ions as the component to be detected), the metal coating being formed from the metal component, and (ii) the carbohydrate capping agent is present as a layer on an outer surface of the metal coating.

Various refinements and extensions of the foregoing methods and compositions are possible. For example, the metal ions can comprise gold ions and the metal nanoparticles can comprise gold nanoparticles. More generally, the metals for the metal ions and corresponding metal nanoparticles/metal shells can be selected from the group consisting of gold, chromium, copper, zinc, nickel, cadmium, silver, cobalt, indium, germanium, tin, lead, arsenic, antimony, bismuth, chromium, molybdenum, manganese, iron, ruthenium, rhodium, palladium, osmium, iridium, platinum, alloys thereof, and combinations thereof. The aqueous medium can further comprise a counter ion in solution in the water from a dissolved metal ionic compound providing the metal ions. Reduction of the metal ions can be performed at a temperature ranging from 20° C. to 100° C. In a refinement, the aqueous medium further comprises a combined reducing agent for reducing the metal ions and pH-adjusting agent (e.g., a carbonate such as sodium carbonate) for maintaining the neutral or alkaline pH value of the aqueous medium during reduction. The carbohydrate capping agent can comprise an oligosaccharide having 3 to 100 saccharide residues. The carbohydrate capping agent can comprise a plurality of oligosaccharides having a distribution of lengths. The carbohydrate capping agent can comprise one or more glucose residues. The carbohydrate capping agent can be in a substantially non-oxidized form. In a refinement, reduction of the metal ion is performed in the presence of a monosaccharide and/or a disaccharide in addition to the carbohydrate capping agent. In another refinement, the carbohydrate capping agent comprises at least one of a monosaccharide and a disaccharide; and reduction of the metal ion is performed in the presence of at least one non-carbohydrate capping agent in addition to the carbohydrate capping agent. The carbohydrate capping agent can have a concentration in the aqueous medium selected to control one or more size parameters of the plurality of metal nanoparticles formed during reduction. The plurality of reduced metal nanoparticles can have an average particle size ranging from 2 nm to 50 nm, and it can have a (substantially) normal size distribution with a standard deviation of 25% or less relative to the average particle size of the distribution. In an embodiment, at least some of the carbohydrate capping agent is present as a layer on an outer surface of each stabilized metal nanoparticle. In a refinement, the nanoparticle formation process can further include functionalization of the nanoparticles, for example wherein (i) the aqueous medium in part (b) further comprises a binding pair member comprising (A) an immobilization moiety for immobilizing the binding pair member onto the reduced metal nanoparticle and (B) a binding moiety capable of binding to a target analyte or a second binding pair member; and (ii) part (b) is performed for a time sufficient in the presence of the binding pair member to additionally immobilize the binding pair member on an outer surface of the reduced metal nanoparticle via the immobilization moiety. The immobilization moiety of the binding pair member can comprise a carbohydrate moiety conjugated to the binding moiety. In an embodiment, the reaction media and/or resulting compositions are free or substantially free (e.g., not measurable or not added to the reaction/product mixtures) of non-carbohydrate capping agents (e.g., citric acid or derivatives thereof such as citric acid (alkali metal) salts).

Additional features of the disclosure may become apparent to those skilled in the art from a review of the following detailed description, taken in conjunction with the drawings, examples, and appended claims.

BRIEF DESCRIPTION OF THE DRAWINGS

For a more complete understanding of the disclosure, reference should be made to the following detailed description and accompanying drawings wherein.

Figure 1A:
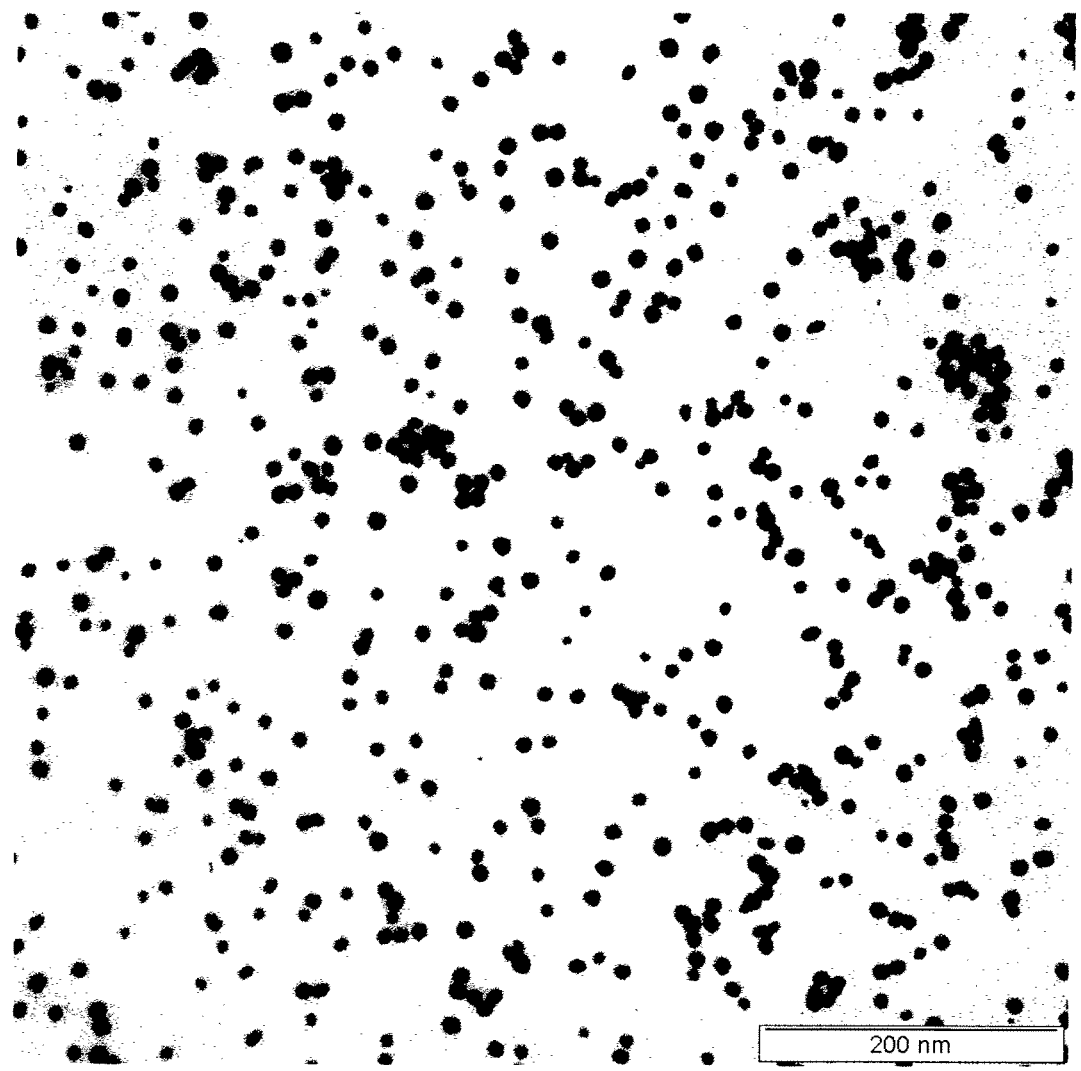
FIGS. 1a-1d illustrate the AuNP synthesis process according to the disclosure as in Example 1 and produced at optimal synthesis conditions: 50° C., 24 hr, and 10.0 g/L dextrin; (a) TEM image of AuNP sample (scale bar: 200 nm); (b) High magnification of image (a) (scale bar: 50 nm); (c) UV-Vis spectra v. reaction time showing an increase with time of the AuNP characteristic absorbance peak (520 nm); and (d) visual color change reaction time series. The samples were diluted 1:4 with distilled water for imaging.

While the disclosed compositions, methods, and kits are susceptible of embodiments in various forms, specific embodiments of the disclosure are illustrated in the drawings (and will hereafter be described) with the understanding that the disclosure is intended to be illustrative, and is not intended to limit the claims to the specific embodiments described and illustrated herein.

DETAILED DESCRIPTION

The disclosure generally relates to metal nanoparticle compositions and their methods of formation, in particular gold nanoparticles (AuNPs) such as solid AuNPs or nanoparticles with a gold (shell)-nanoparticle (core) structure. The metal nanoparticles can be in the form of a metal nanoparticle core stabilized by the carbohydrate capping agent (e.g., a metal nanoparticle formed substantially entirely from gold). Alternatively, the metal nanoparticles can be in the form of a nanoparticle core (e.g., non-metallic and/or magnetic) having a metal coating in a core-shell configuration (e.g., a magnetic iron oxide-gold composite particle in a core-shell configuration), where the core-shell nanoparticle is stabilized by the carbohydrate capping agent (e.g., via interactions between the metal shell and the capping agent). Compositions according to the disclosure include aqueous suspensions of metal nanoparticles that are stabilized with one or more carbohydrate capping agents. The nanoparticle suspensions are stable for extended periods (e.g., for at least several months) and can be functionalized as desired at a later point in time, typically prior to use in an assay for the detection of a target biological analyte (e.g., using an antibody, DNA probe, or other biomolecular probe capable of binding to the target analyte as a functionalization agent). The stable nanoparticle suspension can be formed by the aqueous reduction of metal precursor ions at non-acidic pH values in the presence of a carbohydrate-based capping agent such as dextrin or other oligosaccharides. In some embodiments, functionalization of the metal nanoparticles can be performed in the same reaction system as that used for nanoparticle formation, for example simultaneously performed with some or all of the nanoparticle formation process.

Metal Nanoparticle Formation

Methods of metal nanoparticle formation according to the disclosure generally are performed in an aqueous reaction system including metal ions to be reduced in solution in the aqueous medium. The metal ions in the aqueous medium are reduced at a neutral or alkaline pH value in the presence of a carbohydrate capping agent under suitable reaction conditions to form a plurality of reduced metal nanoparticles (e.g., at a reaction temperature and reaction time sufficient to convert all or substantially all of the metal ion precursors). The reaction generally includes an initial nucleation stage to form metallic nuclei followed by a longer growth stage in which metal ions reduced on the nuclei surfaces create the final metal nanoparticles. The plurality of reduced metal nanoparticles are in the form of a stabilized suspension of metal nanoparticles in the aqueous medium, where the carbohydrate capping agent stabilizes the formed nanoparticle suspension.

The specific metal ions or oxidized metal-containing species in solution and selected as precursors to the desired metal nanoparticles are not particularly limited and are suitably chosen according to a desired end use/application of the nanoparticle suspension. In an embodiment, the metal ions include gold ions (e.g., Au(III), $Au^{3+}$) and are selected to form gold metal nanoparticles (AuNPs). The metal ions can be free in solution or coordinated/coupled with other (ionic) species (e.g., $Au^{3+}$, $[AuCl_4]^-$, $[AuCl_3OH]^-$, $[AuCl_2(OH)_2]^-$, $[AuCl(OH)_3]^-$ or $[Au(OH)_4]^-$, where the oxidation level of gold in each case is +3). Other potential metal ions can include chromium, copper, zinc, nickel, cadmium, silver, cobalt, indium, germanium, tin, lead, arsenic, antimony, bismuth, chromium, molybdenum, manganese, iron, ruthenium, rhodium, palladium, osmium, iridium, and platinum.

In some embodiments, two or more types of metal ions can be in solution in the aqueous medium to provide metal nanoparticles formed from alloys of two or more elemental metals. The concentration of metal ions in solution prior to reaction is not particularly limited, but it suitably ranges from 0.1 mM to 1000 mM (e.g., at least 0.1 mM, 1 mM, or 10 mM and/or up to 100 mM or 1000 mM).

The metal ions are suitably introduced into the aqueous medium as a dissolvable ionic compound, for example a salt or acid. A suitable source of gold ions is chloroauric acid ($HAuCl_4$), which can provide Au(III) in the form of $[AuCl_4]^-$. Other salts/compounds including the oxidized metal precursor such as halides (e.g., chlorides, bromides, fluorides, iodides), sulfates, sulfites, thiosulfates, nitrates, nitrites, carboxylates, sulfonates, and hydrogenated forms thereof (e.g., as in $HAuCl_4$) can be used as desired and depending on the particular metal ion to be introduced into the aqueous medium.

In some embodiments, the aqueous medium further includes, prior to reduction of the metal ions, a population of nanoparticles serving as cores/nucleation sites for deposition of the reduced metal ions, thus permitting the formation of metal nanoparticles having a core-shell structure including a nanoparticle core with a metallic shell. The nanoparticle core material is not particularly limited and can be non-metallic, metallic (e.g., different from the metal to be reduced as a shell), magnetic, etc. Magnetic nanoparticle cores are particularly useful to permit the resulting metal nanoparticle to function as both a magnetic sample/analyte separator and concentrator (e.g., due to the magnetic core) as well as a signal transducer (e.g., due to the electrical properties of the metal shell material such as gold).

The magnetic nanoparticles according to the disclosure are not particularly limited and generally include any nano-sized particles (e.g., about 1 nm to about 1000 nm) that can be magnetized with an external magnetic/electrical field. The magnetic nanoparticles more particularly include superparamagnetic particles, which particles can be easily magnetized with an external magnetic field (e.g., to facilitate separation or concentration of the particles from the bulk of a sample medium) and then redispersed immediately once the magnet is removed (e.g., in a new (concentrated) sample medium). Thus, the magnetic nanoparticles are generally separable from solution with a conventional magnet. Suitable magnetic nanoparticles are provided as magnetic fluids or ferrofluids, and mainly include nano-sized iron oxide particles ($Fe_3O_4$ (magnetite) or $\gamma$-$Fe_2O_3$ (maghemite)) suspended in a carrier liquid. Such magnetic nanoparticles can be prepared by superparamagnetic iron oxide by precipitation of ferric and ferrous salts in the presence of sodium hydroxide and subsequent washing with water. A suitable source of $\gamma$-$Fe_2O_3$ is Sigma-Aldrich (St. Louis, Mo.), which is available as a nano-powder having particles sized at <50 nm with a specific surface area ranging from about 50 $m^2/g$ to about 250 $m^2/g$. Preferably, the magnetic nanoparticles have a small size distribution (e.g., ranging from about 5 nm to about 25 nm) and uniform surface properties (e.g., about 50 $m^2/g$ to about 245 $m^2/g$.).

More generally, the magnetic nanoparticles can include ferromagnetic nanoparticles (i.e., iron-containing particles providing electrical conduction or resistance). Suitable ferromagnetic nanoparticles include iron-containing magnetic metal oxides, for example those including iron either as Fe(II), Fe(III), or a mixture of Fe(II)/Fe(III). Non-limiting examples of such oxides include FeO, $\gamma$-$Fe_2O_3$ (maghemite), and $Fe_3O_4$ (magnetite). The magnetic nanoparticles can also be a mixed metal oxide of the type $M1_xM2_{3-x}O_4$, wherein M1 represents a divalent metal ion and M2 represents a trivalent metal ion. For example, the magnetic nanoparticles may be magnetic ferrites of the formula $M1Fe_2O_4$, wherein M1 represents a divalent ion selected from Mn, Co, Ni, Cu, Zn, or Ba, pure or in admixture with each other or in admixture with ferrous ions. Other metal oxides include aluminum oxide, chromium oxide, copper oxide, manganese oxide, lead oxide, tin oxide, titanium oxide, zinc oxide and zirconium oxide, and suitable metals include Fe, Cr, Ni or magnetic alloys.

Reduction of the metal ions in the aqueous medium is performed at a neutral or alkaline pH value, for example ranging from 7 to 12 (e.g., where the pH value is essentially constant throughout the reaction, or it may vary within the range during reaction). In various embodiments, the pH value of the reaction medium can be at least 7, 7.5, 8, 8.5, 9 and/or up to 8, 8.5, 9, 9.5, 10, 11, 12. The selection and control of the desired pH value can be effected by any suitable base and/or buffer system as is generally know in the art. As described below, in some embodiments, the pH value can be controlled by selection of a reducing agent. Non-acidic pH values, in particular those that are mildly basic or otherwise near to a physiological pH value, are desirable in certain embodiments to promote functionalization of the eventual metal nanoparticles with biomolecules that would be denatured or whose activity would otherwise be reduced or negated in an acidic environment.

The reaction temperature of the reduction process is not particularly limited, for example being at room temperature (e.g., 20° C. to 25° C.) or at mildly elevated temperatures relative to room temperature. In various embodiments, the temperature of the aqueous medium can range from 20° C. to 100° C. during the reduction reaction, for example being at least 20° C., 25° C., 30° C., 35° C., or 40° C. and/or up to 30° C., 35° C., 40° C., 50° C., 60° C., 70° C., 80° C., 90° C., or 100° C. in various embodiments.

Reduction of the metal ions in the aqueous medium is suitably effected by the addition of a chemical reducing agent to the aqueous medium. Suitable reducing agents are those that are effective at reducing metallic ions at the neutral/alkaline pH of the aqueous medium (e.g., they do not require an acidic pH and/or do not themselves create an acidic environment). In some embodiments, the reducing agent is a combined reducing agent for reducing the metal ions and pH-adjusting agent for maintaining the neutral or alkaline pH value of the aqueous medium. Suitable combined reducing and pH-adjusting agents include metal (e.g., alkali or alkali earth metal) carbonates or bicarbonates such as sodium carbonate ($Na_2CO_3$). However, other reducing agents that are operative at neutral/alkaline pH values can be used even if they do not also function as a pH-adjusting agent (e.g., in which case other non-reducing bases/buffers can be used to independently control the pH value). Examples of other suitable reducing agents include hydrides (e.g., lithium aluminum hydride ($LiAlH_4$), sodium borohydride ($NaBH_4$), diisobutylaluminum hydride (DIBAH)), earth metals including K, Na, Li, Mg, Ba, Ca), sulfates (e.g., metallic such as from iron (II) or other soluble iron (II) salts), peroxides (e.g., those functioning as reducing agents at alkaline pH such as hydrogen peroxide ($H_2O_2$)), sulfides (e.g., metallic such as from alkali metals like Na), and amines (e.g., including ammonium salts thereof such as hydroxyl amine ($NH_2OH$) or hydroxyl amine hydrochloride ($NH_2OH.HCl$)).

The carbohydrate useful as a capping agent according to the disclosure is generally an oligo- or polysaccharide having a plurality of saccharide residues (e.g., having a general formula $C_m(H_2O)_n$ for unmodified carbohydrates with residues derived from monosaccharides having a general formula $(CH_2O)_n$). In some embodiments, the carbohydrate capping agent can be a carbohydrate derivative, for example having additional functional groups such as carboxylate group or nitrogen-containing groups (e.g., amino, N-acetyl). The capping agent can include linear and/or branched carbohydrates, such as those including α- or β-glycosidic bonds (e.g., α(1,4) or α(1,6) glycosidic linkages as in dextrin or other starch-based capping agents). The specific carbohydrate capping agent is suitably selected so that it has at least some hydrophilic character (e.g., to promote a water-stable suspension), and it can be a water-soluble carbohydrate in some refinements. In some embodiments, the capping agent is in a substantially non-oxidized form (e.g., being (substantially) free from aldose, ketose, and/or carboxylate (acid or anion) functionalities either for a portion of or the whole capping agent molecule; based on an absence of such functionalities and/or the inability to detect (non-trace) levels of the functionalities in the capping agent), for example as added to the reaction mixture, as present during reaction, and/or as bound/conjugated to the metal nanoparticles in the reaction product. In other embodiments, other non-carbohydrate capping agents such as polyethylethene glycol (e.g., or other polyether or polyethylene oxide), various silanes, polyacrylamide, and other negatively charged polymers can be used (e.g., for use instead of or in combination with other carbohydrate capping agent such as oligosaccharide; suitably in combination with a monosaccharide, a disaccharide, or a derivative thereof as described below as an additive to the carbohydrate capping agent system). The concentration of the capping agent in solution prior to reaction is not particularly limited, but it suitably ranges from 1, 2, 5, or 10 g/L to 15, 25, 35, 50, or 100 g/L (e.g., where selection of the capping agent concentration can permit selection of an average metal nanoparticle size and/or size distribution resulting from the concentration).

The capping agent is suitably an oligosaccharide having 3 to 100 saccharide residues, for example at least 3, 5, 10, 15, 20, 25, 30, or 40 and/or up to 10, 20, 30, 40, 50, 60, 80, or 100 saccharide residues. In some embodiments, the capping agent represents a plurality of oligosaccharides or polysaccharides having a distribution of sizes/lengths (e.g., in terms of number of saccharide residues). In such cases, ranges characterizing the oligosaccharide capping agent in terms of number of saccharide residues can represent an average of the distribution (e.g., number or other average), or the ranges can represent upper and lower bounds for the distribution (e.g., within 1, 2, or 3 standards deviations from the mean; representing the 1%/99%, 5%/95%, or 10%/90% cut points of the cumulative size distribution).

In some embodiments, the carbohydrate capping agent can include one or more glucose residues (e.g., D-glucose; having a plurality of glucose residues such as where the capping agent essentially consists only of glucose residues). However, the capping agent can include other saccharide residues alone, in combination with glucose, and/or in combination with each other, for example including those from allose, altrose, mannose, gulose, iodose, galactose, talose, xylose, arabinose, fucose, and/or fructose. As noted above, the capping agent can include carbohydrate derivates, for example including saccharide residues from glucuronic acid (e.g., also including salts and esters thereof), N-acetyl-D-glucosamine (e.g., derived from chitin), and D-glucosamine (e.g., derived from chitosan).

Oligomeric carbohydrate capping agents containing the various saccharide residues can be (synthetic) oligosaccharides having a selected length/saccharide sequence, or they can be formed from naturally occurring polysaccharides. Polysaccharides can be subjected to enzymatic or other chemical forms of hydrolysis to form shorter oligosaccharides, generally with an element of random size distribution. Examples of suitable precursor polysaccharides for capping agents include starch (e.g., forming dextrin), amylose, amylopectin, cellulose, laminarin, chrysolaminarin, xylan, arabinoxylan, mannan, fucoidan, and galactomannan. In an embodiment, the capping agent is a dextrin (e.g., linear, branched, or cyclic; suitably linear and/or branched having at least 10, 20, or 30 saccharide residues), for example being formed from starch (e.g., including amylose and/or amylopectin).

In an embodiment, the aqueous medium can include a saccharide-based moiety in addition to the carbohydrate capping agent during metal ion reduction. The additional saccharide-based moiety can be included to form metal nanoparticle suspensions that remain stably suspended for even longer periods (i.e., in comparison to suspensions stabilized with the capping agent alone) and can be a reducing sugar. The additional stabilizing agent is generally a monosaccharide, a disaccharide, or a derivative thereof.

Suitable examples include sucrose, glucose, fructose, mannose, galactose, glyceradehyde, lactose, and maltose, although the additional stabilizing agent more generally can include any combination of the saccharide residues listed above for the oligomeric/carbohydrate capping agent.

Stabilized Metal Nanoparticle Compositions

The above process results in the formation of a metal nanoparticle composition. Once the reduction reaction has progressed (e.g., to completion, such as once substantially all precursor metal ion reactant has been consumed), the aqueous medium contains a plurality of reduced metal nanoparticles as a suspension stabilized in the aqueous medium with the carbohydrate capping agent. Accordingly, the disclosure also relates to a stabilized metal nanoparticle suspension composition that includes water in a sufficient amount to provide an aqueous medium and stabilized metal nanoparticles stably suspended in the aqueous medium. The aqueous medium suspension can have the same neutral or alkaline pH as that used for metal ion reduction (e.g., ranging from 7 to 12), or it can be adjusted to a different pH value post-reduction (e.g., still generally in the neutral or alkaline range) for storage or to facilitate subsequent functionalization. The stabilized metal nanoparticles in the suspension individually can include a metal nanoparticle core (e.g., generally having a spherical or nearly spherical/spheroidal shape) and a carbohydrate capping agent present as a layer on an outer surface of the metal nanoparticle core in an amount sufficient to stabilize the metal nanoparticle suspension (i.e., the capping agent need not completely envelop the nanoparticle core, but it is present near the core surface in a sufficient amount to prevent/inhibit substantial settling or agglomeration of the nanoparticles). Similarly, stabilized metal nanoparticles in the suspension individually can include a core-shell nanoparticle and a carbohydrate capping agent present as a layer on an outer surface of the metal nanoparticle shell in an amount sufficient to stabilize the metal nanoparticle suspension. In various embodiments, the carbohydrate capping agent can form a complete or partial layer (e.g., a monolayer or a plurality of layers) that is adsorbed or otherwise bound to the metal nanoparticle surface such as by electrostatic interactions between the metal nanoparticle surface and hydroxyl groups of the carbohydrate capping agent present at the neutral or alkaline pH of the aqueous medium.

The population of the reduced metal nanoparticles as produced (e.g., in suspension as formed in the aqueous medium or otherwise) generally has a particle size ranging from 2 nm to 50 nm (e.g., a number-, weight-, or volume-average particle size). For example, the average size of the nanoparticle distribution can be at least 2, 5, 8, 10, 12, or 15 nm and/or up to 8, 10, 12, 15, 20, 25, 30, 40, or 50 nm. In an embodiment, the distribution of metal nanoparticles also has a relatively narrow size distribution, for example a substantially normal size distribution with a standard deviation of 25% or less relative to the average particle size of the distribution (e.g., a monomodal distribution; having a $\sigma/\langle x \rangle$ for a normal distribution of not more than 25%, 20%, 15%, or 10% and/or at least 1%, 2%, 5%, 8% or 10%). As illustrated in the examples below, various size parameters of the metal nanoparticle distribution (e.g., average size, distribution width) can be selected/controlled by selecting one or more reduction reaction parameters. Examples of suitable reaction/operating conditions that can be selected to control nanoparticle size include capping agent concentration, metal ion concentration, reducing agent concentration, reaction temperature, reaction pH, length and/or size distribution of the oligomeric capping agent.

The capping agent-stabilized metal nanoparticles remain stably suspended in the aqueous medium for extended periods without (substantial) settling or agglomeration of the nanoparticles. For example, the suspension can remain stable for at least 90 days when stored at room temperature. In various embodiments, the suspension is stable or capable of remaining stable for periods of at least 90, 120, 180, 270, or 360 days and/or up to 270, 360, 720, or 1080 days and/or at storage temperatures generally between 20° C. and 25° C., in particular at a neutral or alkaline pH. The metal nanoparticles remain stably suspended in the aqueous medium in part based on the hydrophilic character of various functional groups the carbohydrate capping agent (e.g., hydroxyl groups, which can impart a water-soluble character to low-molecular weight capping agents).

Functionalization of Metal Nanoparticles

The carbohydrate-capped metal nanoparticles can be functionalized, for example with a biomolecule, according to various methods known in the art for any desired nanoparticle application (e.g., use in a biosensor to detect a target biological analyte, use as a vehicle for delivering the functionalized biomolecule to a target). General methods of biomolecule attachment can include physical adsorption (e.g., resulting from electrostatic metal-biomolecule interactions), direct binding (e.g., based on affinity interactions between the metal and a functional group of the biomolecule, such as between a thiolated biomolecule and gold), covalent attachment (e.g., between the biomolecule and a covalent linking intermediate that is bound to the metal nanoparticle, such as through thiolated carboxylic acids, EDAC-mediated attachment of biomolecules, biotin-streptavidin linking, and azide-linking or other "click" functionalization techniques) (DeLong 2010).

Functionalization of the metal nanoparticles is generally performed by immobilizing a binding pair member on the metal nanoparticles (e.g., on the outer nanoparticle surface). The binding pair member can be selected for its ability to specifically or non-specifically bind to a target analyte (e.g., a protein, virus, bacteria, ssDNA, such a DNA of a target microorganism or complementary ssDNA when the binding pair member is for immobilization of a biobarcode) or for its ability to form covalent bonds or otherwise bind with a second binding pair member (e.g., that itself can specifically or non-specifically bind to a target analyte).

The binding pair member includes an immobilization moiety for immobilizing the binding pair member onto the metal nanoparticle and a binding moiety. In some embodiments, the immobilization moiety is a functional group that is normally part of the binding pair member (e.g., a polar group capable of electrostatic interactions). In other embodiments, the immobilization moiety is a functional group that is added to the binding pair member to facilitate binding to the metal nanoparticle (e.g., a thiol group for gold attachment; a carbohydrate/saccharide moiety for enhanced electrostatic interactions with a metal surface). In some embodiments, the binding moiety is the portion of the binding pair member that is capable of specific or non-specific binding to the target analyte (e.g., ssDNA probe for ssDNA binding/detection, binding region of antibody for virus/bacteria binding/detection). In other embodiments, the binding moiety is the portion of binding pair member that is capable of binding to the second binding pair member (e.g., a carboxylate group such as a carboxylic acid or salt capable of forming covalent links to an immobilization moiety of the second binding pair member).

In one embodiment, the binding pair member can be immobilized on the metal nanoparticle using a ligand exchange process known in the art. In a general ligand exchange process, the carbohydrate capping agent stabilizing the metal nanoparticle suspension is removed from the outer surface of the metal nanoparticles (e.g., partial or complete removal of the capping agent). Removal of the capping agent promotes increased access to surface areas of the metal nanoparticles, thus allowing immobilization of the binding pair member on the outer surface of the metal nanoparticle via the immobilization moiety (e.g., by contacting/incubating the metal nanoparticle suspension with the binding pair member). As illustrated in Examples 1 and 2 below, a suitable ligand exchange method for gold nanoparticles includes a DTT-mediated removal of the carbohydrate capping agent followed by immobilization of a thiolated binding pair member (e.g., thiolated ssDNA oligonucleotide) on the gold nanoparticle surface. As illustrated in Example 3 below, another suitable ligand exchange method for gold nanoparticles includes a surfactant-mediated removal of the carbohydrate capping agent followed by immobilization of a thiolated binding pair member (e.g., thiolated carboxylic acid used for further covalent attachment) on the gold nanoparticle surface.

In another embodiment, specific binding pair members such as antibodies can be immobilized on the metal nanoparticle via adsorption. For example, antibodies can be bound (e.g., by direct physical adsorption) to the outer metal portion of the metal nanoparticle by incubating the antibodies in a buffer suspension of the metal nanoparticles. Additionally, an immunoglobulin (antibody) with an Fc region and an antigen-binding region capable of specifically binding to the target analyte (e.g., IgA, IgD, IgE, IgG, IgM, subclasses thereof, and combinations thereof) can be incubated with an immunoglobulin-binding protein having a binding affinity to the Fc region of the immunoglobulin (e.g., a bacterial surface protein such as protein A, protein G, protein A/G, and combinations thereof), such that the immunoglobulin-binding protein binds to the outer metal portion of the metal nanoparticle (e.g., via adsorption) and the Fc region of the immunoglobulin, thereby preferentially orienting the resulting immunoconjugate so that the antigen-binding region of the immunoglobulin is outwardly directed relative to the metal nanoparticle (e.g., which enhances binding/capture efficiency of the immunoglobulin).

In another embodiment, the binding pair member can be immobilized on the metal nanoparticle in the same aqueous reaction medium used for metal ion reduction and metal nanoparticle formation (e.g., a "one-pot" synthesis). In such cases, functionalization of the nanoparticles can be performed during the reduction reaction (e.g., initiation of functionalization step at the same time the reduction reaction is initiated or at a subsequent time when the reduction reaction is still proceeding), or functionalization can be performed subsequent to the reduction reaction (e.g., initiation of functionalization step immediately after or a short time after the reduction reaction is complete, such as within 24 hours). Addition and incubation of the binding pair member in the aqueous medium for a sufficient time (e.g., under suitable temperature and pH conditions, such as those suitable for the reduction reaction itself) allow immobilization of the binding pair member on the outer surface of the metal nanoparticle via the immobilization moiety. In an embodiment, the binding pair member/binding moiety thereof can be conjugated to a carbohydrate moiety analogous to any of those described above in relation to the carbohydrate capping agent (e.g., a monosaccharide, a disaccharide, and/or an oligosaccharide of the various saccharide residues or derivatives thereof). In one refinement, the aqueous reduction medium can include carbohydrate moieties both from the capping agent (e.g., which is free from binding moieties or binding pair members) and from those conjugated to the binding pair members. In another refinement, the only carbohydrate moieties present in the aqueous medium are capping agent species that are also conjugated to the binding pair members (e.g., in which case the carbohydrate serves as both the capping agent for nanoparticle formation/stabilization and the immobilization moiety for the binding pair member). Methods of conjugating saccharide moieties to molecules useful as binding pair members (e.g., ssDNA oligonucleotides) are known in the art (Adinolfi 2004; Pourceau 2009).

Binding Pair Members

As described above, the metal nanoparticles can be functionalized with binding pair members to detect a variety of target analytes in biosensor applications. The binding pair member is selected to be capable of binding (specific or non-specific) to a target analyte so that the metal nanoparticle composition can be used for the (selective) detection of the target analyte in a sample.

An analyte (or target analyte) generally includes a chemical or biological material, including living cells, in a sample which is to be detected using the functionalized nanoparticle composition or other analyte probe. The analyte can include pathogens of interest (e.g., bacterial pathogens such as *E. coli* O157:H7, *B. anthracis*, *B. cereus*, in addition to those listed above). The analyte also may be an antigen, an antibody, a ligand (i.e., an organic compound for which a receptor naturally exists or can be prepared, for example one that is mono- or polyepitopic, antigenic, or haptenic), a single compound or plurality of compounds that share at least one common epitopic site, and a receptor (i.e., a compound capable of binding to an epitopic or determinant site of a ligand, for example thyroxine binding globulin, antibodies, enzymes, Fab fragments, lectins, nucleic acids, protein A, complement component C1q). In some embodiments, the term "analyte" also can include an analog of the analyte (i.e., a modified form of the analyte which can compete with the analyte for a receptor) that can also be detected using the functionalized nanoparticle nanoparticle composition.

The specific binding pair member generally includes one of two different molecules, each having a region or area on its surface or in a cavity that specifically binds to (i.e., is complementary with) a particular spatial and polar organization of the other molecule. The binding pair members can be referenced as a ligand/receptor (or antiligand) pair. These binding pair members include members of an immunological pair such as antigen-antibody. Other specific binding pairs such as biotin-avidin (or derivatives thereof such as streptavidin or neutravidin), hormones-hormone receptors, IgG-protein A, polynucleotide pairs (e.g., DNA-DNA, DNA-RNA), DNA aptamers, biomimetic antibody-antigen (e.g., molecularly imprinted synthetic polymer having specific binding capability with the antigen), and whole cells are not immunological pairs, but can be used as binding pair members within the context of the present disclosure.

Preferably, the binding pair members are specific to each other and are selected such that one binding pair member is the target analyte of interest or a component thereof (e.g., a specific surface protein or other surface component of specific bacteria or other pathogen of interest), and the other binding pair member is the constituent bound to the conductive polymer of the particulate composition. Binding specificity (or specific binding) refers to the substantial recognition of a first molecule for a second molecule (i.e., the first and second members of the binding pair), for example a polypeptide and a polyclonal or monoclonal antibody, an antibody fragment (e.g., a Fv, single chain Fv, Fab', or F(ab')$_2$ fragment) specific for the polypeptide, enzyme-substrate interactions, and polynucleotide hybridization interactions. Preferably, the binding pair members exhibit a substantial degree of binding specificity and do not exhibit a substantial amount of non-specific binding (i.e., non-covalent binding between molecules that is relatively independent of the specific structures of the molecules, for example resulting from factors including electrostatic and hydrophobic interactions between molecules).

Substantial binding specificity refers to an amount of specific binding or recognition between molecules in an assay mixture under particular assay conditions. Substantial binding specificity relates to the extent that the first and second members of the binding pair to bind only with each other and do not bind to other interfering molecules that may be present in the analytical sample. The specificity of the first and second binding pair members for each other as compared to potential interfering molecules should be sufficient to allow a meaningful assay to be conducted for the target analyte. The substantial binding specificity can be a function of a particular set of assay conditions, which includes the relative concentrations of the molecules, the time and temperature of an incubation, etc. For example, the reactivity of one binding pair member with an interfering molecule as compared to that with the second binding pair member is preferably less than about 25%, more preferably less than about 10% or about 5%.

A preferred binding pair member is an antibody (an immunoglobulin) that specifically binds to and is thereby defined as complementary with a particular spatial and polar organization of another molecule (e.g., an antigen). Antibodies generally include Y-shaped proteins on the surface of B cells that specifically bind to antigens such as bacteria, viruses, etc. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b, IgG3, IgM, etc. Fragments thereof may include Fab, Fv and F(ab')$_2$, and Fab'. In addition, aggregates, polymers, and conjugates of immunoglobulins or their fragments can be used where appropriate so long as binding affinity for a particular molecule is maintained.

EXAMPLES

The following examples illustrate the disclosed compositions and methods, but are not intended to limit the scope of any claims thereto.

Example 1—Synthesis of Dextrin-Capped Gold Nanoparticles

The synthesis described in this example generates glyco-AuNPs under mild alkaline conditions in an aqueous medium to provide a "greener" alternative to Brust and Turkevich methodologies. The biologically compatible, one-step technique in this example used dextrin as a capping agent and sodium carbonate as a reducing agent for a chloroauric acid gold precursor. The generated particles were relatively mono-dispersed and water soluble with a range of controllable mean diameters from 5.9 to 16.8 nm±1.6 nm. The produced AuNPs were stable in water for more than six months stored at room temperature (21° C.) in the generation solution and without protection from light. The example further evaluates the effect of temperature, pH, and dextrin concentration on the synthesis procedure and the resulting AuNP diameter of the AuNP distribution. These factors were found to control the reaction speed. The produced glyco-AuNPs were successfully functionalized with DNA oligonucleotides, and the functionalization efficiency was similar to citrate-generated AuNPs. The alkaline synthesis potentially allows simultaneous synthesis and functionalization procedures, which could significantly reduce the time of current ligand exchange methodologies.

AuNP Synthesis:

A gold chloride (HAuCl$_4$) stock solution (20 mM) (#520918-5G from Aldrich) was prepared using distilled sterile water and was stored under refrigeration. The dextrin stock solution (25 g/L) (#31400 Fluka) was prepared using deionized water and autoclaved prior to use. A mixture of distilled sterile water and dextrin stock solution was added to a sterile 250 mL flask according to the desired dextrin concentration within the 2.5 to 20.0 g/L final working range. A volume of 5 mL of HAuCl$_4$ stock solution was added to the reaction and adjusted to pH 9 using filter-sterile 10% sodium carbonate (Na$_2$CO$_3$), the final HAuCl$_4$ concentration in the reaction was 2 mM. Finally, the reaction volume (50 mL) was completed by using pH adjusted distilled water (pH 9). The flask was incubated in the dark at 50° C. with continuous shaking for 8 hours. Particle formation was observed through the following stages of color change; clear, purple tint, red tint, and red (520 nm), the same color sequence as citrate reduction (Polte et al. 2010). The effects of pH (from 3 to 11) and temperature (25° C. and 50° C.) on the synthesized particles were evaluated and compared to sodium citrate generated AuNPs (Hill and Mirkin 2006).

AuNP characterization:

The AuNP formation was evaluated using UV/Vis scanning spectroscopy, and the size distribution by light scattering and transmission electron microscopy (TEM). UV/Vis spectra were measured using a UV-VIS-NIR Scanning Spectrophotometer (Shimadzu). Particle size and distribution were obtained from TEM images and collected with a JEOL 100CX Transmission Electron Microscope. A 1:4 diluted suspension of the AuNPs in distilled water was sonicated for 5 min before 5 µl of the sample was transferred to a formvar/carbon coated copper grid (300 mesh) for imaging.

AuNP functionalization: In order to evaluate the ability to use the dextrin-coated AuNPs for future sensing assays, thiol-modified oligonucleotides were attached to the AuNP surface using the ligand exchange method for functionalizing citrate-coated AuNPs (Hill and Mirkin 2006; Zhang et al. 2009). An oligonucleotide (sequence 5'-TTA TTC GTA GCT AAA AAA AAA A-3'; SEQ ID NO: 1) was used with 5' 6-Carboxyfluorescein (6-FAM; $\lambda$ excitation=495 nm, $\lambda$ emission=520 nm) and 3' thiol modifications (IDT Coralville, Iowa). The oligonucleotide was ligand-exchanged for the capping agent post-AuNP production. The AuNPs were centrifuged into a pellet and separated from the excess DNA ligand, washed 3 times, and resuspended in dithiothreitol (DTT) buffer. The DTT AuNP-DNA solution was heated for 60 minutes at 50° C. in order to ligand-exchange DTT for the thiolated DNA. The fluorescence signal from the supernatant was measured for DNA conjugation efficiency using a 527-547 nm emission filter (VICTOR3 1420 Multilabel counter, Perkin-Elmer).

Figure 1B:
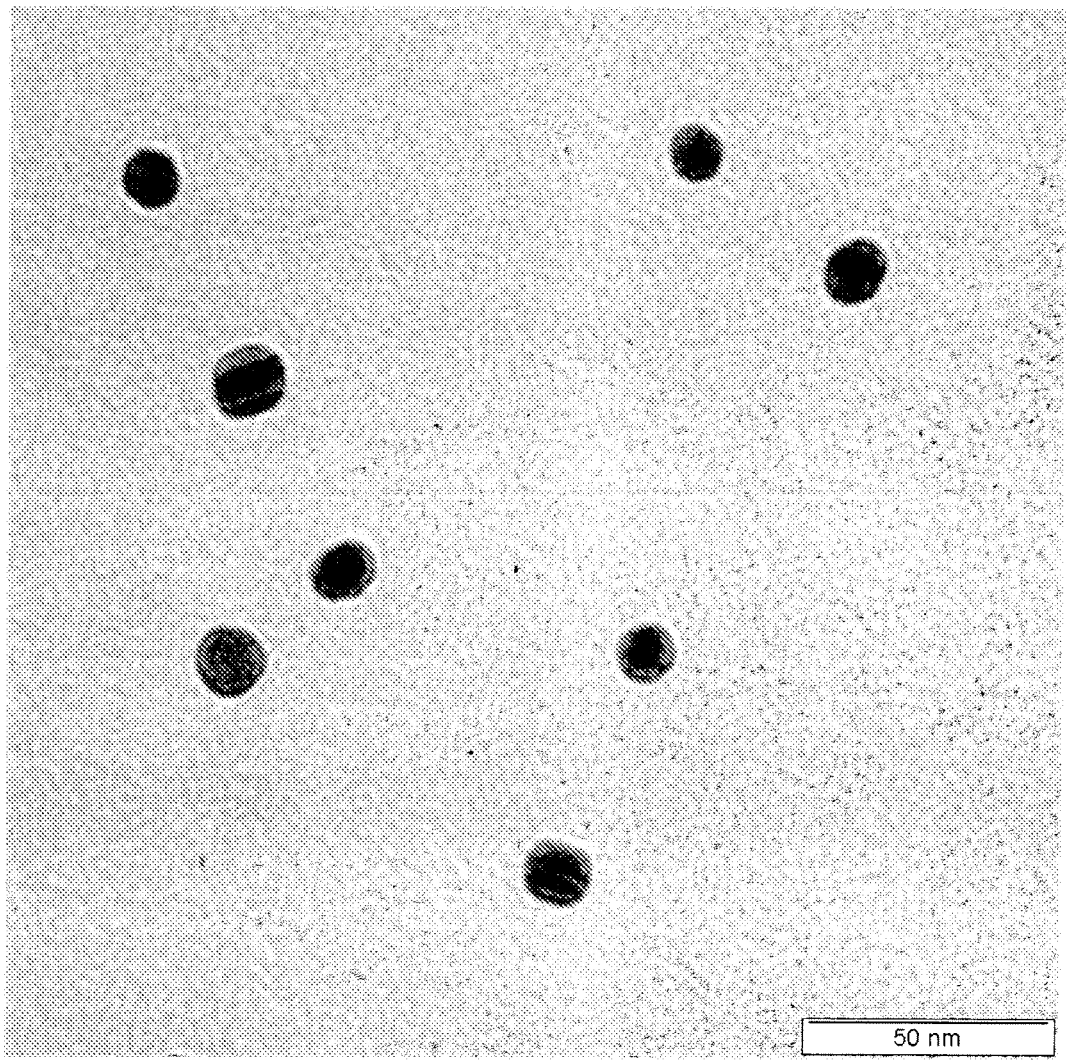
Figure 1C:
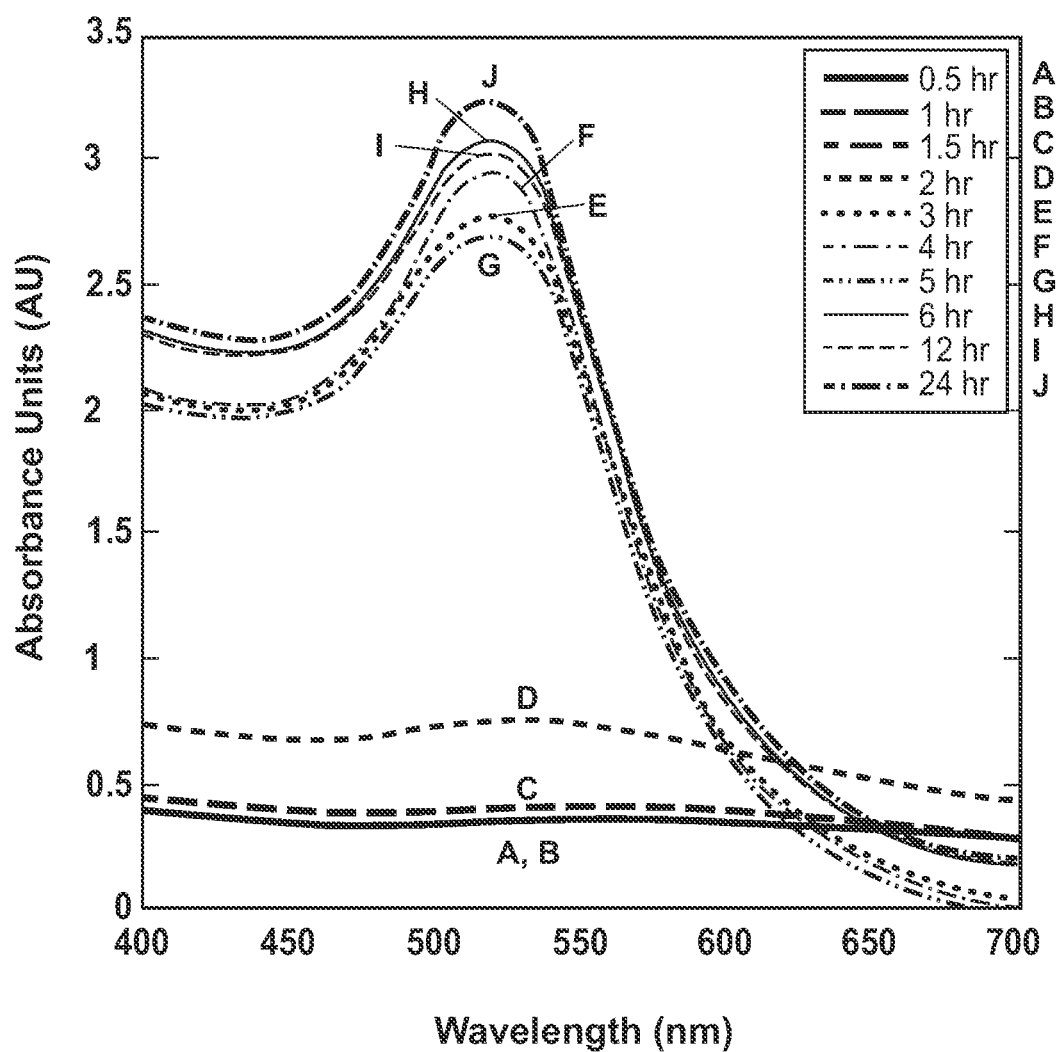
Figure 1D:
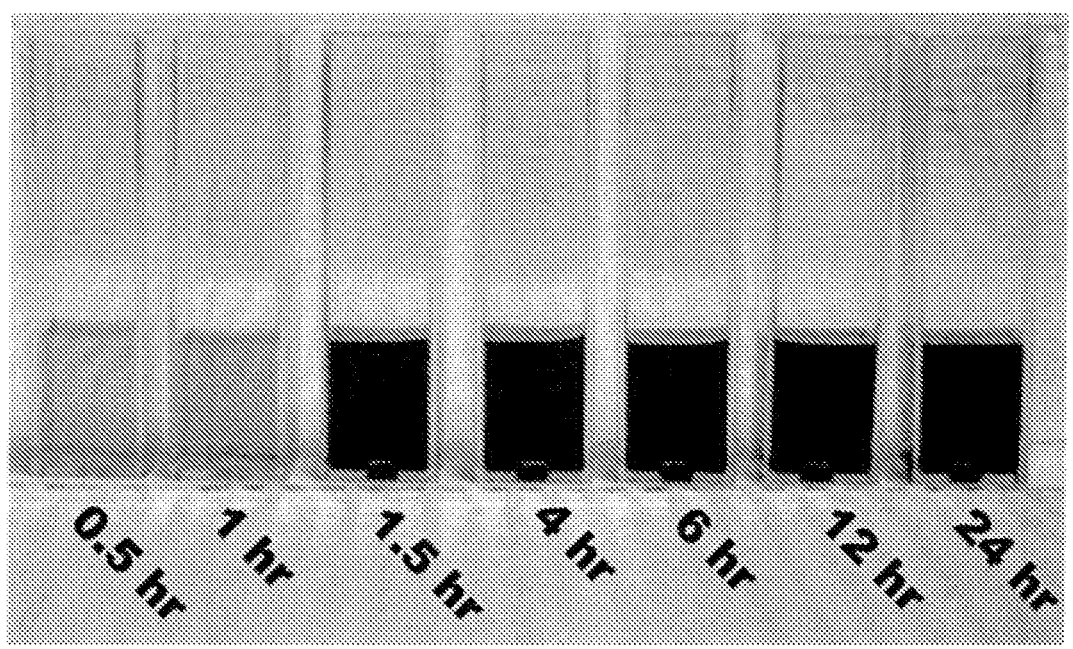

Results—AuNP synthesis:

AuNPs were successfully synthesized at alkaline conditions using dextrin as a capping agent. FIG. 1a shows a typical TEM image generated at 10.0 g/L dextrin concentration, 2 mM $HAuCl_4$, pH 9.0 and 50° C. The particle generation was monitored over 24 hours with UV/Vis specta. The absorbance peak at 520 nm was observed in all samples after initial red tint through the characteristic wine-red color of gold nanoparticles in the 10-100 nm size range. The AuNP formation was visually observed after 6 hours of incubation. The reaction continued until completion at 8 hours and monitored over the course of 24 hours with TEM images (FIGS. 1a and 1b). FIG. 1c shows the increase of absorbance at 520 nm with time and the corresponding change in color can be observed in FIG. 1d. Particle formation was not observed when dextrin, pH adjustment, or sodium carbonate was excluded from the synthesis.

Figure 2A:
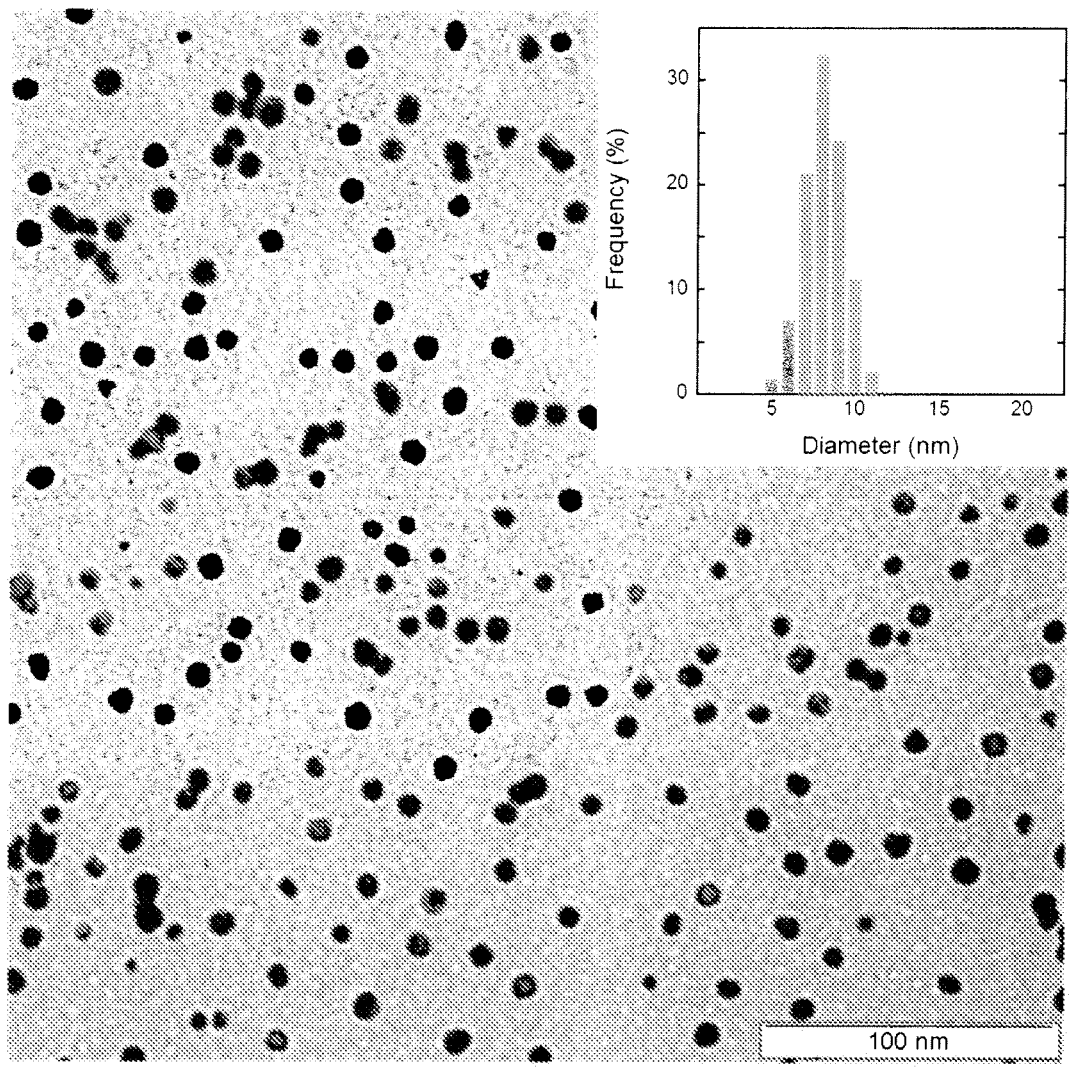
FIGS. 2a-2c are TEM images of AuNPs generated at 50° C. during 24 hours. Insets show the size distribution for each sample. Dextrin concentrations were (a) 20.0 g/L, (b) 10.0 g/L and (c) 2.5 g/L (scale bars for all three TEM images: 100 nm).
Figure 2B:
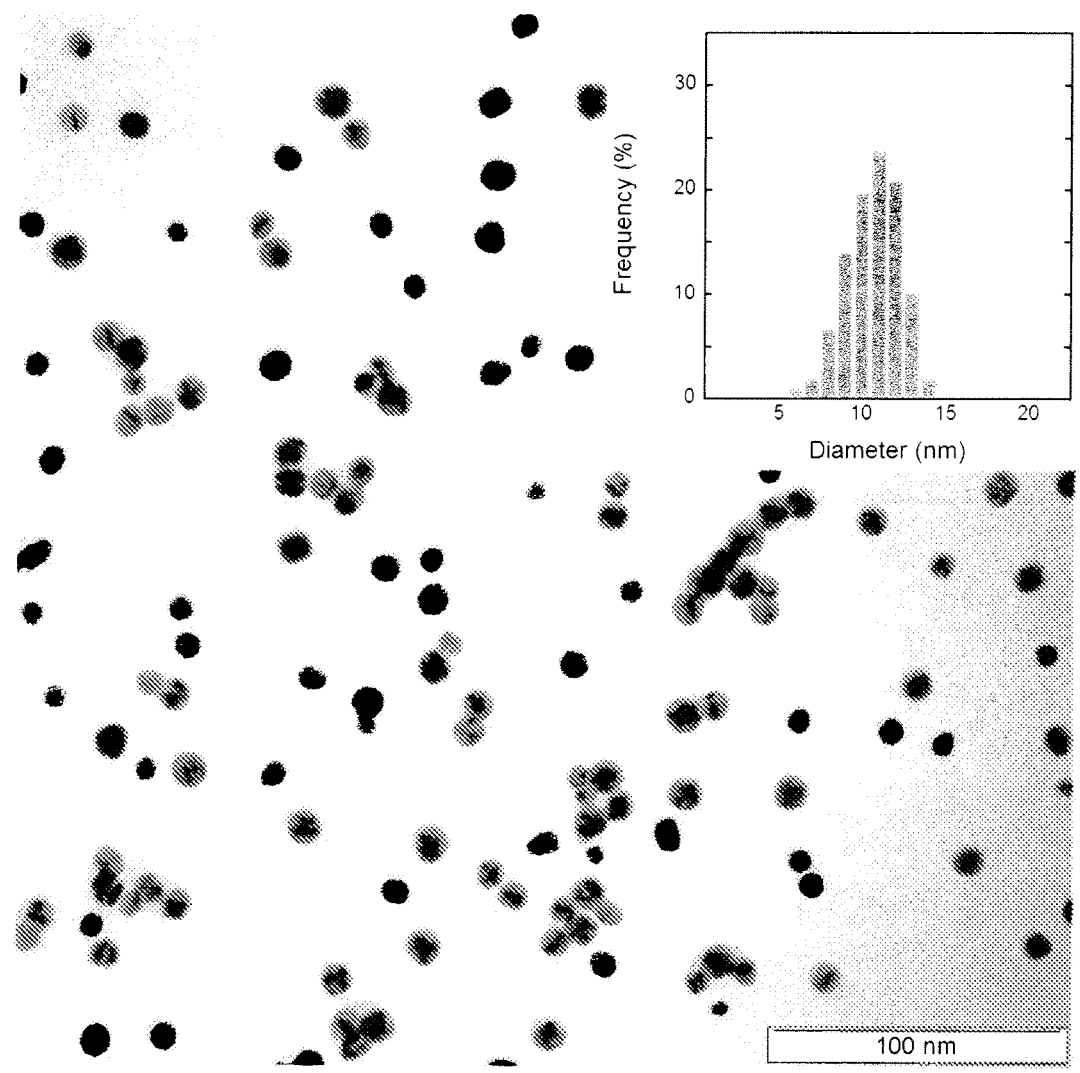
Figure 2C:
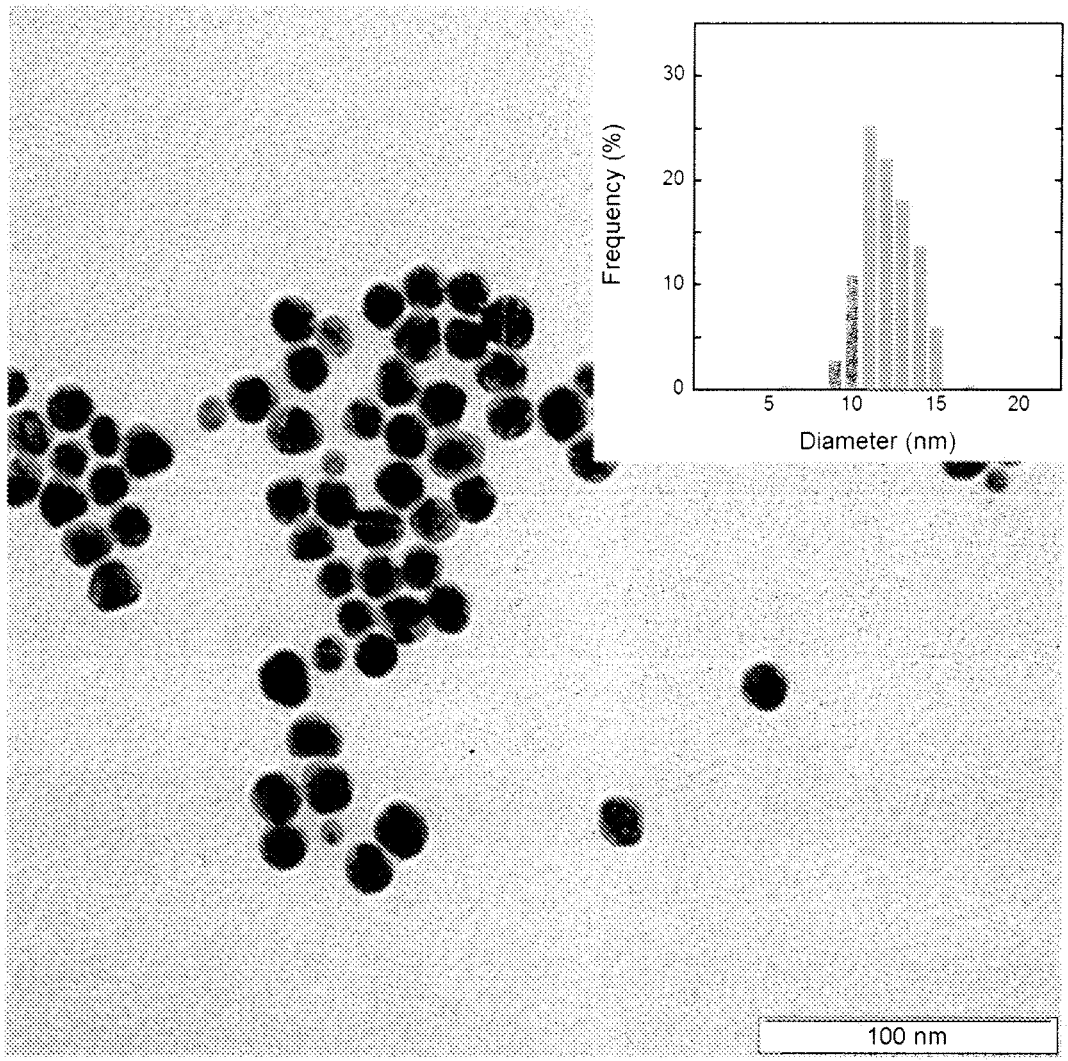
Figure 2D:
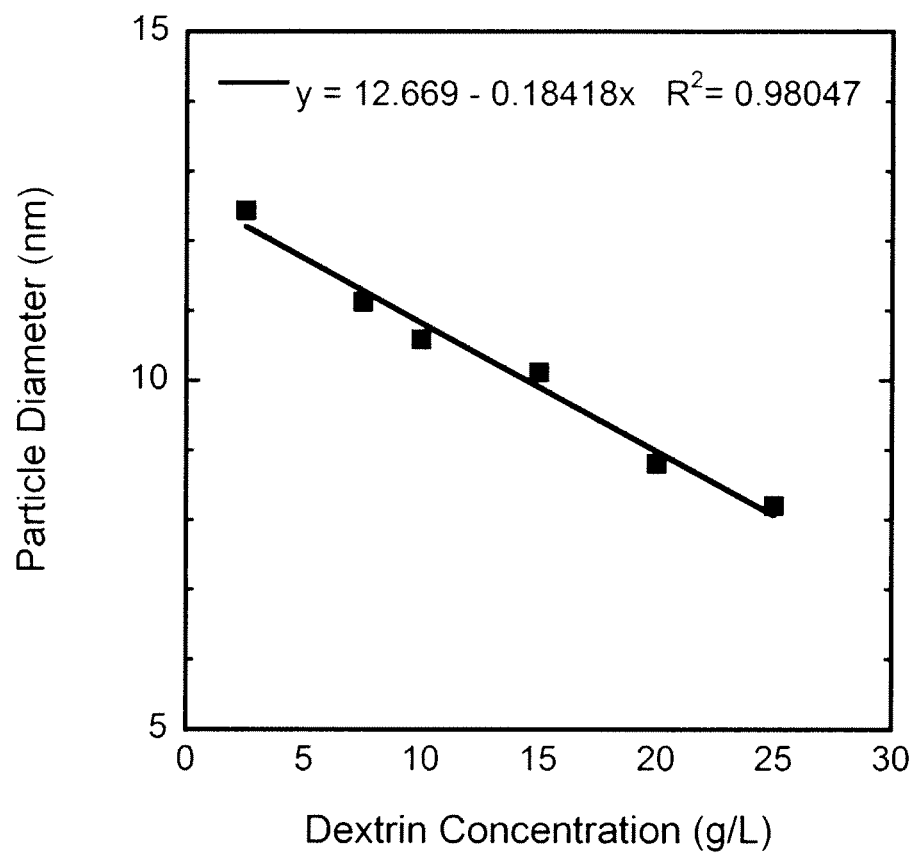
FIG. 2d illustrates the average final AuNP size as a function of initial dextrin concentration.

Effect of Dextrin Concentration:

The ratio of capping agent to particle concentration is a commonly varied factor to control the final size of the particles. The concentration of dextrin was varied from 2.5 g/L to 20.0 g/L to explore the effect of dextrin concentration on particle size. The final size of particles was determined using TEM images (FIGS. 2a-2c). It was observed that the particle diameter decreased with increasing dextrin concentration. Particle sizes were 8.6 nm±1.2 nm, 10.6 nm±1.6 nm, and 12.4 nm±1.5 nm (expressed as a mean+/- one standard deviation of a normal distribution) for 20.0, 10.0, and 2.5 g/L dextrin concentrations, respectively. FIG. 2d shows a linear relationship between dextrin concentration and particle size for 2.5 to 20.0 g/L of dextrin.

The initial yellow color from the $HAuCl_4$ solution changes to clear with the addition of sodium carbonate for pH adjustment. The time required to change from colorless to red decreased with increased initial dextrin concentration. Initial particle formation was observed within 5 hours at 2.5 g/L of dextrin, and within 1.5 hours for 20.0 g/L of dextrin indicated by the wine red color, which became more intense as the reaction completed. UV-Vis spectral data (not shown) were used to monitor the reactions for completion. All dextrin concentrations between 5.0 and 20.0 g/L showed completion at 6 hours, with 2.5 g/L showing completion at 24 hours.

The size and production rate appear to be controlled by dextrin concentration. Polte et al. (2010) proposed a four step generation model for citrate-coated AuNPs. Without wishing to be bound by any particular theory, it appears that alkaline dextrin system presented here appears to follow a similar mechanism, that is, from (1) reduction, (2) stabilization, (3) exchange (slow growth phase), and finally to (4) capping (fast growth phase). Steps 1 and 2 could be carried out by the sodium carbonate reducing a form of $[AuCl_4]^-$, $[AuCl_3OH]^-$, $[AuCl_2(OH)_2]^-$, $[AuCl(OH)_3]^-$ or $[Au(OH)_4]^-$ to $Au^0$, the degree of hydroxyl coordination being dependent on pH. In the early steps, the oxidized carbonate would be stabilizing the initial AuNP instead of the citrate molecule. As the reaction proceeds into the slow growth phase, step 2-3, the exchange of carbonate for dextrin occurs which explains the extended time it takes for the growth phase to complete, as observed in the transition from the purple tint and the initial red color. Once the system enters step 4, fast growth, dextrin is believed to be the sole capping agent and the disassociation allows for auto-catalytic growth and rapid re-association of free dextrin molecules. This growth stage in the alkaline generation methodology is estimated to be the 30-60 minute time window for the purple tint to transition to the wine red color. Changes in dextrin concentration for this system may explain why the rate increased and the size decreased with higher concentration. The smaller particle sizes result when higher amount of capping agents are used. A greater capping agent concentration can cover greater surface areas and generate smaller sized particles (Wang and Yang 2006). The increased rate of generation may be explained by either bulk interaction or association. In a higher concentration system, dextrin may interact with the carbonate on the gold surface promoting faster carbonate disassociation. As the carbonate disassociates, greater concentrations of free dextrin undergo surface capping more rapidly.

Figure 3:
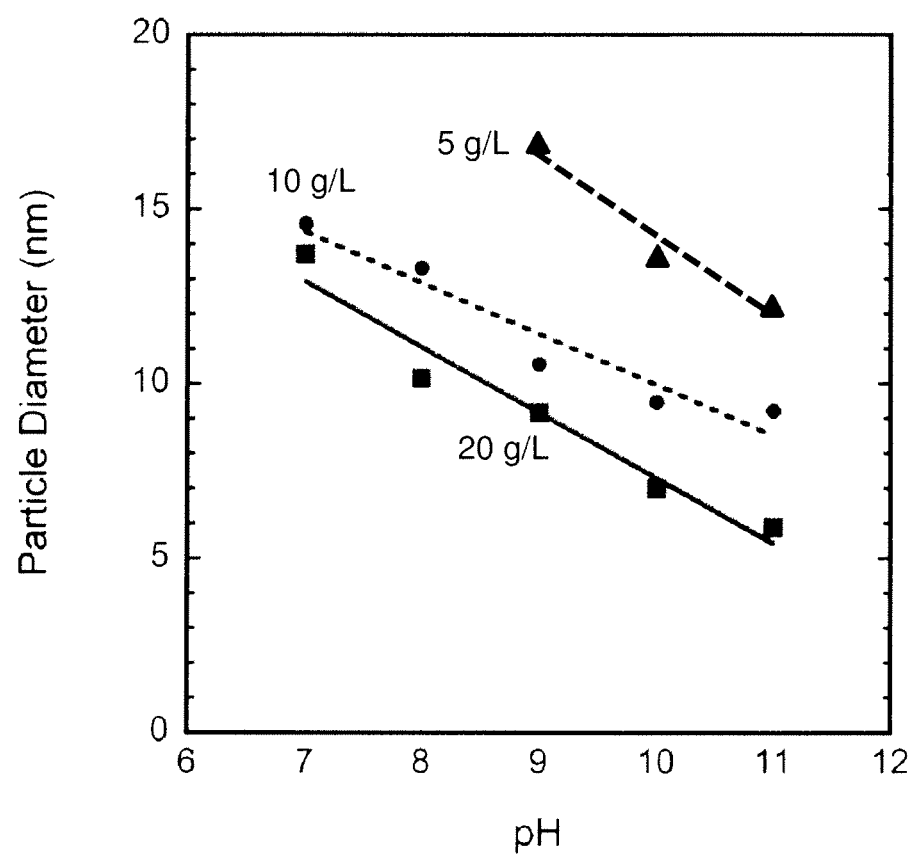
FIG. 3 is a graph illustrating AuNP particle size versus pH and dextrin concentration.

Effect of pH:

Recent reports of sodium hydroxide induced particle formation (Zhou et al. 2009) suggest that hydroxyl ions can reduce $Au^{3+}$ into $Au^0$, but do not participate in the capping and stabilization of the AuNP. The pH of the reaction was varied from 3 to 11 to explore the effect of pH on particle formation. The pH reactions were conducted at 10.0 g/L dextrin and 2 mM $HAuCl_4$, and incubated for 24 hours at 50° C. Below pH 7, no particle formation was observed after 24 hours, and at pH 11 the reaction proceeded nearly instantly at room temperature. A negative control with $[AuCl_4]^-$ at pH 9.0 and without dextrin did not yield particle formation after 24 hours nor did a solution only adjusted with sodium hydroxide. The use of sodium hydroxide to adjust the pH instead of sodium carbonate produced a purple-black precipitate with some metallic gold film forming on the glassware. AuNPs with average particle diameters from 7.0±1.2 nm to 16.8±2.3 nm were generated within the biological range of pH 7-10 in 24 hours. FIG. 3 shows the average sizes obtained with different pHs sodium carbonate adjusted and dextrin concentration during generation.

The generation of AuNPs at pHs in the range of 7.0-11.0 with generation times from 1 minute to 6 hours, allows other biological materials, such as DNA, to potentially be used as capping agents, with the possibility of shortening the time or number of steps currently required for DNA functionalization. The faster reaction times and smaller particle sizes observed could be explained by a similar mechanism to the four step synthesis proposed by Polte et al. (2010). The increased carbonate concentration may cause faster and more complete nucleation of the $[AuCl_4]^-$, $[AuCl_3OH]^-$, $[AuCl_2(OH)_2]^-$, $[AuCl(OH)_3]^-$ or $[Au(OH)_4]^-$ species. This faster rate reduces the available gold that would be used in steps 3 and 4 for growth. By increasing the initial concentration of the reduction agents, faster nucleation may explain the observed increase of the reaction rate and observed decrease in the particle sizes. Reactions less than pH 7 did not occur with sodium carbonate as the reduction agent. Carbonate has a pKa 6.33 and 10.35. At pH 9 the predominant form is bicarbonate, at pH 11 slightly more than 65% is carbonate, and at pH 7 virtually no carbonate exists. Carbonate is a more reactive reducing species than bicarbonate and slow carbonate-bicarbonate equilibrium could account for the longer generation times encountered. This could explain the rapid reaction rate at pH 11, where the carbonate is the predominant specie in equilibrium and why at pH lower than 7 no reaction occurs as nearly no carbonate exists in equilibrium.

Figure 4:
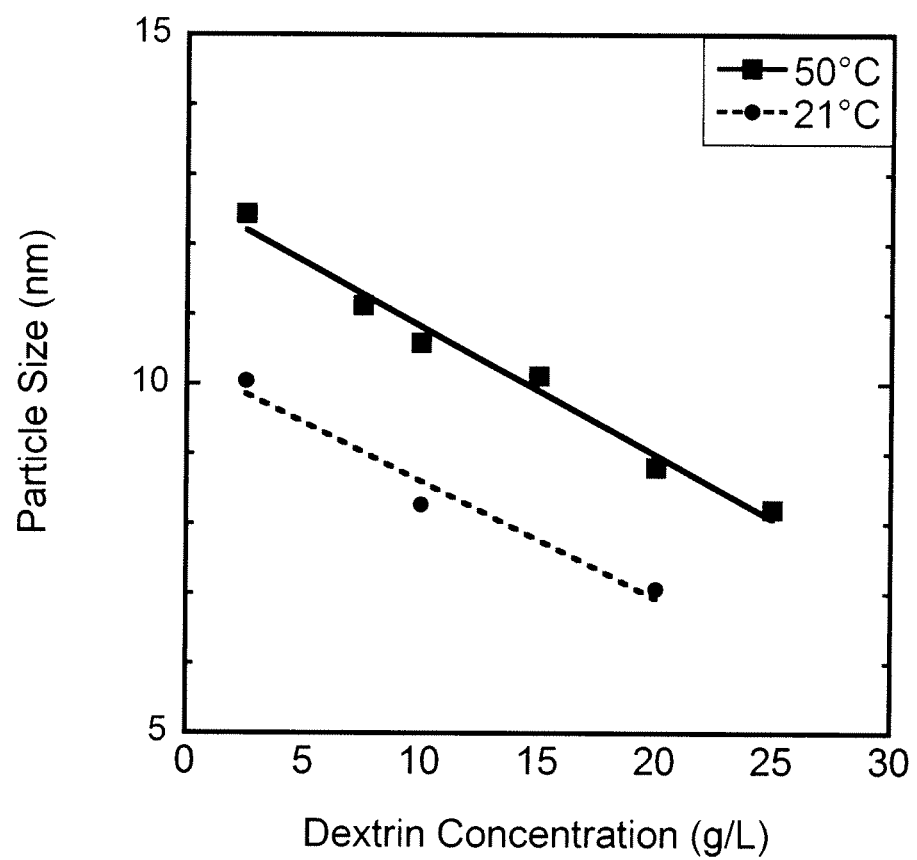
FIG. 4 is a graph illustrating AuNP particle size versus dextrin concentration after 24 hours at two generation temperatures.

Effect of Temperature:

The effect of temperature on the AuNP synthesis was explored to determine if the reaction rate or particle size was influenced by this factor. Reactions were carried out at 50° C. and room temperature (21° C.) during 24 hours for concentrations of 20.0 g/L, 10.0 g/L and 2.5 g/L of dextrin. At 50° C. particles were generated in all dextrin concentrations after 6 hours. At room temperature, particle formation using 10.0 g/L of dextrin was complete after 48 hours; using 2.5 g/L of dextrin particle formation was approximately 70% complete after 48 hours. Reaction completion was based on absorbance data (not shown). FIG. 4 shows the average particle diameter plotted against initial dextrin concentration at varying temperature. The particle size is affected by both temperature and dextrin concentration. The average particle diameter increased with increasing temperature. Particle formation was observed at 100° C. in three minutes and completed after 7 additional minutes on the bench top. The particles generated at 100° C. were not measured for this study as the reaction temperature was non-favorable for the stability of other possible biological capping agents.

The initial reactions are clear after sodium carbonate adjustment, suggesting that nucleation has occurred and removed the $Au^{3+}$ in free solution (Kimling et al. 2006). Increases in generation temperature may increase the rate of disassociation of the capping molecule, dextrin in this example. With higher temperatures, the partially uncapped AuNP is more likely to interact with free gold from solution, step 3 as suggested by Polte et al. (2010), and result in a faster growth. A lower temperature reduces the speed of growth in step 3 and the reaction may not be fully completed, explaining the incomplete reaction at room temperature. This control of size and growth rate through temperature variation is expected to be a promising method for functionalizing the AuNPs during synthesis.

Stability:

The dextrin coated gold nanoparticles were stable for more than six months at room temperature (21° C.) without protection from light. The AuNPs were sensitive to low pH conditions, and when the system was titrated to pH 3.5-4.0, a quick change in color was observed to dark purple suggesting aggregation. Complete precipitation of the particles occurred after 12 hours at room temperature. After the color change, a deep purple particulate formed and precipitated. This insoluble precipitate could not be resuspended by pH adjustment or sonication. Dextrin is an oligosaccharide of D-glucose, and D-glucose has a pKa ~12.3. The change in pH reverses the charge of the dextrin capping material thus eliminating the electrostatic interaction between dextrin and the AuNP core. When the particles were pelleted and dried, the resulting pellet could not be resuspended suggesting electrostatic interactions in the aqueous medium are required for stability.

Figure 5:
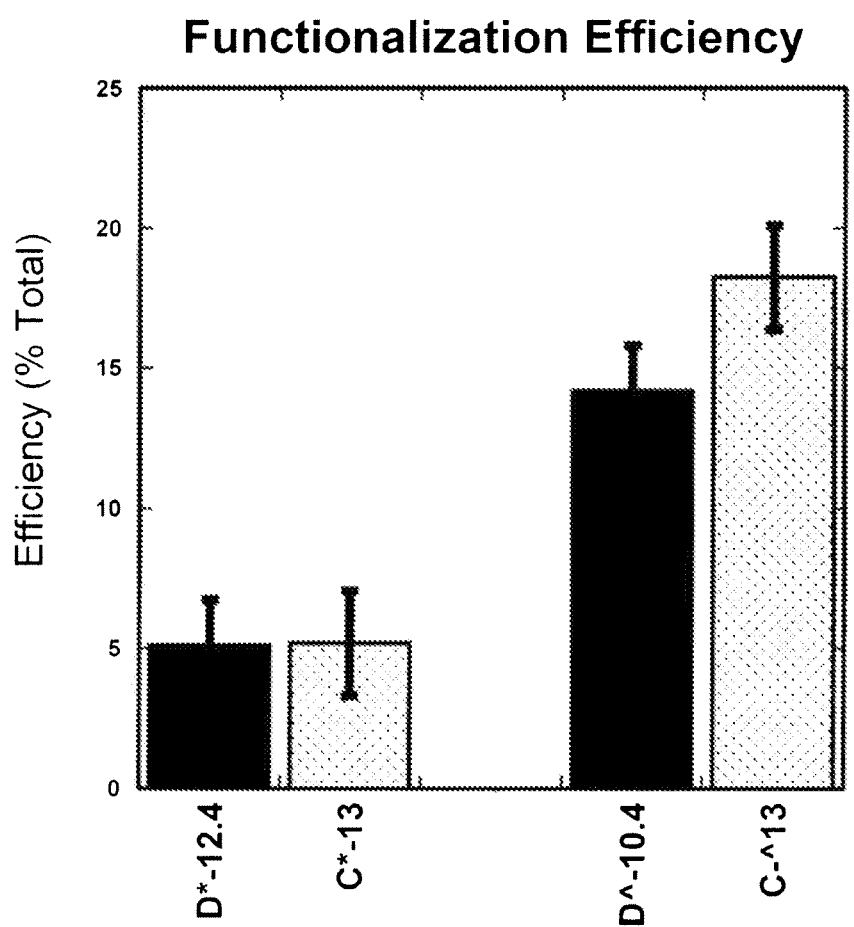
FIG. 5 is a graph illustrating comparative capping efficiencies (percentage of captured fluorescence) of 12.4 nm and 10.4 nm dextrin AuNPs versus 13.0 nm citrate AuNPs. The observed capping efficiency of 12.4 nm dextrin coated AuNPs and 13.0 nm citrate AuNPs was the same (left). A lower capping efficiency was observed when the dextrin AuNPs (10.4 nm) were smaller than the citrate AuNPs (13.0 nm) (right). Graph legend: D=dextrin capping agent; C=citrate capping agent; * and ^ indicate separate trials.

Functionalization:

The capping ligand exchange on citrate generated AuNPs for thiolated-DNA oligonucleotides is one of the more common attachment techniques (Hill and Mirkin 2006). The dextrin coated AuNPs were functionalized as described with thiolated DNA in Hill and Mirkin (2006) and compared against standard citrate reduced AuNPs. Dextrin AuNPs generated at 2.5 g/L dextrin (size: 12.4 nm) and 10.0 g/L dextrin (size: 10.4 nm) were evaluated for ligand exchange capabilities. Both sizes of dextrin coated particles were successfully functionalized with thiol-DNA-6-FAM oligonucleotides. The functionalization results are shown in FIG. 5.

Direct fluorescence measurement of the 6-FAM is limited because the AuNP core quenches the signal. To measure the attached fluorophore, the DNA-6-FAM was ligand exchanged a second time with DTT to release the thiol-DNA-6-FAM. The recovered fluorescence after the second ligand exchange with DTT comes from the DNA attached to the AuNP cores and demonstrates successful functionalization. The citrate AuNPs were treated with the same ligand exchange procedure. The functionalization efficiency of both sizes of dextrin AuNPs was comparable to the citrate AuNPs. After ligand exchange and release, the citrate AuNPs show greater capping efficiency only when compared to the 10.4 nm dextrin AuNPs (77% of the citrate signal was recovered). The lower fluorescence recovered with the smaller particles was expected due to less available surface area for attachment (approximate 69% of the citrate particle surface area). The functionalization procedure is based on molar concentration, and smaller particles have less surface area for DNA attachment. For the 12.4 nm dextrin AuNPs, the mean capping efficiency is equal to the citrate AuNPs, where the dextrin particles have approximately 90% of the available surface area compared to the 13.0 nm citrate particles. With comparable DNA capping efficiencies, the dextrin AuNPs can be used as an alternative to citrate AuNPs for DNA applications. Another potential application of dextrin AuNPs is the exploration of simultaneous generation and functionalization, greatly reducing the functionalization time of current methodologies.

Proposed Mechanism of Generation:

The AuNP generation process observed with the dextrin and sodium carbonate system shows similarities with the citrate four step AuNP mechanism described by Polte et al. (2010). The initial nucleation (step 1) may be occurring during the pH adjustment when the solution turns from yellow to clear, with sodium carbonate being the reduction agent. As the reaction is allowed to continue, a purple-black tint forms similar to the aggregation and slow growth steps (steps 2-3) of the mechanism proposed by Polte et al. (2010). The growth phase (step 4) is observed during the 30-60 minute window where the solution initially turns from the purple tint to a red tint and then to the deep wine red, characteristic of the AuNP reaction.

Figure 6:
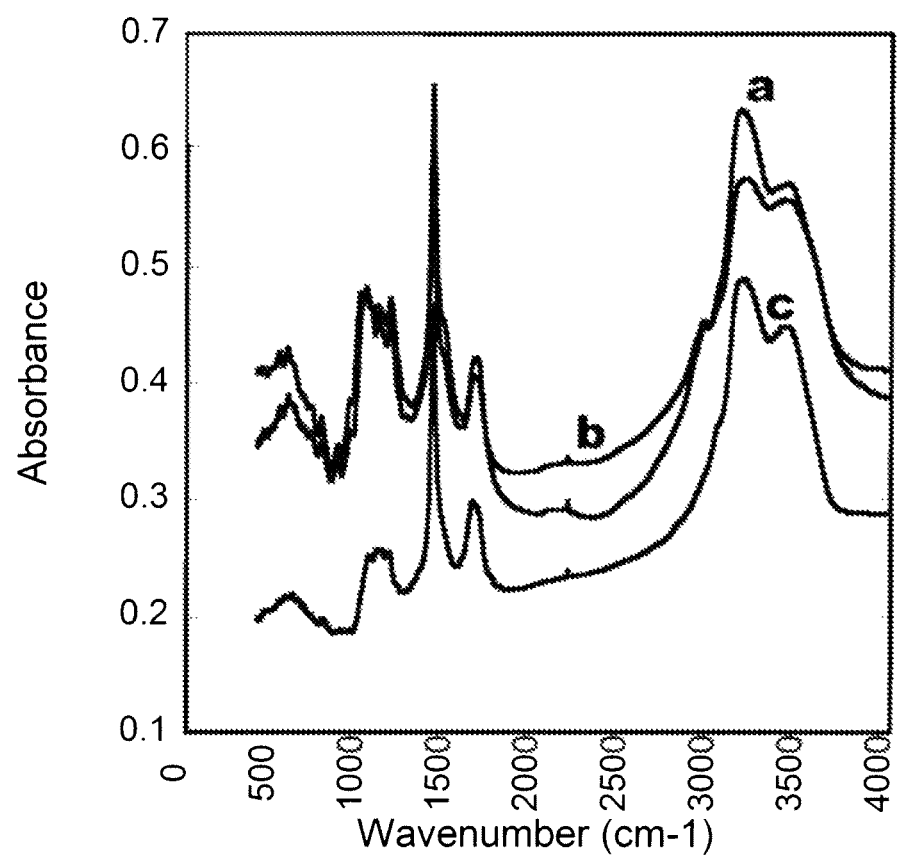
FIG. 6 is a graph illustrating the FTIR analysis of the dextrin capping agent at different points in the synthetic process: (a) stock dextrin as received from manufacturer; (b) autoclaved dextrin solution at 20.0 g/L; and (c) recovered capping dextrin after particle generation.

Data from FTIR suggest that the capping is accomplished by non-oxidized dextrin. There are no characteristic carboxylic acid absorbance peaks at 1714 $cm^{-1}$, 1414 $cm^{-1}$, or 1294 cm$^{-1}$ (FIG. 6) suggesting that the capping agent is not a dextrin with an aldose, ketose or a carbonate molecule. The generated AuNPs were adjusted to pH 4 to remove the charge on the dextrin. The pH 4 AuNP solution was agitated with chloroform to remove the unprotected gold. The dextrin remained in the water phase and the AuNP formed a solid black precipitate at the phase boundary between water and chloroform. The dextrin-containing water phase was used for FTIR analysis. The stock dextrin (FIG. 6a), autoclaved dextrin (FIG. 6b), and recovered dextrin (FIG. 6c) all have similar FTIR peaks. Stock dextrin is a mixture of various chain lengths of repeated glucose sub-units which may allow the efficient AuNPs capping. The AuNP size distribution may be a result of the range in dextrin chain lengths (see histograms in FIGS. 2a-2c).

Summary:

The dextrin technique generated particles with a diameter between 5.9 and 16.8 nm±1.6 nm based on dextrin concentration, pH, and temperature. Optimal AuNP synthesis was at 50° C., pH 9.0, 10.0 g/L of dextrin and 2 mM of HAuCl$_4$ and resulted in particles of 10.6 nm±1.6 nm. The particles remained soluble in water and stable for more than 4 months at room temperature. The dextrin capping agent was removed and the particles were functionalized with thiolated ligands (DNA probes).

Dextrin coated particles may be used for many biological applications due to the alkaline pH generation conditions. Alkaline generation of dextrin AuNPs provides size control and a sugar capping agent that can be removed for thiolated ligand exchange. The use of a polysaccharide for capping provides a biocompatible coating for potential in vivo and in vitro use. Finally, the alkaline conditions potentially allow simultaneous synthesis and functionalization procedures.

Example 2—Synthesis of Functionalized Gold Nanoparticles for Tuberculosis Detection This example describes the development of a DNA based biosensor to detect *M. tuberculosis* using thermophilic helicase-dependent isothermal amplification (tHDA) and dextrin coated gold nanopartcles (AuNPs) as an electrochemical reporter. Dextrin coated AuNPs as in Example 1 are used to create electrochemical labels and tHDA is used as an alternative to PCR for the DNA target amplification. The biosensor system is composed of gold nanoparticles (AuNPs) and amine-terminated magnetic particles (MPs) each functionalized with a different DNA probe that specifically hybridizes with opposite ends of a fragment within the IS6110 gene, which is specific to *Mycobacterium tuberculosis* complex (MTC). After hybridization, the formed complex (MP-target-AuNP) is magnetically separated from the solution and the AuNPs are electrochemically detected on a screen printed carbon electrode (SPCE) chip. The obtained detection limit is 0.01 ng/µl of isothermally amplified target (190 bp). This biosensor system can be potentially implemented in peripheral laboratories with the use of a portable, handheld potentiostat.

Tuberculosis (TB) is the world's second deadliest infectious disease (1.7 million people die annually) and it has been identified as a leading cause of death among HIV-positive patients (WHO, 2009). The standard test for TB diagnosis is smear sputum microscopy, which is unable to identify half of the positive TB infections. Smear-negative TB disease is highly common in HIV co-infected patients (Perkins et al., 2006). Among the novel detection methodologies are the nucleic acid amplification tests (NAATs). These have been extensively explored for the rapid detection of *M. tuberculosis*. NAATs have high specificity and sensitivity, and can provide same day results (detection time: from 2-8 h on processed specimens). However, NAATs require highly specialized personnel, expensive equipment, and are used only in proficient laboratories that can afford reference reagents to monitor the assay performance. Therefore, they are suitable for reference and peripheral laboratory implementation, but difficult to use in resource-constrained settings (Palomino, 2005).

Isothermal amplification techniques have been recently developed as an alternative to polymerase chain reaction (PCR) for target DNA amplification and detection without the use of a thermocycler (Gill and Ghaemi, 2008). Thermophilic helicase-dependent isothermal amplification (tHDA) utilizes a thermostable UvrD helicase to unwind the double stranded DNA (dsDNA) and generate single stranded templates that are used for further polymerase amplification (Lixin et al., 2005). The dsDNA separation and amplification are performed at the same temperature (60-65° C.) which makes this technique suitable for development of point-of-care microbial detection systems, since a thermocycler is not required for DNA denaturation (95° C.) and amplification (Jeong et al., 2009). tHDA protocols have been developed for the detection of several pathogens including: *Helicobacter pylori* (Gill et al., 2008), *Clostridium difficile* (Chow et al., 2008), *S. aureus* (Goldmeyer et al., 2008), *N. gonorrhoeae* (Lixin et al., 2005). tHDA has also been used in microfluidic chips with integrated sample preparation and amplification to detect *E. coli* (Mahalanabis et al., 2010) and for the multiplex detection of *S. aureus* and *N. gonorrhoeae* using a microarray on-chip amplification approach (Andresen et al., 2009).

Recently, nanomaterials have been introduced to enhance molecular detection performance. Nanoparticles have been widely used over the last decade in the development of new diagnostic devices, especially quantum dots (ODs) and gold nanoparticles (AuNPs), (Azzazy et al., 2006). Sensitivity enhancement has been achieved with the use of nanoparticles as tags or electrochemical labels. One of the most explored applications of AuNPs in clinical diagnostics is the use of AuNP probes (AuNP-ssDNA probe) for the detection of DNA targets. The unique tunable physicochemical properties of AuNPs, plus their good biological compatibility, conducting capability, and high surface-to-volume ratio make them ideal candidates for electronic signal transduction of biological recognition events in DNA-based electrochemical biosensing platforms (Guo and Wang, 2007).

Nanoparticle Synthesis and Characterization:

The gold nanoparticles were synthesized following an alkaline based methodology as in Example 1 (see also Anderson et al., 2010, incorporated by reference in its entirety). A 50 mL solution of 2.5 g/L dextrin and 2 mM gold chloride (HAuCl$_4$) was adjusted to pH 9 using 10% sodium carbonate and incubated at 50° C. with agitation in the dark for 8 hours. After the reaction was completed, the solution changed from pallid yellow to dark red. The formed AuNPs (average size: 12.5 nm) were characterized using UV-Vis spectrophotometry (UV-VIS-NIR; Shimadzu) and transmission electron microscopy (TEM) (JEOL 100CX). The amine-coated magnetic particles (average size: 1 µm) used in the biosensor system were commercially available (Sigma Aldrich Cat No. I7643-5ML).

tHDA Primers and Hybridization Probes:

The tHDA primers were designed to specifically amplify a fragment of the IS6110 gene which is tuberculosis (TB) complex-specific (forward primer: 5' GAG CGT AGG CGT CGG TGA CAA AGG 3' (SEQ ID NO: 2); reverse primer:

5' GCT TCG GAC CAC CAG CAC CTA ACC 3' (SEQ ID NO: 3); GenBank: AJ242908.1 (*Mycobacterium tuberculosis* IS6110 genes and partial plcD and Rv1758 genes)). Specific fragments within the sequence (130-500 bp) have been widely used for PCR protocols targeting *Mycobacterium tuberculosis* complex (MTC) species (Dalovisio et al., 1996; Fernandez et al., 2009). The tHDA primers were designed considering the optimal conditions for isothermal amplification (IsoAmp II Universal tHDA kit, biohelix). The obtained tHDA product (amplicon) was used as a template for the hybridization assay. Two different DNA probes (capture probe for MPs: 5'-ss-AAA AAA AM AAA GAG CGT AGG CGT CGG TGA-3' (SEQ ID NO: 4) and reporter probe for AuNPs: 5'-GTG CTG GTG GTC CGA AGC MA AAA AAA AAA-ss-3' (SEQ ID NO: 5)) were also designed to specifically hybridize with the fragment generated by the tHDA reaction. All oligonucleotides were evaluated for specificity using the Primer-BLAST program (available from the National Center for Biotechnology Information (NCBI) website). Primers and probes were designed using the Primer3 program (Rozen et al. 2000) and purchased from IDT (Integrated DNA Technologies; Coralville Iowa).

Nanoparticle Functionalization:

The dextrin coated AuNPs (~12.5 nm in diameter) synthesized using the alkaline procedure were functionalized with a thiolated probe (TB 3'thiol; SEQ ID NO: 5) following a common methodology applicable for citrate coated AuNPs ligand exchange (Anderson et al., 2010; Hill and Mirkin, 2006). Briefly, the thiolated DNA probe (5 nmoles) was reduced with DTT and purified using a SEPHADEX column (Nap-5, GE Healthcare). One milliliter of the dextrin coated AuNPs (AU=2 at A 520 nm) was mixed with the purified probe solution. The dextrin molecules coating the surface of the nanoparticles were exchanged for the thiolated DNA probe over a series of salting steps. After ligand exchange the particles were stored under refrigeration until use.

The amine coated MPs (~1 µm in diameter) were functionalized with a secondary thiolated DNA probe (TB 5'thiol; SEQ ID NO: 4) using sulfosuccinimidyl 4-N-maleimidomethyl cyclohexane-1-carboxylate (sulfo-SMCC) as cross linker (Zhang et al., 2009). Briefly, the amine coated MNPs (10 mg) were conjugated with sulfo-SMCC and incubated with the DTT reduced and purified thiolated DNA probe (10 nmoles). After functionalization, sulfo-NHS acetate was used to block the unreacted linker groups on the MP surface. After passivation, the particles were washed and stored under refrigeration until use.

Helicase dependent isothermal amplification (tHDA): A synthetic target ssDNA containing the same oligonucleotide sequence of the IS6110 fragment (190 bp) was used (IDT Technologies). In order to evaluate the primers designed for the isothermal amplification, a commercially available kit for isothermal amplification was used (IsoAmp II Universal tHDA kit, biohelix). The amplification was conducted following the tHDA conditions for one-step 50 µl tHDA reaction (1x annealing buffer II, 4 mM $MgSO_4$, 40 mM NaCl, 3.5 µl dNPT solution, 1 ng synthetic target, 75 nM of each primer, 3.5 µl enzyme mix). The reaction was covered with mineral oil (50 µl) to avoid evaporation. The isothermal amplification reaction was also optimized using individual reactants: 1x thermo pol II buffer (provided with the polymerase), 4 mM $MgSO_4$, 3 mM dATP, 200 uM dNPTs, 20 U Bst DNA polymerase large fragment, 100 ng thermostable helicase, 1 ng synthetic target DNA, 75 nM forward primer (105-F; SEQ ID NO: 2), 75 nM reverse primer (105-F; SEQ ID NO: 3). Both enzymes were purchased from New England Biolabs. The total reaction volume was 50 µl and same volume of mineral oil was added to avoid evaporation (Lixin et al., 2005; Vincent et al., 2004). Both reactions were incubated in a regular heating block for 90 min at 65° C. (Eppendor Thermomixer R). After the reaction, the product was purified using a silica membrane column (Miniellute, Qiagen) to eliminate the remaining primers. The purified product was serially diluted for the hybridization assay.

Figure 7:
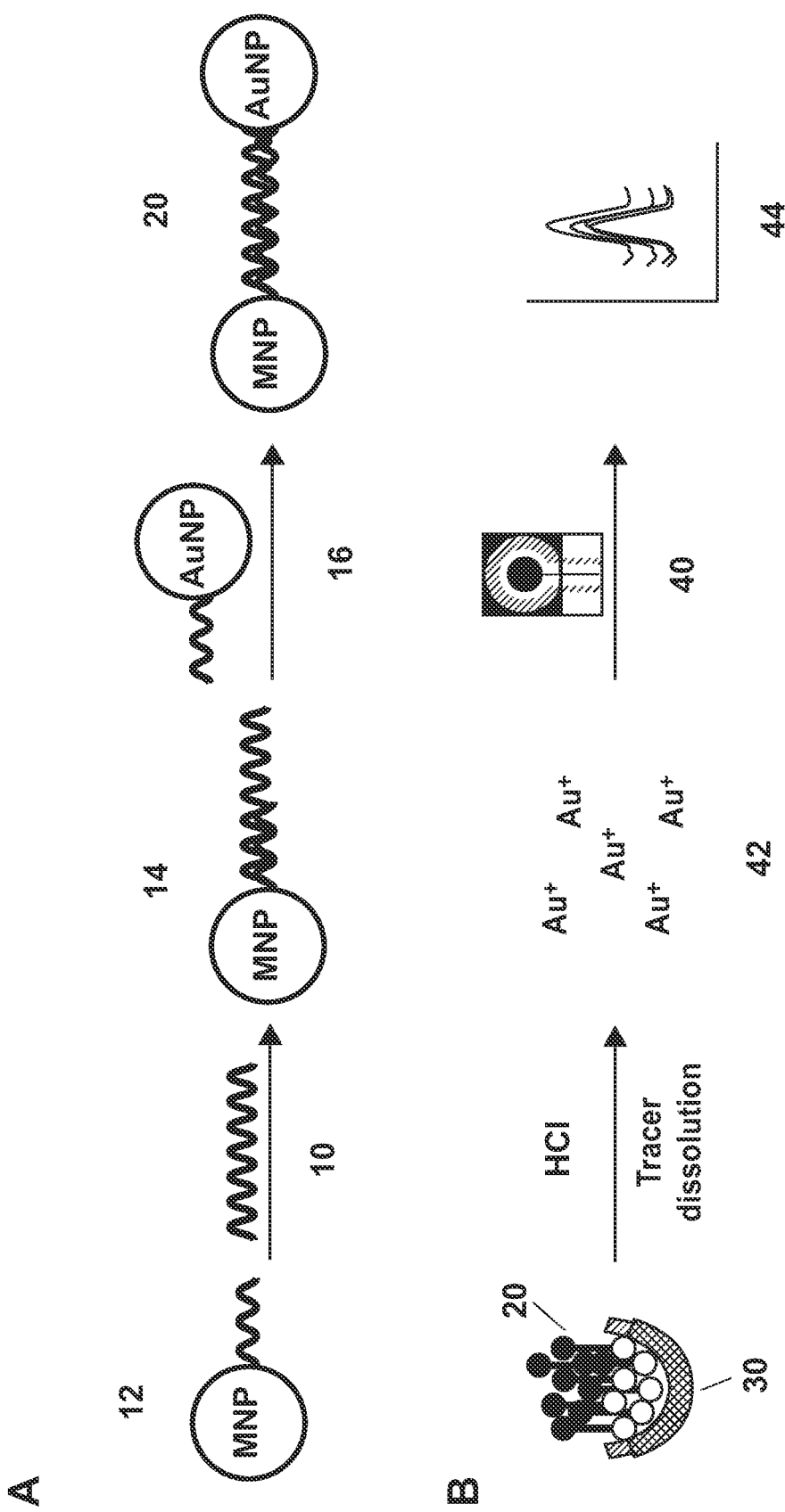
FIG. 7 is a schematic of a target DNA detection system according to Example 2: (A) formation of complex target sandwich (MP-target DNA-AuNP); (B) magnetic separation, metallic tracer ($Au^{3+}$) dissolution and electrochemical detection.

Hybridization assay and electrochemical detection: With reference to FIG. 7, the product obtained from the tHDA (target DNA 10; 10 ng/µL-0.01 ng/µL) was denatured at 95° C. for 10 min and allowed to hybridize with the capture DNA probe (TB 3'thiol; SEQ ID NO: 4) on the MPs (0.8 mg) (MNP with $1^{st}$ DNA probe 12) for 45 min at 44.5° C. with continuous rotation to form a MP-target DNA complex 14. After magnetic separation and several washing steps to eliminate the unreacted target, AuNPs (40 µL) labeled with the reporter probe (TB 5'thiol; SEQ ID NO: 5) (AuNP with $2^{st}$ DNA probe 16) were added and incubated for 2h at 44.5° C. with continuous rotation to form a hybridized sandwich complex 20 consisting of MNP-target DNA-AuNP (Zhang et al., 2009). The sandwich complex 20 was pulled and separated with a magnet 30. After several washing steps to eliminate the non-hybridized AuNPs, the complex 20 was resuspended in 50 µL of water and transferred to a SPCE electrode 40 (Gwent electronic materials, Ltd.) for electrochemical detection (FIG. 7). The SPCE 40 is composed of working (carbon) and reference (silver/silver chloride) electrodes. The solution was allowed to dry onto the carbon electrode for 30 min, and then 50 µL of 1M HCl solution was added to dissolve the AuNPs and generate $Au^{3+}$ ions 42. A constant 1.25 V was applied to the electrode for 2 min to oxidize the gold ions (potentiostat/galvanostat 263A and PowerSuite software, Princeton Applied Research). Differential pulse voltammetry (DPV) was performed from 1.25V to 0.0V (with a step potential of 10 mV, modulation amplitude of 50 mV, and scan rate of 33.5 mV/s) to generate the voltammogram as readout 44 produced by the reduced gold ions on the SPCE (Pumera et al., 2005).

Results—Nanoparticle Synthesis, Characterization and Functionalization:

The dextrin coated AuNPs were characterized using UV-Vis spectra and TEM. Absorbance peaks were obtained at 520 nm which is characteristic of the AuNPs production. The average particle diameter (12.4 nm) was confirmed by the TEM images. In this example, the dextrin-coated AuNPs are incorporated into a biosensor platform.

Figure 8:
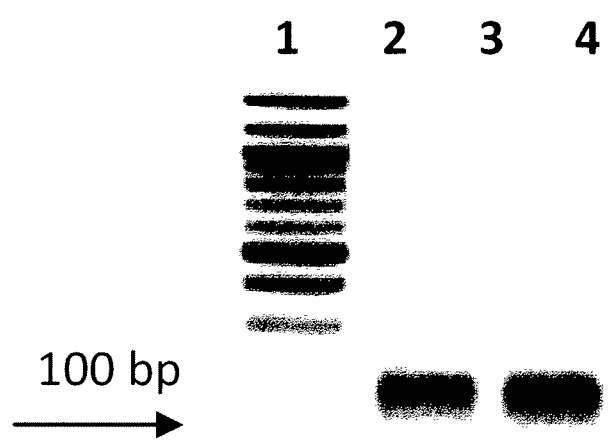
FIG. 8 is an agarose gel electrophoresis of tHDA products for the specific isothermal amplification of a IS6110 fragment using individual reactants (Lane 1:100 bp ladder; Lanes 2 and 3: tHDA amplification fragment using 5 ng of synthetic target (190 bp); Lane 4: Blank).

Helicase Dependent Isothermal Amplification (tHDA):

Successful amplification was obtained using the designed tHDA primers, synthetic target DNA and the tHDA kit following the conditions for one-step reaction (90 min of incubation at 65° C.) (IsoAmp II Universal tHDA kit from biohelix). After the primer evaluation with the commercially available kit, the isothermal amplification reaction was also optimized using individual reactants. Table 1 below shows the parameters used for the tHDA protocol design for the isothermal specific amplification of a IS6110 fragment and the corresponding FIG. 8 shows the successful amplification products (bands) using individual reactants from agarose gel electrophoresis.

TABLE 1 tHDA Parameters for Isothermal Amplification

| tHDA Parameter | TB tHDA (IS6110 fragment) | Optimal |
|---|---|---|
| Amplicon size | 105 pb | 80-120 bp |
| Amplicon Tm | 74° C. | 68-75° C. |
| Amplicon GC % | 63%* | 40% |
| Primer size | 24 b | 24-33 bases |
| Primer Tm | 71° C. | 60-74° C. |
| Primer GC % | 62%* | 35-60% |

*The specific region selected within the IS6110 has high CG content.

Figure 9A:
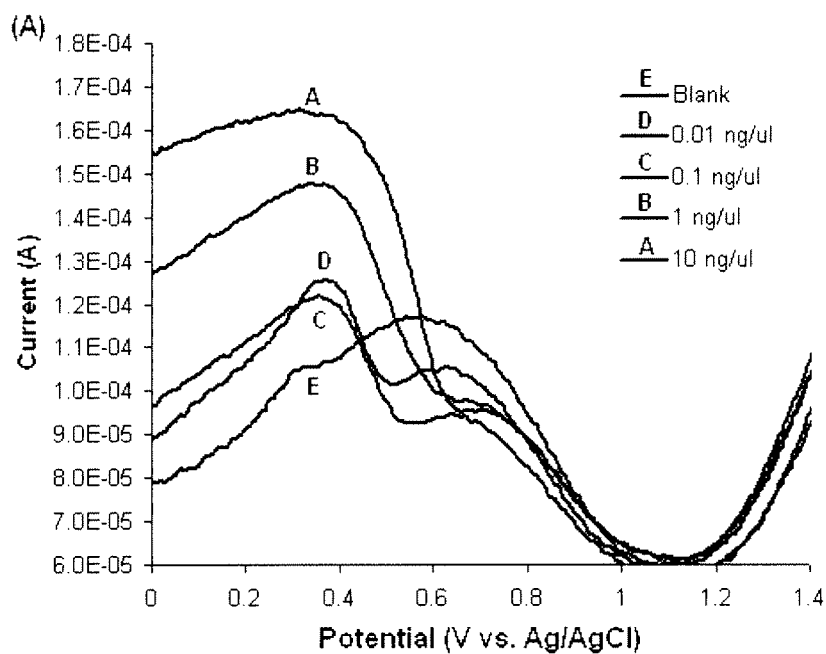
FIGS. 9a and 9b are graphs illustrating the concentration-dependent response of the biosensor system of Example 2. (A) Mean DPV response of sandwich complex (MNPs-target DNA-AuNPs) after hybridization for different DNA target concentrations on SPCE. Each concentration was run in triplicates. The gold reduction peak was observed between 0.30-0.35 V DPV scan from +1.25V to 0V, step potential at 10 mV, modulation amplitude at 50 mV, and scan rate at 50 mV/S. (B) Logarithmic correlation between the target DNA concentration (ng/µl) and the gold reduction peak for three different trials. Each concentration was run in triplicates. The displayed equation corresponds to trial 1, which is the same trial represented in the DPV response plot (A).
Figure 9B:
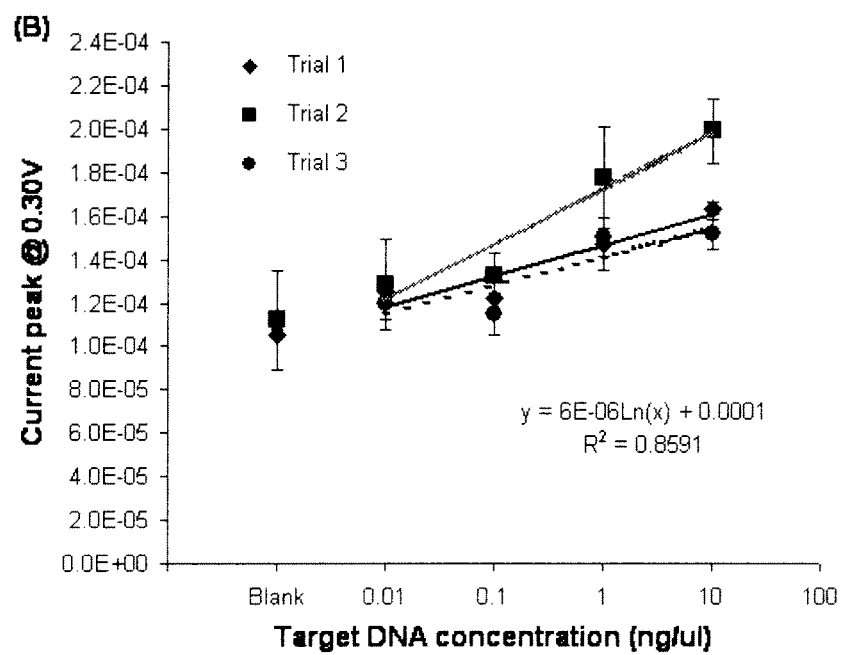

Hybridization Assay and Electrochemical Detection of AuNPs:

Direct oxidation of AuNPs onto the carbon electrode surface was optimized at 1.25 V for 2 min obtaining a reduction peak of gold ions between 0.30 and 0.35 V. FIG. 9a shows the DPV response obtained with different DNA concentrations after hybridization, sandwich complex formation (MP-target-AuNP), magnetic separation and AuNPs dissolution. After the gold was dissolved and oxidized by the acidic solution, the gold ions were reduced between 0.30 and 0.35 V on the SPCE (FIG. 9a). Three separate trials were run using four different DNA concentrations (0.01-10 ng/μl) plus a blank with no target DNA. Each sample was run in triplicates. A linear log-correlation was observed between the target DNA concentration and the gold reduction peak (FIG. 9b). The presence or absence of the target was identified with a detection limit of 0.01 ng/μl. Variability in the peak height was observed in different trials between the two lowest concentrations detected (0.1 and 0.01 ng/μl). This variability may be the result of inter particle distances. At low concentrations, the particles are more dispersed and have more accessible surface area to interact with the acidic solution producing slightly higher reduction peaks. Therefore, the semi-quantitative detection limit obtained using synthetic targets was 0.1 ng/μl.

These results represent the application of dextrin AuNPs as electrochemical labels and the use of tHDA amplification products as DNA targets. In order to evaluate the biosensor functionality, citrate AuNPs using the capture probe according to SEQ ID NO: 5 and MPs using the capture probe according to SEQ ID NO: 4 were used during initial runs with PCR products of the same synthetic target ssDNA corresponding to the IS6110 fragment (190 bp) as targets for the hybridization reaction (data not shown). No difference was observed when using dextrin AuNPs in place of citrate AuNPs as electrochemical labels. This was the hypothesized result since the DTT ligand exchange technique is intended to remove all of the capping agent (i.e., dextrin or citrate, accordingly) on the surface of the AuNP in the oligonucleotide functionalization procedure. The particle's coating molecules are exchanged for thiolated DNA probes and the coating material is liberated to the suspension liquid. After functionalization, the particles are centrifuged and washed to eliminate the supernatant with unreacted materials. Since the elemental gold that is reduced in the electrochemical detection is the same for citrate and dextrin coated AuNPs, there is no effect of the coating material in the detection system.

Summary:

This example describes the development and optimization of a nanoparticle DNA-based biosensor to detect a tuberculosis specific DNA fragment using the electrochemical detection of gold nanoparticles. In order to make the platform more suitable for resource-constrained settings diagnostics, an isothermal amplification reaction was optimized in lieu of PCR which requires a thermocycler. The isothermal helicase dependent amplification was successfully optimized using individual reactants and a regular heating block, which can be replaced with a water bath. The detection time with the proposed platform, including amplification and hybridization is 6 hours; without considering sample preparation (DNA extraction). The main advantages of the proposed platform are that the detection system is not expensive, it can be portable and there is no need of a thermocycler due to the isothermal amplification.

The platform uses alkaline synthesized dextrin coated AuNPs as electrochemical labels. No difference was observed when using dextrin or citrate AuNPs as electrochemical labels in the detection system; nevertheless, the main advantage of using dextrin coated AuNPs is the synthesis. The particles are produced under alkaline conditions (pH 9) and can be synthesized at room temperature. This opens the possibility for bio-molecule (e.g., DNA probes) functionalization during synthesis. The ligand exchange method traditionally used to functionalize citrate AuNPs with DNA probes requires 72 h post-synthesis (Hill and Mirkin 2006).

Example 3—Synthesis of Acid-Functionalized Gold Nanoparticles

This example describes the synthesis of acid-functionalized AuNPs from a dextrin-coated AuNP precursor. The acid-functionalized AuNPs are themselves stable in solution provide a suitable platform for subsequent covalent attachment of a biological probe moiety, for example a DNA probe or antibody.

The method for forming the dextrin-coated AuNPs is similar to that of Example 1. Briefly, a 50 ml aqueous solution of 20.0 g/L dextrin capping agent and 10 g/L galactose supplemental saccharide is added to a 250 ml flack. Chloroauric acid ($HAuCl_4 \cdot 3H_2O$) is added to the reaction mixture as a gold source (final $HAuCl_4$ concentration: 2 mM), and the solution is adjusted to pH 9 using filter-sterile 10% sodium carbonate ($Na_2CO_3$). The reaction flask is incubated in the dark (e.g., covered with aluminum foil) at 50° C. with continuous shaking for 8-12 hours (e.g., overnight) with continuous shaking (e.g., 100 rpm). The result of this process is a stabilized suspension of dextrin-coated AuNPs.

Acid-functionalization is performed as follows. 10 ml of 0.025 M sodium dodecylsulfate (SDS) anionic surfactant is added to the suspension, and the mixture is shaken (e.g., 200 rpm; not stirred, in an embodiment) at room temperature for about 30 minutes. 10 ml of 0.087 mM 11-mercaptoundecanoic acid (11-MUDA; final concentration: 1.24 μM) is then added to the suspension, and the mixture is shaken (e.g., 200 rpm) at room temperature for about 1 hour. The result of this second process is a stabilized suspension of acid-functionalized AuNPs, where the thiol groups of the 11-MUDA are stably adsorbed/bound to the AuNP gold surface, and the outwardly pointing carboxylic acid groups of the 11-MUDA provide hydrophilic groups to stabilize the aqueous suspension and provide chemically reactive groups for the covalent attachment of biomolecules through various methods known in the art (e.g., 1-ethyl-3-(3-dimethylaminopropyl) carbodiimide HCl-mediated reaction between the carboxylic acid groups and amino groups in a biomolecule probe; as in DeLong et al. 2010). In the context of the functionalization methods generally described above, the 11-MUDA represents a binding pair member having a thiol immobilization moiety, a carboxylic acid binding moiety, the two of which are linked with an intervening hydrocarbon (alkylene) chain. Without wishing to be bound by any particular theory, it is believe that a surfactant such as SDS acts as an intermediate capping agent in that it assists in removal of the carbohydrate capping agent and protects/stabilizes the uncharged and unprotected nanoparticle surface until a binding pair member (or immobilization moiety thereof) such as 11-MUDA is able to bind to the surface and re-stabilize the suspension.

Example 4—Synthesis of Gold-Coated Magnetic Nanoparticles

This example provides a gold-coated iron oxide ($Fe_3O_4$) magnetic particle using dextrin as a capping agent that could be used as an extraction and detection tool for pathogenic cells in an electrochemical biosensor system. Other gold-coated $Fe_3O_4$ nanoparticles have been synthesized using citrate as a capping agent. The dextrin-capped gold magnetic nanoparticles produced particles with a stronger spectrophotometric absorption spectrum relative to citrate-capped particles. The gold peak was confirmed using a potentiostat. For comparison, the gold-coated $Fe_3O_4$ nanoparticles were functionalized with oriented antibodies using protein A and non-oriented antibodies through nonspecific adsorption. These were used to magnetically separate *Escherichia coli* O157:H7 from a broth matrix. The protein A and antibody concentrations were varied to determine the most effective concentration for the conjugate to maximize *E. coli* O157:H7 extraction. The nanoparticle-bacteria complex was applied to a modified screen printed carbon electrode. Voltage was applied and current was measured. A current peak was observed at about 0.3 V to about 0.4 V, signifying the presence of bacteria and thus confirming the extraction. The results indicate that dextrin-capped gold magnetic nanoparticles could be used as an extraction and detection tool to report the presence of target bacteria in the biosensor.

The following materials/stock solutions (in distilled/sterile water) were prepared for synthesis of the gold-coated magnetic iron oxide nanoparticles: iron(II) chloride tetrahydrate ($FeCl_2.4H_2O$), iron(III) chloride hexahydrate ($FeCl_3.6H_2O$), hydrochloric acid (HCl; 0.5 M), sodium hydroxide (NaOH; 1.5 M), tetramethylammonium hydroxide (TMAOH; 0.1 M), hydroxylamine hydrochloride ($NH_2OH.HCl$; 0.2 M), dextrin (25 g/L), chloroauric acid ($HAuCl_4$; 0.4 g/50 mL), and sodium carbonate ($Na_2CO_3$; 10% w/v).

The magnetic iron oxide ($Fe_3O_4$) nanoparticles were synthesized with the following procedure. [1] In a 50 mL beaker, dissolve 5.4 g of $FeCl_3.6H_2O$ and 2.0 g of $FeCl_2.4H_2O$ in 25 mL of 0.4M HCl. [2] In a 400 mL beaker, add the iron chloride solution dropwise to 250 mL of 1.5M NaOH to form $Fe_3O_4$ nanoparticles as a black precipitate. [3] Collect the $Fe_3O_4$ precipitate using a magnet. [4] Dispose of supernatant and wash the precipitate twice with sterile water. [5] Wash the precipitate twice with 0.1M TMAOH. [6] Add 250 mL of 0.1M TMAOH to the $Fe_3O_4$ precipitate (for storage as a solution/suspension).

Figure 10:
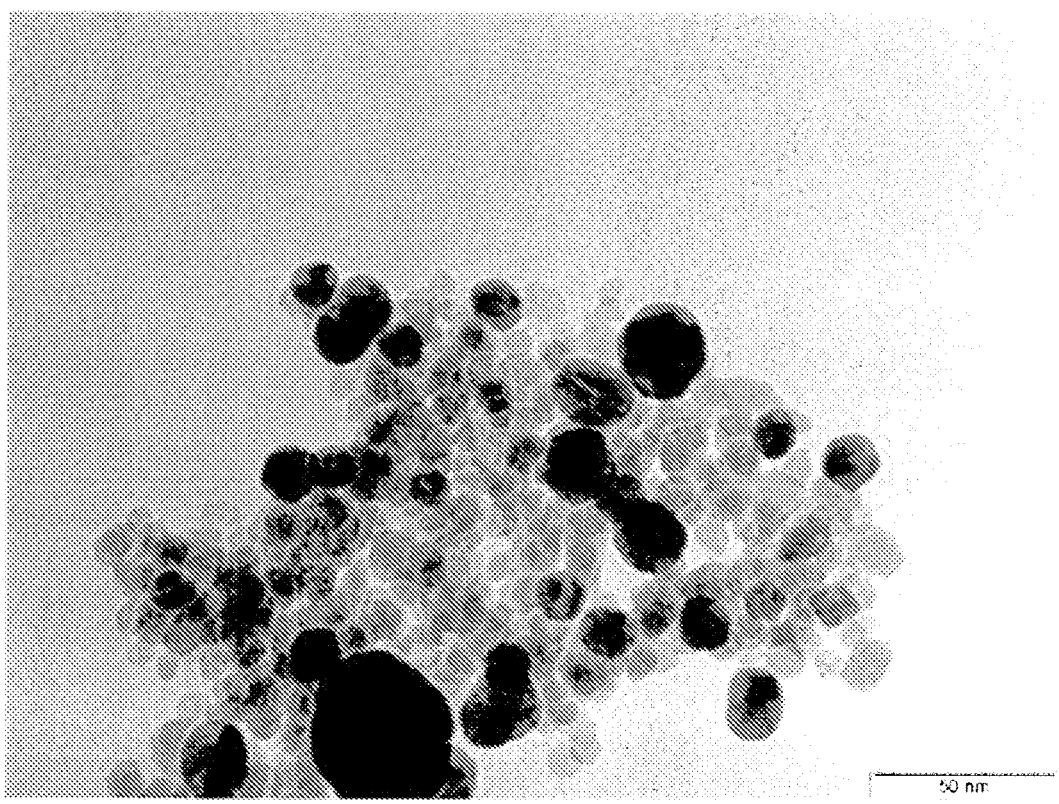
FIG. 10 is a TEM image of dextrin-capped, gold-coated magnetic nanoparticles according to the disclosure (scale bar: 50 nm).

The magnetic iron oxide ($Fe_3O_4$) nanoparticles were then coated with a dextrin-capped gold layer using the following procedure. [1] In a sterile 50 mL tube, combine 17.7 mL sterile $H_2O$, 20 mL of 25 g/L dextrin, and 5 mL of 0.4 g/50 mL $HAuCl_4$. [2] Adjust the solution to pH of 9 using $Na_2CO_3$. [3] Add 3.33 mL of the $Fe_3O_4$ nanoparticle suspension to the dextrin/gold solution. [4] Add 4.8 mL of 0.2M $NH_2OH.HCl$ as an additional reducing agent. [5] Incubate in rotisserie in the dark at 50° C. with continuous rotation for 6 hours. [6] Separate the dextrin-capped, gold-coated $Fe_3O_4$ nanoparticles from the reaction/reduction medium using a magnet (e.g., to separate the magnetic nanoparticle product from non-magnetic gold nanoparticles formed during the reduction process but without a $Fe_3O_4$ nanoparticle core/nucleation site). [7] Discard supernatant and wash twice with sterile water. [8] Repeat steps 1-4. [9] Incubate in rotisserie in the dark at 25° C. with continuous rotation overnight. [10] Separate the dextrin-capped, gold-coated $Fe_3O_4$ nanoparticles from the reaction/reduction medium using a magnet. [11] Discard supernatant and wash twice with sterile water. [12] Store the dextrin-capped, gold-coated $Fe_3O_4$ nanoparticles in 50 mL of sterile water in capped tube. FIG. 10 is a TEM image of example dextrin-capped, gold-coated magnetic nanoparticles formed using this procedure (e.g., showing small particles down to about 5 nm to 8 nm, large particles up to about 30 nm to 50 nm, and an average/median particle size of about 10 nm to 15 nm).

The dextrin-capped, gold-coated $Fe_3O_4$ nanoparticles were then functionalized with anti-*E. coli* O157:H7 antibodies either (i) by direct adsorption/ligand exchange of the antibodies onto the gold surface of the magnetic nanoparticles or (i) by direct adsorption/ligand exchange of protein A/G onto the gold surface of the magnetic nanoparticles followed by incubation with the antibodies to immobilize and properly orient the antibodies on the magnetic nanoparticles. Magnetic separation was used to remove unbound antibodies and the functionalized gold-coated magnetic nanoparticles were re-suspended in phosphate buffered saline (PBS).

Figure 11:
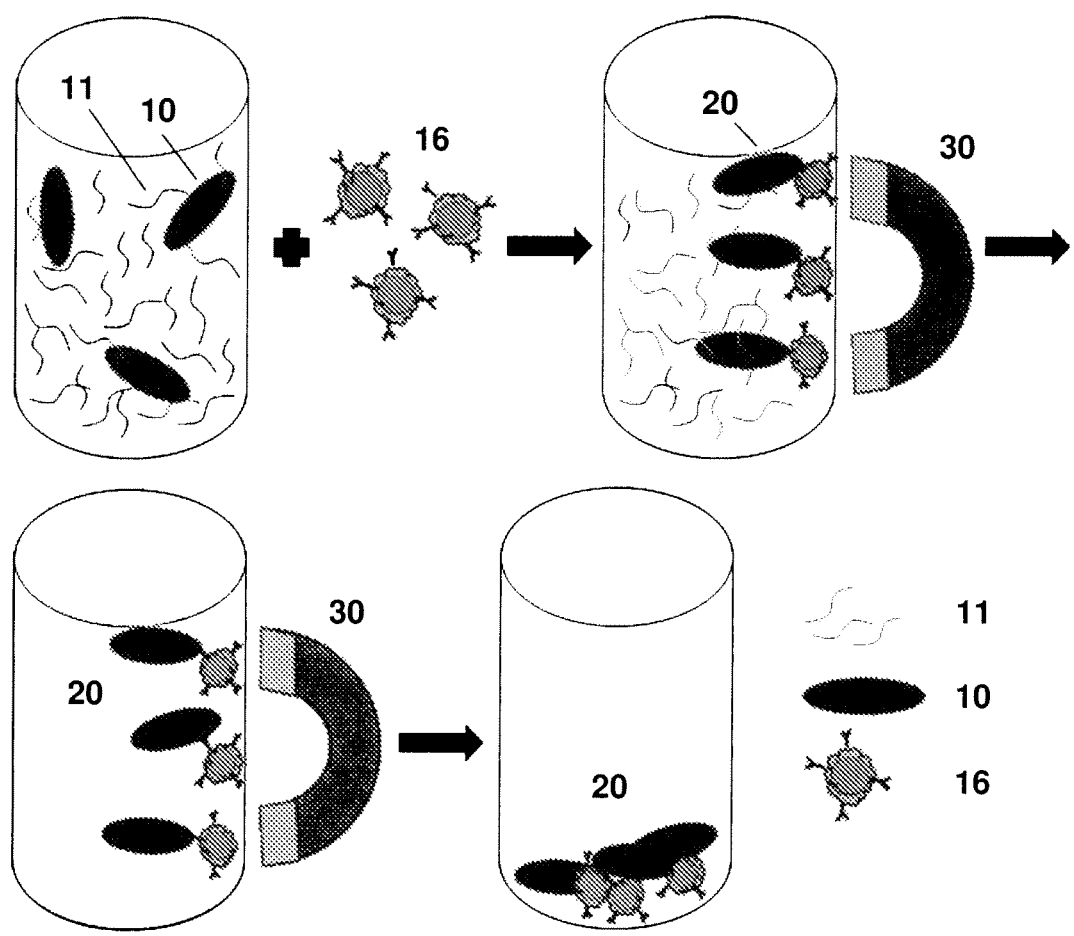
FIG. 11 illustrates a process for capturing and isolating/concentrating an analyte from a sample matrix using carbohydrate-capped, metal-coated magnetic nanoparticles according to the disclosure.

FIG. 11 illustrates a process for capturing, isolating, and concentrating *E. coli* O157:H7 (target/analyte 10) from a broth matrix (sample 11) using the functionalized gold-coated magnetic nanoparticles 16. In particular, *E. coli* O157:H7 extraction was performed by mixing 300 of the functionalized gold-coated magnetic nanoparticles antibody conjugate 16, 30 μl of a bacterial dilution 10/11, and 240 μl of PBS. Solutions were placed in a rotator for 30 minutes in order for the antibodies to bind with the bacteria, forming a complex/conjugate 20. Bacteria that successfully attached to the functionalized nanoparticles as the complex 20 were magnetically separated from unbound bacteria using a magnet 30 (FIG. 11). Conjugates 20 of bound bacteria 10 and the functionalized nanoparticles 16 were washed twice with PBS and re-suspended in PBS. The capture efficiencies of the functionalized nanoparticles 16 were determined by surface plating the bound cells on MacConkey agar and incubating at 37° C. for 24 hours.

Figure 12:
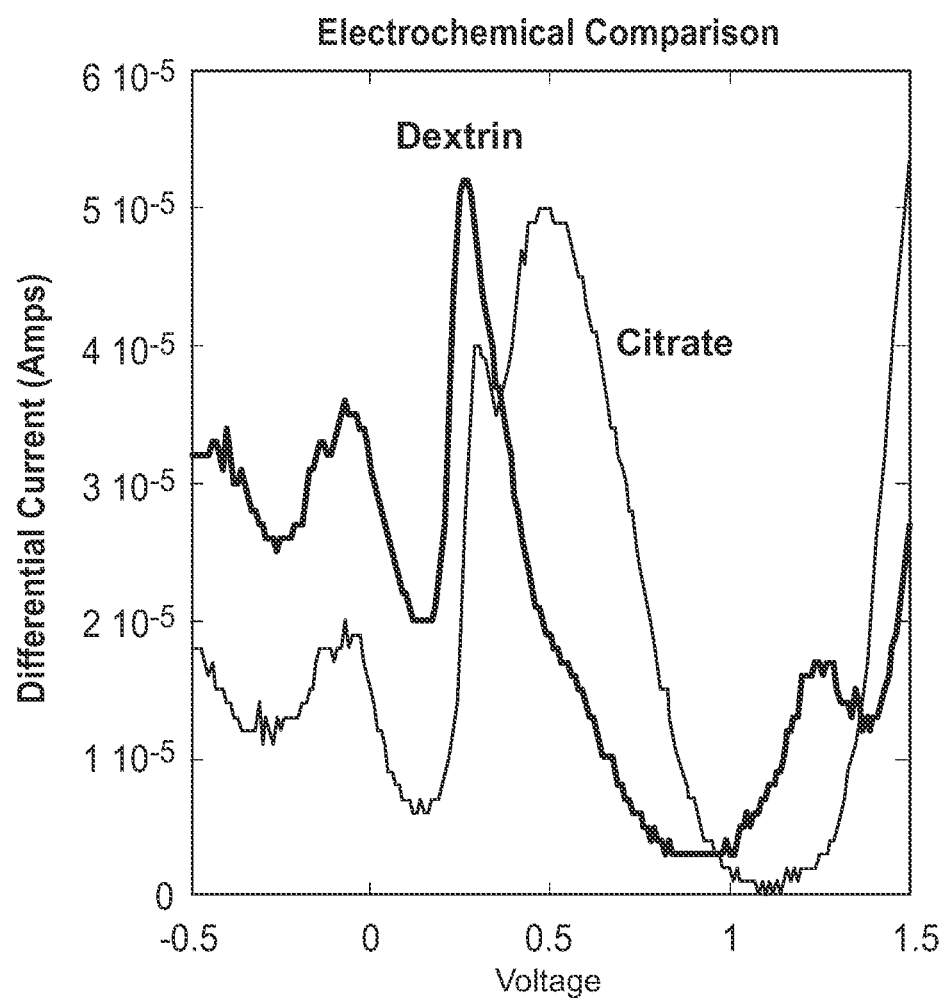
FIG. 12 is a graph presenting an electrochemical comparison in the differential current measured as a function of applied voltage for magnetic nanoparticles coated with either dextrin or citrate.
Figure 13:
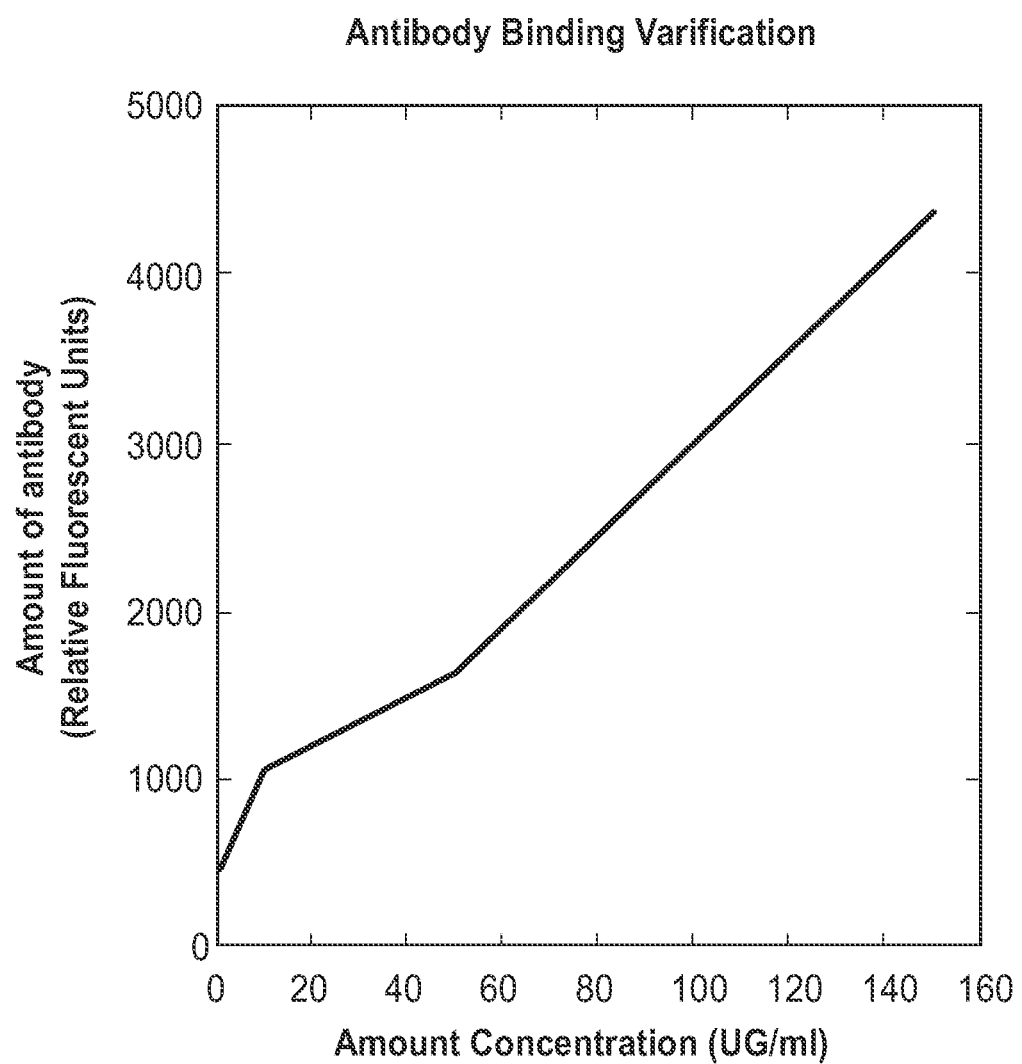
FIG. 13 is a graph confirming the functionalization of dextrin-capped, gold-coated magnetic nanoparticles using a fluorescence-labeled antibody (relative fluorescence units (RFU) of bound/immobilized antibody as a function of antibody concentration).
Figure 14:
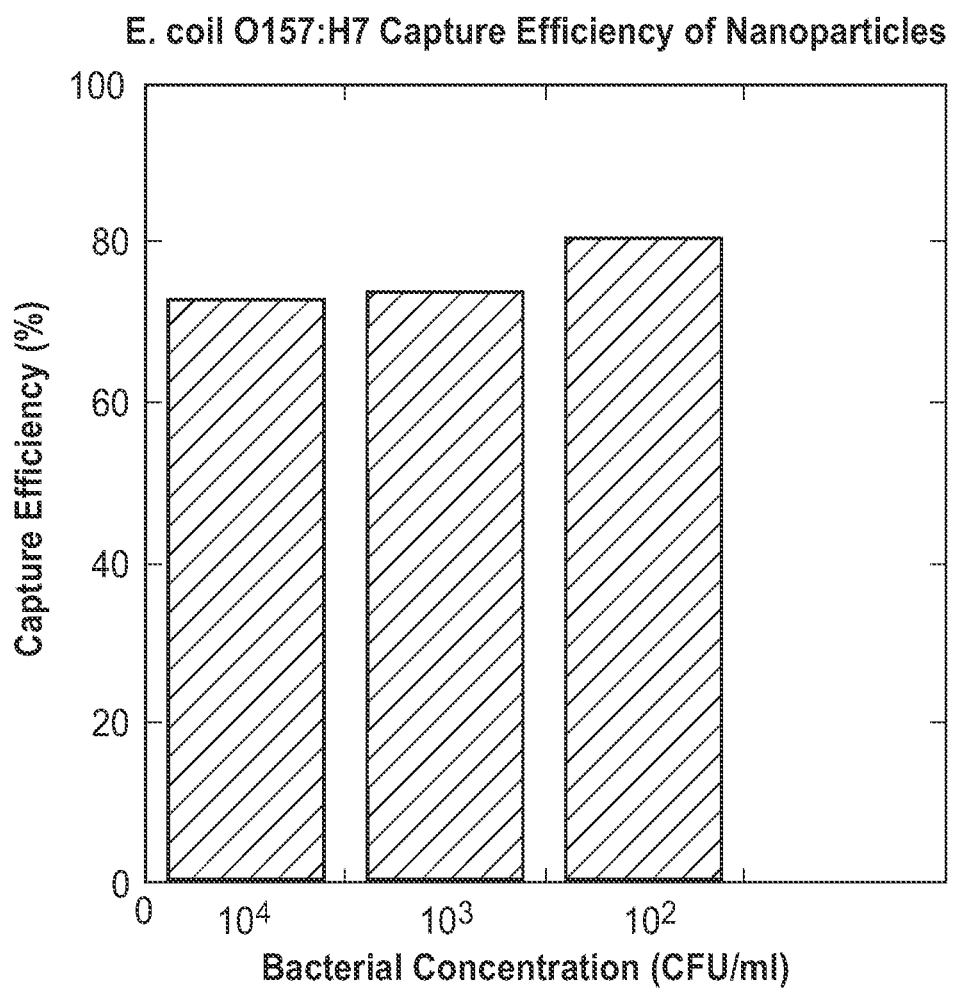
FIG. 14 is a graph illustrating the capture efficiency of antibody-functionalized, dextrin-capped, gold-coated magnetic nanoparticles with respect to an *E. coli* O157:H7 bacterial target analyte extracted from a broth sample matrix as a function of analyte concentration.

Results:

Electrochemical analysis of the dextrin-capped, gold-coated $Fe_3O_4$ nanoparticles produced a higher and sharper electrochemical signal than corresponding citrate-capped, gold-coated $Fe_3O_4$ nanoparticles (FIG. 12). As illustrated in FIG. 12, the dextrin-capped nanoparticles exhibit a relatively narrow electrochemical gold reduction peak at about 0.3 V to 0.4 V, making the particles a suitable platform/electrochemical signal transducer for detection and/or identification of a conjugated target analyte (i.e., the gold reduction peak corresponding to a target analyte detection is not subject to substantial signal interference or overlap from other system components). In contrast, the electrochemical response of corresponding citrate-capped nanoparticles in FIG. 12 exhibits a relatively wide peak over the range from about 0.2 V to 0.9 V, with the additional citrate contribution to the signal making it difficult to reliably and/or accurately detect a gold reduction peak corresponding to the presence of the target analyte (e.g., potentially resulting in false positive, false negative, and/or inaccurate quantitative analyte determinations). Fluorescence-tagged antibodies were used and detected to verify functionalization of the magnetic nanoparticles (FIG. 13). The recovery of bacteria from broth at concentrations ranging from about $10^2$ CFU/mL to $10^4$ CFU/mL was found to have a high extraction/capture efficiency of about 75% to about 80% (FIG. 14).

Example 5—Synthesis of Functionalized Gold Nanoparticles for *E. coli* Detection This example describes the formation and testing of a nanoparticle-labeled biosensor designed for the rapid detection of *Escherichia coli* O157:H7 in broth. Compared to conventional culture plating methods, the biosensor reduced the detection time from 2-4 days to less than one hour without complicated manipulation. Polymer-coated magnetic nanoparticles (MNPs) were conjugated with monoclonal antibodies to separate target *E. coli* O157:H7 cells from broth samples. Carbohydrate-capped gold nanoparticles (AuNPs) were conjugated with polyclonal antibodies and were then introduced to the MNP-target complex to form a sandwich MNP-target-AuNP (e.g., where the AuNP serves as analyte label/electrochemical transducer). By measuring the amount of gold nanoparticles through an electrochemical method, the presence and the amount of the target bacteria were determined. The results showed a sensitivity of $10^1$ cfu/ml with a linear range of $10^1$-$10^6$ cfu/ml. The nanoparticle-labeled biosensor can be used for the rapid detection of infectious agents for public health, biodefense, and food/water safety.

Reagents and Materials: Two kinds of nanoparticles were synthesized: magnetic nanoparticles (MNPs) and gold nanoparticles (AuNPs). Aniline, iron (III) oxide nanopowder, ammonium persulfate, methanol, and diethyl ether were used for the synthesis of the MNPs. Gold (III) chloride trihydrate (Aldrich, Mo.) and dextrin (Fluke, Mo.) were used for the synthesis of gold nanoparticles under alkaline conditions as in Example 1 above. Sodium sulfide, 3-mercaptoacetic acid, lead nitrate and were used for the synthesis of PbS nanoparticles. MNPs were functionalized with monoclonal anti-*E. coli* O157:H7 antibodies obtained from Meridian Life Science, Inc. (Saco, Me.). AuNPs were conjugated with polyclonal anti-*E. coli* O157:H7 antibodies from Meridian Life Science, Inc (Saco, Me.). Protein A from *Staphylococcus aureus* was used as the linkage agent for AuNP and antibody conjugation. TRITON-X100, phosphate buffered saline (PBS), casein, bovine serum albumin (BSA) and sodium phosphate (dibasic and monobasic) were obtained from Sigma-Aldrich (St. Louis, Mo.). PBS buffer (0.01 M, pH 7.4), PBS buffer with 0.05% (w/v) TRITON-X100, phosphate buffer (0.1 M sodium phosphate, pH 7.4), PBS buffer with 0.01% casein, PBS buffer with 0.1% (w/v) BSA were prepared with deionized water from a Millipore DIRECT-Q system.

Bacterial Culture: *E. coli* O157:H7 Sakai strain was obtained from the Nano-biosensors Lab collection at Michigan State University. The colonies from frozen (stored at −70° C.) culture were grown on trypticase soy agar (BD Biosciences, MD) plates. A single colony was isolated and inoculated in tryptic soy broth (BD Biosciences, MD) and grown overnight at 37° C. One milliliter of the liquid culture was transferred to another tube of tryptic soy broth and incubated overnight at 37° C. One milliliter of this liquid culture was transferred to a new tube of broth and incubated at 37° C. for 6 h before each experiment. The serial dilutions of bacterial culture were prepared using 0.1% (w/v) peptone water (Fluka-Biochemika, Switzerland) before each experiment. Viable cells were enumerated by microbial plating on MacConkey agar with sorbitol (BD Biosciences, MD).

Apparatus:

Electrochemical measurement was performed with a potentiostat/galvanostat (263A, Princeton Applied Research, MA) with the software operating system (PowerSuite, Princeton Applied Research, MA) on a computer connected to the potentiostat. The measurement was performed by introducing each sample onto a screen-printed carbon electrode (SPCE) chip (Gwent Inc. England). As similarly described above in Examples 2 and 4, the SPCE chip consists of a working electrode (carbon) and a counter and reference electrode (silver/silver chloride electrode). One hundred microliters of each sample were introduced to the electrode area on the SPCE chip.

Nanoparticle Synthesis: Polyaniline (PANI) coated magnetic nanoparticles were synthesized according to Alocilja et al. U.S. Pat. No. 8,287,810 and U.S. Publication No. 2009/0123939 (incorporated herein by reference in their entireties). Briefly, 50 ml of 1 M HCl, 10 ml of water and 0.4 ml of aniline monomer were mixed in a flask, and then 0.65 g of iron (III) oxide nanopowder were added to the solution to maintain a final $\gamma$-$Fe_2O_3$: aniline weight ratio of 1:0.6. The mixture was put in a beaker filled with ice and sonicated for 1 h. The solution was stirred while it was still on ice. During the stirring, ammonium persulfate (1 g of ammonium persulfate in 20 ml deionized water) was added to the solution slowly for 30 min. The solution was stirred for another 1.5 h. After the reaction, the solution was filtered using 2.5 μm filter paper and washed with 20% methanol. Hydrochloric acid (1 M) was used to wash until filtrate became clear, followed by washing with 10 ml 20% methanol. The filtrate was filtered again using a 1.2 μm filter paper. Twenty percent methanol solution was added to the filter. The HCl and methanol wash was repeated. The nanoparticles on the filter paper were left under a fume hood to dry for 24 h at room temperature and stored in vacuum desiccator after drying.

Dextrin-capped, gold nanoparticles were synthesized under alkaline condition according to the method of Example 1 above. Briefly, 20 ml of dextrin stock solution (25 g/l) and 20 ml of sterile water were mixed in a 50 ml sterile orange cap tube (disposable). Five milliliters of $HAuCl_4$ stock solution (8 g/ml) were then added, and the pH of the solution was adjusted to 9 with sterile 10% (w/v) $Na_2CO_3$ solution. The final volume was brought to 50 ml with pH 9 water. The reaction was carried out by incubating the solution in a sterile flask in the dark at 50° C. with continuous shaking (100 rpm) for 6 h. A red solution was obtained at the end of the reaction. The final concentration of the aqueous suspension of dextrin-capped AuNPs was 10 mg/ml.

Nanoparticle Functionalization: The MNPs were functionalized with monoclonal antibody (mAb) to *E. coli* O157:H7. MNPs (2.5 mg) were suspended in 150 μl of 0.1M phosphate buffer, and sonicated for 15 min. Monoclonal anti-*E. coli* O157:H7 antibody (2.5 mg/ml, 100 μl) was added to the suspension, and hybridized on tube rotor for 5 min. Twenty five microliters of PBS (0.1 M) were added. Then the conjugation was carried on for 55 min on the tube rotor. The MNPs were separated from the solution by magnetic separation, and blocked by adding 250 μl of 0.1M tris buffer with 0.01% casein for 5 min incubation. This step was repeated three times, and the suspension was put on tube rotor for 60 min hybridization at the last time. Finally, the MNPs were magnetically separated and resuspended in 2.5 ml of 0.1 M Phosphate buffer. The MNP-mAb conjugate was stored at 4° C. before use. In a different study (not shown), the MNP was validated in about 40 related *E. coli* O157:H7 strains and 30 unrelated bacterial strains with an inclusivity of about 94%.

Gold nanoparticles were conjugated with polyclonal antibody (pAb) to *E. coli* O157:H7 through a protein A linkage. Two hundred microliters of 5 mg/ml dextrin-capped AuNPs were put into a 2 ml microcentrifuge tube and sonicated for 10 minutes. Then the suspension was centrifuged for 6 min at 13,000 rpm. The supernatant was removed after the centrifugation. To modify the surface of the AuNPs, protein A (0.25 mg/ml) in PBS was used to resuspend the AuNPs. The conjugation was conducted by rotating the mixture for 60 min. The modified AuNPs were separated from the suspension by centrifugation for 6 min at 13,000 rpm. The nanoparticles were washed by adding 200 µl of 0.01 PBS and centrifuged. After removing the supernatant, 100 µl of 1 mg/ml antibody and 100 µl PBS were added to the tube and mixed for 60 min by rotating. After separating the AuNP-antibody (AuNP-pAb) conjugates, two hundred microliters of the blocking agent were added to the tube. The mixture was rotated for 30 min. Finally, the AuNP-pAb conjugates were separated from the suspension by centrifugation, and the final suspension of the conjugates in PBS was stored at 4° C. Similar to Example 4 above, the dextrin capping agent, not having been entirely removed by an explicit ligand exchange process, partially remained as a capping/stabilizing agent for the AuNP-pAb conjugates (e.g., the adsorbed protein A and antibodies may displace some (but not all) of the capping agent from the AuNP surface).

Figure 15:
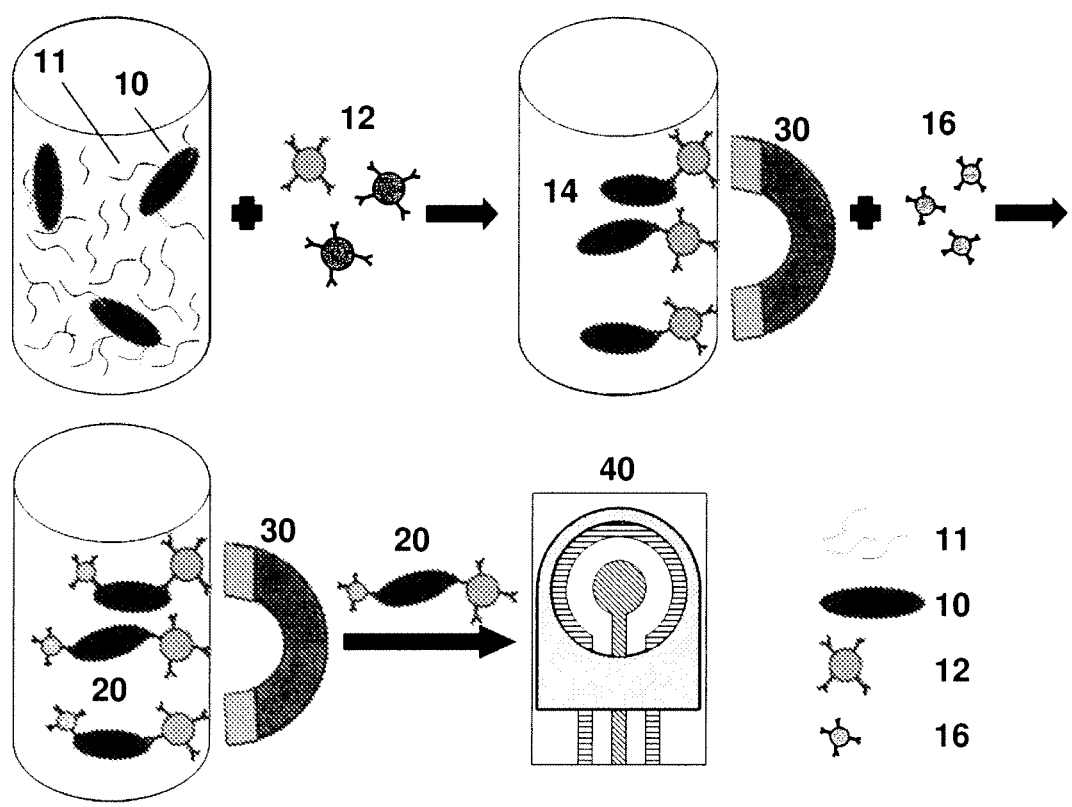
FIG. 15 is a schematic illustrating the capture, separation, and detection of a target pathogen using a carbohydrate-capped metal nanoparticle according to the disclosure.

Bacteria Detection:

The process for the capture, separation, and detection of the target pathogen 10 is illustrated in FIG. 15. The blank control for the tests was peptone water in the same volume as the sample 11. Firstly, 400 µl of PBS, 50 µl of cell dilution (or peptone water for the control) and 50 µl of MNP-mAb conjugates 12 were combined in a 2 ml sterile tube. After 15 min hybridization, PBS (55 µl, 0.01 M) with 0.1% BSA was added to the mixture as a blocking agent. Then, the MNP-*E. coli* complexes 14 were magnetically separated from the sample matrix 11 solution using a magnet 30 and resuspended in 450 µl of PBS. Secondly, the dextrin-capped AuNP-pAb conjugates 16 were introduced to the system, followed by 15 min hybridization to form MNP-mAb-target-pAb-AuNP complexes/conjugates 20. After washing the complexes 20 once with 0.01 M PBS, the complexes 20 were resuspended in 500 µl of PBS with 0.05% TRITON-X100, and left stand for a few minutes. Finally, the complexes 20 were suspended in 500 µl of PBS. One hundred microliters of the suspension were plated on SMAC for cell counting. The rest were magnetically separated from the supernatant (400 µl).

Electrochemical Measurement.

The target bacteria were detected by measuring the electrochemical signal of AuNPs. Each sample obtained as described above (complexes 20 magnetically separated from supernatant) was combined with 100 µl 1 M HCl (to generate $Au^{3+}$ ions for detection as the analyte/bacterial label from the AuNPs) and was introduced to the SPCE chip 40. An oxidation potential of 1.4 V vs. Ag/AgCl was applied to the working electrode. After oxidation, a differential pulse voltammetric (DPV) measurement was performed. The scan was from −1.5 V to 1.5 V. The potential and currents were recorded. All measurements were performed at room temperature. Each sample was measured three times. At least three samples for each concentration of bacteria were tested.

Figure 16:
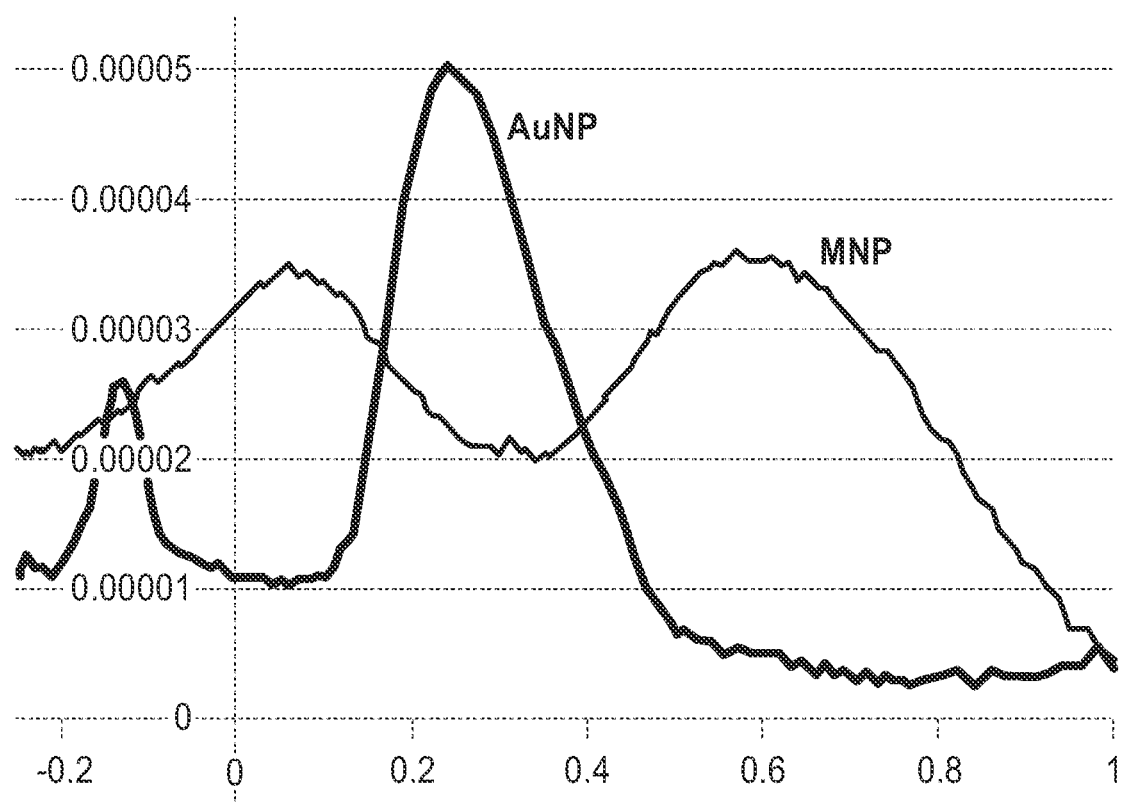
FIG. 16 is a graph comparing the differential pulse voltammetric (DPV) sensorgrams of dextrin-capped gold nanoparticles (AuNPs) and magnetic nanoparticles (MNPs). The AuNPs show a characteristic current peak at 0.25 V and the MNPs show a current peak at 0.58V.
Figure 17:
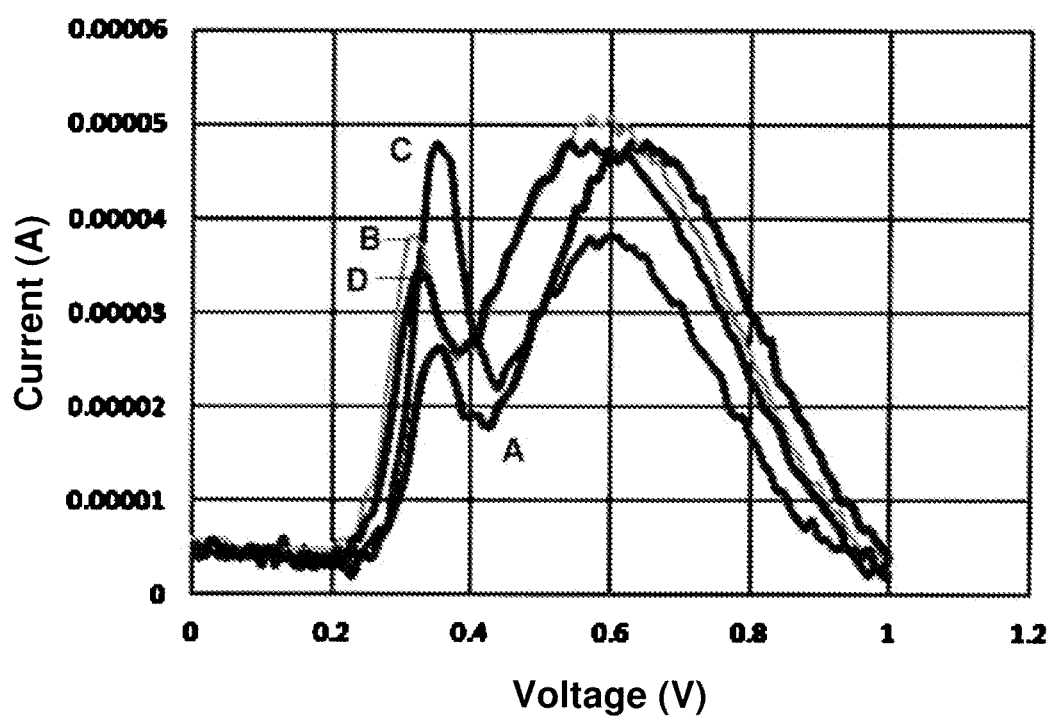
FIG. 17 is a graph comparing the DPV sensorgram of AuNP-labeled *E. coli* O157:H7 detected with an SPCE biosensor at variable bacterial cell concentrations (A: negative control, B: $10^4$ cfu/ml, C: $10^6$ cfu/ml, D: $10^2$ cfu/ml). The peak current for AuNP at about 0.25V to 0.3V increases with increasing cell concentration.
Figure 18:
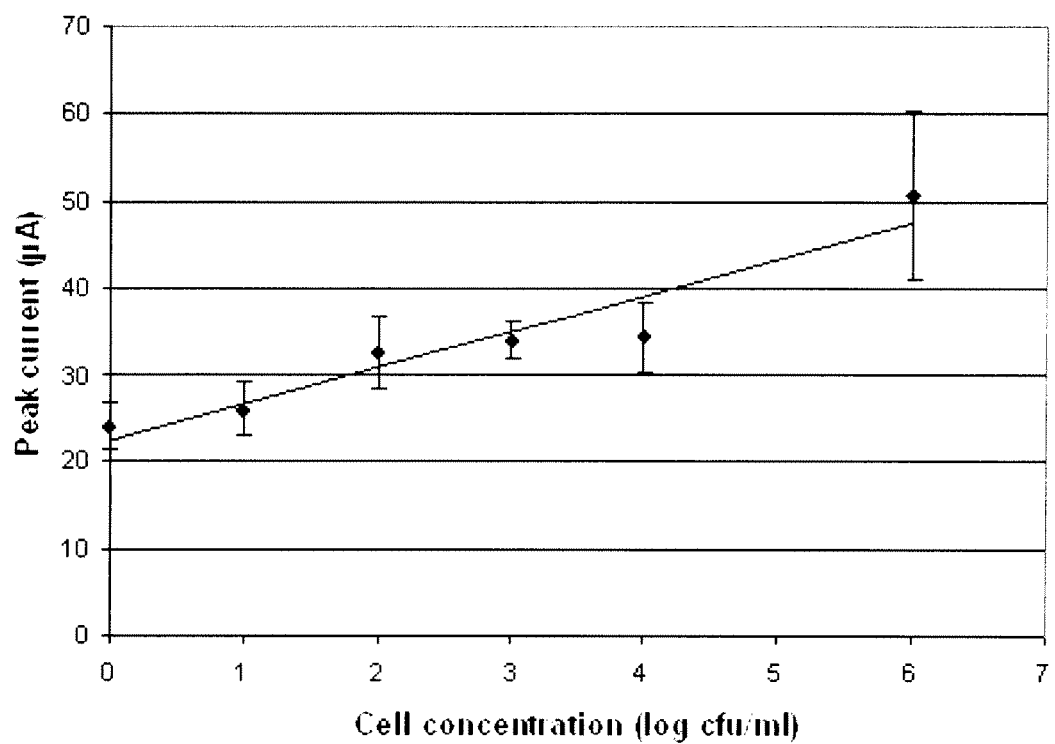
FIG. 18 is a graph of peak DPV current vs. cell concentration of the AuNP-labeled *E. coli* O157:H7. The signal shows a linear relationship between $10^1$ to $10^6$ cfu/ml.

Results: FIG. 16 shows typical DPV sensorgrams of native AuNPs and native magnetic nanoparticles (MNPs). The current peak for AuNPs is at 0.25V and MNPs is at 0.58V. FIG. 17 shows typical DPV sensorgrams for the detection of *E. coli* O157:H7 at different cell concentrations ($10^2$, $10^4$, and $10^6$ cfu/ml) relative to a negative control. The sensorgrams show a wider curve which seems to include both AuNPs and MNPs. For the analysis, the peak current to the left (representing AuNPs) was chosen for signal reporting. As shown in the FIG. 17, the peak current for AuNPs increases with increasing cell concentration. FIG. 17 also shows the formation of the MNP-cell-AuNP complex. The amount of target cells detected is proportional to the amount of AuNPs. The lowest measured cell concentration in FIG. 17 was detectable at $10^2$ cfu/ml. FIG. 18 is a plot of the peak (gold) current vs. cell concentration for the MNP-cell-AuNP complex, and it shows a linear relationship between the peak DPV current and the log cell concentration between $10^1$ and $10^6$ cfu/ml. The results verify that AuNP could be used for labeling the target cells, and the magnetic separation is effective.

Example 6—Synthesis of Functionalized Gold Nanoparticles with a Nanotracer for *E. coli* Detection This example describes the formation and testing of a nanotracer-labeled nanoparticle designed for the rapid detection of *Escherichia coli* O157:H7. The detection system includes antibody-functionalized, polymer-coated magnetic nanoparticles (MNP-mAb) as described in Example 5 for the capture and separation of target *E. coli* O157:H7 cells from a sample (broth) matrix. Dextrin-capped, antibody-functionalized gold nanoparticles (AuNP-pAb, with the polyclonal antibody pAb for *E. coli* O157:H7) as described in Example 5 are further functionalized to include metallic nanotracer (NT) particles (lead sulfide, PbS) attached to the AuNP substrate via barcode DNA/oligonucleotide (bDNA) as generally described in Alocilja et al. U.S. Publication No. 2011/0171749 (incorporated herein by reference in its entirety). The resulting functionalized gold nanoparticle (NT-bDNA-AuNP-pAb) is then used as an analyte label in which the lead ($Pb^{2+}$) of the NT serves as a detectable moiety for the electrochemical detection of the *E. coli* analyte (e.g., by square wave voltammetry).

The dextrin-capped, antibody-functionalized gold nanoparticles (AuNP-pAb) as described in Example 5 are further functionalized by attaching a thiolated, amine-functional bDNA oligonucleotide (5'-[amino]-GTC AGT CAG TCA GTC AGT CA-[thiol]-3' (SEQ ID NO: 6)). The bDNA is attached to the AuNP surface at the 3'-end via a thiol linkage using the DTT ligand exchange procedure generally described in Examples 1 and 2 above (i.e., thus essentially removing the dextrin capping agent from the intermediate bDNA-AuNP-pAb composition). Lead sulfide (PbS) NT particles are formed using the method of Salavati-Niasari et al. (2012). Briefly, lead nitrate ($Pb(NO_3)_2$) and thioglycolic acid ($HSCH_2COOH$) are reacted to form complexed PbS NT nanoparticles (e.g., containing carboxylic groups for further functionalization). The PbS NT nanoparticles are then attached to the 5'-end of the bDNA using 1-ethyl-3-(3-dimethylaminopropyl) carbodiimide (EDC) and N-hydroxysuccinimide (NHS) linkers as generally known in the art to form the resulting analyte label (NT-bDNA-AuNP-pAb).

Figure 19:
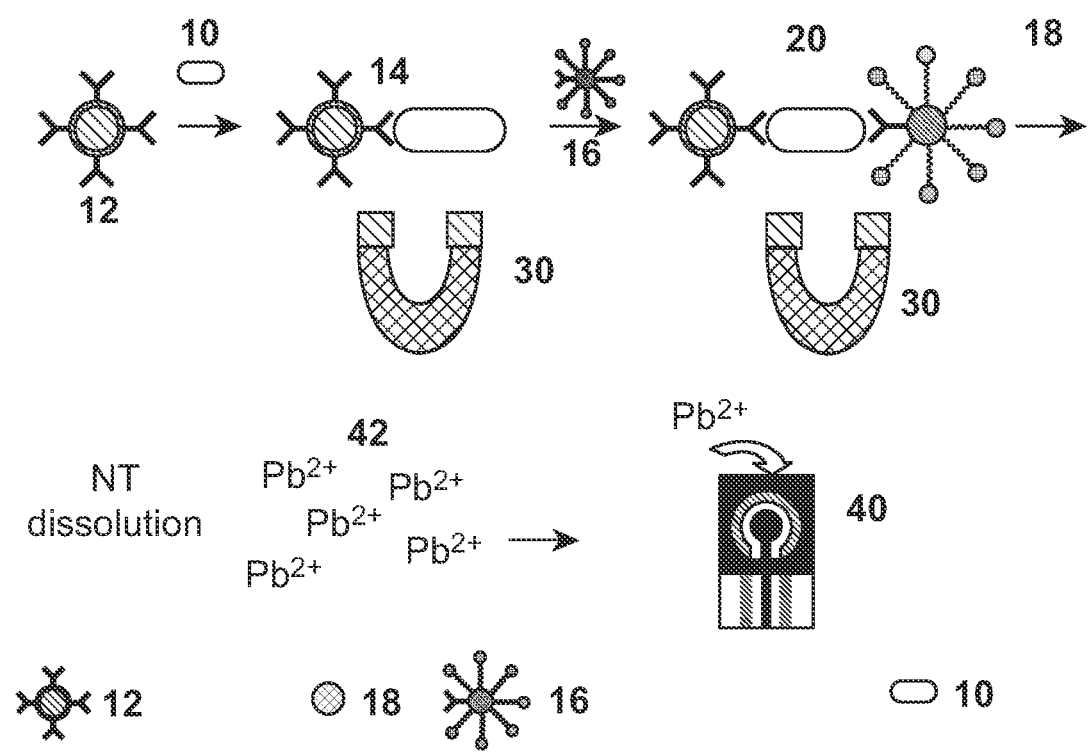
FIG. 19 is a schematic illustrating the capture, separation, and detection of a target pathogen using a metal nanoparticle including a nanotracer (NT) according to the disclosure.

FIG. 19 illustrates a process for the capture, separation, and detection of a target pathogen 10 similar to that of Example 5 and FIG. 15. Briefly, the MNP-mAb 12 nanoparticles are added to a sample volume containing the E. coli target analyte 10 to hybridize and form MNP-E. coli complexes 14. The MNP-E. coli complexes 14 are magnetically separated from the sample matrix solution using a magnet 30 and then resuspended in solution for combination with the analyte label 16 NT-bDNA-AuNP-pAb, followed by hybridization to form the triplex conjugate 20 MNP-E. coli-AuNP including the NT 18 as PbS nanoparticles tethered to the AuNP nanoparticle core via the bDNA. The triplex conjugates 20 are then magnetically separated/concentrated from the suspension for nanotracer 18 dissolution, thus releasing metal nanotracer ions 42 (e.g., $Pb^{2+}$) that can be detected and correlated to the presence of the analyte 10 by any suitable electrochemical method, such as square-wave voltammetry (e.g., using an SPCE biosensor 40 as illustrated). Other details related to the use and detection of barcode DNA nanotracer analyte labels may be found in Alocilja et al. U.S. Publication No. 2011/0171749.

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the compositions, processes, kits, or apparatus are described as including components, steps, or materials, it is contemplated that the compositions, processes, or apparatus can also comprise, consist essentially of, or consist of, any combination of the recited components or materials, unless described otherwise. Combinations of components are contemplated to include homogeneous and/or heterogeneous mixtures, as would be understood by a person of ordinary skill in the art in view of the foregoing disclosure.

REFERENCES

1. Ahmad A, Senapati S, Khan M I, Kumar R, Sastry M (2003) Extracellular biosynthesis of monodisperse gold nanoparticles by a novel extremophilic actinomycete, Thermomonospora sp. Langmuir 19 (8):3550-3553
2. Andreescu D, Sau T K, Goia D V (2006) Stabilizer-free nanosized gold sols. J Colloid Interface Sci 298 (2):742-751
3. Asian K, Lakowicz J R, Geddes C D (2005) Nanogold plasmon resonance-based glucose sensing. 2. Wavelength-ratiometric resonance light scattering. Anal Chem 77 (7):2007-2014
4. Bharde A, Kulkarni A, Rao M, Prabhune A, Sastry M (2007) Bacterial enzyme mediated biosynthesis of gold nanoparticles. J Nanosci Nanotechnol 7 (12):4369-4377
5. Brust M, Walker M, Bethell D, Schiffrin D J, Whyman R (1994) Synthesis of thiol-derivatized gold nanoparticles in a 2-phase liquid-Liquid system. J Chem Soc, Chem Commun (7):801-802
6. Chah S, Hammond M R, Zare R N (2005) Gold nanoparticles as a colorimetric sensor for protein conformational changes. Chem Biol 12 (3):323-328
7. Daniel M C, Astruc D (2004) Gold nanoparticles: assembly, supramolecular chemistry, quantum-size-related properties, and applications toward biology, catalysis, and nanotechnology. Chem Rev 104 (1):293-346
8. Das S K, Das A R, Guha A K (2009) Gold manoparticles: Microbial synthesis and application in water hygiene management. Langmuir 25 (14):8192-8199
9. de la Fuente J M, Penades S (2006) Glyconanoparticles: types, synthesis and applications in glycoscience, biomedicine and material science. Biochim Biophys Acta 1760 (4):636-651
10. Dudak F C (2009) Rapid and label-free bacteria detection by surface plasmon resonance (SPR) biosensors. Biotechnol J (4):1003-1011
11. Goluch E D, Nam J M, Georganopoulou D G, Chiesi T N, Shaikh K A, Ryu K S, Barron A E, Mirkin C A, Liu C (2006) A bio-barcode assay for on-chip attomolar-sensitivity protein detection. Lab Chip 6 (10):1293-1299
12. Hill H D, Mirkin C A (2006) The bio-barcode assay for the detection of protein and nucleic acid targets using DTT-induced ligand exchange. Nat Protoc 1 (1):324-336
13. Huang Y J, Li D, Li J H (2004) beta-cyclodextrin controlled assembling nanostructures from gold nanoparticles to gold nanowires. Chem Phys Lett 389 (1-3):14-18
14. Ji X, Song X, Li J, Bai Y, Yang W, Peng X (2007) Size control of gold nanocrystals in citrate reduction: the third role of citrate. J Am Chem Soc 129 (45):13939-13948
15. Kimling J, Maier M, Okenve B, Kotaidis V, Ballot H, Plech A (2006) Turkevich method for gold nanoparticle synthesis revisited. J Phys Chem B 110 (32):15700-15707
16. Li Z, Jin R C, Mirkin C A, Letsinger R L (2002) Multiple thiol-anchor capped DNA-gold nanoparticle conjugates. Nucleic Acids Research 30 (7):1558-1562
17. Ma Z, Han H (2008) One-step synthesis of cystine-coated gold nanoparticles in aqueous solution. Colloids Surf A 317 (1-3):229-233
18. Polte J, Ahner T T, Delissen F, Sokolov S, Emmerling F, Thunemann A F, Kraehnert R (2010) Mechanism of gold nanoparticle formation in the classical citrate synthesis method derived from coupled in situ XANES and SAXS evaluation. J Am Chem Soc 132 (4):1296-1301
19. Porta F, Michele R (2003) Gold nanostructured materials for the selective liquid phase catalytic oxidation. J Mol Catal A Chem 204-205 (15):553-559
20. Pal S, Alocilja E C, Downes F P (2007) Nanowire labeled direct-charge transfer biosensor for detecting Bacillus species. Biosens Bioelectron 22 (9-10):2329-2336
21. Rechberger W, Hohenau A, Leitner A, Krenn J R, Lamprecht B, Aussenegg F R (2003) Optical properties of two interacting gold nanoparticles. Opt Commun 220 (1-3):137-141
22. Selvakannan P, Mandal S, Phadtare S, Gole A, Pasricha R, Adyanthaya S D, Sastry M (2004) Water-dispersible tryptophan-protected gold nanoparticles prepared by the spontaneous reduction of aqueous chloroaurate ions by the amino acid. J Colloid Interface Sci 269 (1):97-102
23. Slocik J M, Stone M O, Naik R R (2005) Synthesis of gold nanoparticles using multifunctional peptides. Small 1 (11):1048-1052
24. Torres-Chavolla E, Ranasinghe R J, Alocilja E C (2010) Characterization and functionalization of biogenic gold nanoparticles for biosensing enhancement. IEEE Trans Nanotechnol 9 (5):533-538

25. Turkevich J, Stevenson P C, Hillier J (1951) A study of the nucleation and growth processes in the synthesis of colloidal gold. Discuss Faraday Soc (11):55-&
26. Wang Y, Yang H (2006) Oleic acid as the capping agent in the synthesis of noble metal nanoparticles in imidazolium-based ionic liquids. Chem Commun (24):2545-2547
27. Xiliang L, Aoife M, Anthony J K, Malcolm R S (2006) Application of nanoparticles in electrochemical sensors and biosensors. Electroanalysis 18 (4):319-326
28. Zhang D, Carr D J, Alocilja E C (2009) Fluorescent bio-barcode DNA assay for the detection of *Salmonella enterica* serovar *Enteritidis*. Biosens Bioelectron 24 (5): 1377-1381
29. Zhou M, Wang B, Rozynek Z, Xie Z, Fossum J O, Yu X, Raaen S (2009) Minute synthesis of extremely stable gold nanoparticles. Nanotechnology 20 (50):505606
30. Anderson, M., Torres-Chavolla, E., Castro, B., Alocilja, E., 2010. J. Nanopart. Res. DOI: 10. 1007/s11051-010-0172-3.
31. Andresen, D., von Nickisch-Rosenegk, M., Bier, F. F., 2009b. Clin. Chim. Acta. 403, 1-2:244-248.
32. Azzazy, H. M. E., Mansour, M. M. H., Kazmierczak, S. C., 2006. Clin. Chem. 52, 7:1238-1246.
33. Chow, W. H., McCloskey, C., Tong, Y., Hu, L., You, Q., Kelly, C. P., et al., 2008. J. Mol. Diagn. 10, 5:452-458.
34. Dalovisio, J. R., Montenegro-James, S., Kemmerly, S. A., Genre, C. F., Chambers, R., Greer, D., et al., 1996. Clin. Infec. Dis. 23, 5:1099-1106.
35. Demidov, V. V., 2002. Expert Rev. Mol. Diagn. 2, 6:542-548.
36. Fernandez, J. G., Fernandez-de-Mera, I., Reyes, L. E., Ferreras, M. C., Perez, V., Gortazar, C., et al., 2009. J. Vet. Diagn. Invest. 21, 1:102-107.
37. Gill, P., Alvandi, A. H., bdul-Tehrani, H., Sadeghizadeh, M., 2008. Diagn. Microbiol. Infect. Dis. 62, 2:119-124.
38. Gill, P., Ghaemi, A., 2008. Nucleos. Nucleot. Nucl. 27, 3:224-243.
39. Goldmeyer, J., Li, H., McCormac, M., Cook, S., Stratton, C., Lemieux, B., et al., 2008. J. Microbiol. 46, 4:1534-1536.
40. Guo, S. J., Wang, E. K., 2007. Anal. Chim. Acta. 598, 2:181-192.
41. Hellyer, T. J., Nadeau, J. G., 2004. Expert Rev. Mol. Diagn. 4, 2:251-261.
42. Jeong, Y. J., Park, K., Kim, D. E., 2009. Cell. Mol. Life Sci. 66, 20:3325-3336.
43. Lixin, A., Wen, T., Tamara, A. R., Hyun-Jin, K., Jamie, W., Huimin, K., 2005. J. Biol. Chem. 280, 32:28952-28958.
44. Mahalanabis, M., Do, J., ALMuayad, H., Zhang, J., Klapperich, C., 2010. Biomed. Microdevices. 12, 2:353-359.
45. Mori, Y., Notomi, T., 2009. J. Infect. Chemother. 15, 2:62-69.
46. Palomino, J. C., 2005. Eur. Respir. J. 26, 2:339-350.
47. Perkins, M. D., Roscigno, G., Zumla, A., 2006. Lancet. 367, 9514:942-943.
48. Pumera, M., Aldavert, M., Mills, C., Merkoti, A., Alegret, S., 2005. Electrochim. Acta. 50, 18:3702-3707.
49. Vincent, M., Xu, Y., Kong, K., 2004. EMBO Rep. 5, 8:795-800.
50. WHO global tuberculosis control 2009. Epidemiology, strategy, and financing. http://www.who.int/tb/publications/global_report/2009/pdf/full_report.pdf.
51. Zhang, D., Huarng, M. C., Alocilja, E. C., 2010. Biosens. Bioelectron. 26, 4:1736-1742.
52. Steve Rozen and Helen J. Skaletsky (2000) Primer3 on the WWW for general users and for biologist programmers. In: Krawetz S, Misener S (eds) Bioinformatics Methods and Protocols: Methods in Molecular Biology. Humana Press, Totowa, N.J., pp 365-386. Source code available at http://fokker.wi.mit.edu/primer3/.
53. DeLong, et al., 2010. Nanotechnology, Science and Applications, 3:53-63.
54. Adinolfi et al., 2004. Org. Biomol. Chem. 2, 1879-1886.
55. Pourceau et al. 2009. Curr. Protoc. Nucleic Acid Chem. 39:4.38.1-4.38.25.
56. Salavati-Niasari et al. 2012. Polyhedron, vol. 35, issue 1, p. 149-153 (Mar. 16, 2012).

What is claimed is:

1. A stabilized metal nanoparticle suspension composition comprising:
   (a) water in sufficient amount to provide an aqueous medium; and
   (b) a plurality of stabilized metal nanoparticles stably suspended in the aqueous medium, each stabilized metal nanoparticle comprising:
      (i) a metal nanoparticle core and
      (ii) at least one of a linear and a branched carbohydrate capping agent present adsorbed as a layer on an outer surface of the metal nanoparticle core in an amount sufficient to stabilize the metal nanoparticle suspension;
   wherein:
      the plurality of stabilized metal nanoparticles has an average particle size ranging from 5 nm to 15 nm; and
      the carbohydrate capping agent comprises one or more glucose residues.

2. The composition of claim 1, wherein the stabilized metal nanoparticles are capable of remaining stably suspended in the aqueous medium for a period of at least 90 days when stored at room temperature.

3. The composition of claim 1, wherein the metal nanoparticles comprise gold nanoparticles.

4. The composition of claim 1, wherein the pH value of the aqueous medium ranges from 7 to 12.

5. The composition of claim 1, wherein the carbohydrate capping agent comprises dextrin.

6. The composition of claim 1, wherein the carbohydrate capping agent comprises an oligosaccharide having 3 to 100 saccharide residues.

7. The composition of claim 6, wherein the carbohydrate capping agent further comprises at least one of a monosaccharide and a disaccharide.

8. The composition of claim 1, wherein the carbohydrate capping agent comprises a plurality of oligosaccharides having a distribution of lengths with a number-average of saccharide residues ranging from 10 to 100.

9. The composition of claim 1, wherein the carbohydrate capping agent is in a substantially non-oxidized form.

10. The composition of claim 1, wherein the plurality of stabilized metal nanoparticles has a normal size distribution with a standard deviation of 25% or less relative to the average particle size of the distribution.

11. The composition of claim 1, wherein:
   the stabilized metal nanoparticles have a spherical shape; and
   the plurality of stabilized metal nanoparticles has an average particle size ranging from 8 nm to 15 nm.

12. The composition of claim 1, wherein the stabilized metal nanoparticles further comprise:
   (iii) a binding pair member comprising (A) an immobilization moiety for immobilizing the binding pair member onto the metal nanoparticle core and (B) a binding moiety capable of binding to a target analyte or a second binding pair member, wherein the binding pair member is immobilized on the outer surface of the metal nanoparticle via the immobilization moiety.

13. The composition of claim 12, wherein the immobilization moiety of the binding pair member comprises a carbohydrate moiety conjugated to the binding moiety.

14. A stabilized gold nanoparticle suspension composition comprising:
   (a) water in sufficient amount to provide an aqueous medium; and
   (b) a plurality of stabilized gold nanoparticles stably suspended in the aqueous medium, each stabilized gold nanoparticle comprising:
      (i) a gold nanoparticle core, and
      (ii) at least one of a linear and a branched dextrin capping agent present adsorbed as a layer on an outer surface of the gold nanoparticle core in an amount sufficient to stabilize the gold nanoparticle suspension;
   wherein:
      the plurality of stabilized gold nanoparticles has an average particle size ranging from 5 nm to 15 nm; and
      the dextrin capping agent has at least 10 saccharide residues.

15. The composition of claim 14, wherein:
   the stabilized gold nanoparticles have a spherical shape;
   the plurality of stabilized gold nanoparticles has an average particle size ranging from 8 nm to 15 nm; and
   the plurality of stabilized gold nanoparticles has a normal size distribution with a standard deviation of 25% or less relative to the average particle size of the distribution.

16. The composition of claim 14, wherein the stabilized gold nanoparticles further comprise:
   (iii) a binding pair member comprising (A) an immobilization moiety for immobilizing the binding pair member onto the gold nanoparticle core and (B) a binding moiety capable of binding to a target analyte or a second binding pair member, wherein the binding pair member is immobilized on the outer surface of the gold nanoparticle via the immobilization moiety.

17. The composition of claim 16, wherein the immobilization moiety of the binding pair member comprises a carbohydrate moiety conjugated to the binding moiety.

* * * * *

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 1
ttattcgtag ctaaaaaaaa aa                                              22

<210> SEQ ID NO 2
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 2
gagcgtaggc gtcggtgaca aagg                                            24

<210> SEQ ID NO 3
<211> LENGTH: 24
```

```
<212> TYPE: DNA
<213> ORGANISM: Artificial Sequence
<220> FEATURE:
<223> OTHER INFORMATION: Synthetic oligonucleotide

<400> SEQUENCE: 3
gcttcggacc accagcacct aacc                                              24

<210> SEQ ID NO 4
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 4
aaaaaaaaaa aagagcgtag gcgtcggtga                                        30

<210> SEQ ID NO 5
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 5
gtgctggtgg tccgaagcaa aaaaaaaaaa                                        30

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
gtcagtcagt cagtcagtca                                                   20
```